(12) United States Patent
Hatanaka

(10) Patent No.: US 9,540,663 B2
(45) Date of Patent: Jan. 10, 2017

(54) XYLOSE-FERMENTING MICROORGANISM

(75) Inventor: Haruyo Hatanaka, Osaka (JP)

(73) Assignee: SUNTORY HOLDINGS LIMITED, Osaka (JP)

(*) Notice: Subject to any disclaimer, the term of this patent is extended or adjusted under 35 U.S.C. 154(b) by 43 days.

(21) Appl. No.: 14/000,475

(22) PCT Filed: Feb. 24, 2012

(86) PCT No.: PCT/JP2012/055294
§ 371 (c)(1),
(2), (4) Date: Nov. 4, 2013

(87) PCT Pub. No.: WO2012/115277
PCT Pub. Date: Aug. 30, 2012

(65) Prior Publication Data
US 2014/0162334 A1    Jun. 12, 2014

(30) Foreign Application Priority Data

Feb. 25, 2011 (JP) ................. 2011-040651

(51) Int. Cl.
| | |
|---|---|
| C12P 7/06 | (2006.01) |
| C12N 15/09 | (2006.01) |
| C12N 1/22 | (2006.01) |
| C12N 9/12 | (2006.01) |
| C12N 15/81 | (2006.01) |
| C12P 7/10 | (2006.01) |
| C07K 14/395 | (2006.01) |

(52) U.S. Cl.
CPC ............. *C12P 7/06* (2013.01); *C07K 14/395* (2013.01); *C12N 1/22* (2013.01); *C12N 9/1205* (2013.01); *C12N 15/09* (2013.01); *C12N 15/81* (2013.01); *C12P 7/10* (2013.01); *C12Y 207/01023* (2013.01); *Y02E 50/16* (2013.01); *Y02P 20/52* (2015.11)

(58) Field of Classification Search
None
See application file for complete search history.

(56) References Cited

U.S. PATENT DOCUMENTS

2010/0028975 A1* 2/2010 Gorwa-Grauslund ... 435/254.21
2010/0291648 A1* 11/2010 Alper .................. C12N 9/0006
                                                            435/161

OTHER PUBLICATIONS

P21373 (last viewed on Mar. 6, 2015).*
P23900 (last viewed on Mar. 6, 2015).*
Shi et al., Identification of ATP-NADH kinase isozymes and their contribution to supply of NADP(H) in *Saccharomyces cerevisiae.*, FEBS J. (2005), vol. 272(13), pp. 3337-3349.*
(Continued)

*Primary Examiner* — Alexander Kim
(74) *Attorney, Agent, or Firm* — Greenblum & Bernstein, P.L.C.

(57) ABSTRACT

The object of the present invention is to provide a microorganism capable of maintaining its xylose fermentation ability over a long period of time. The present invention also provides a microorganism deficient in the function of expressing NAD kinase gene and/or FPS1 gene, a method for preparing the above microorganism and a method for producing ethanol using the above microorganism.

9 Claims, 37 Drawing Sheets

(56) References Cited

OTHER PUBLICATIONS

Kawai et al., Molecular cloning and identification of UTR1 of a yeast *Saccharomyces cerevisiae* as a gene encoding an NAD kinase., FEMS Microbiology Letters (2001), vol. 200, pp. 181-184.*

Watanabe et al., Complete Reversal of Coenzyme Specificity of Xylitol Dehydrogenase and Increase of Thermostability by the Introduction of Structural Zinc., The Journal of Biological Chemistry (2005), vol. 280, pp. 10340-10349.*

Xiong et al., Alteration of xylose reductase coenzyme preference to improve ethanol production by *Saccharomyces cerevisiae* from high xylose concentrations., Bioresource Technology (Epub Aug. 9, 2011), vol. 102, Issue 19, Oct. 2011, pp. 9206-9215.*

Shi et al., "The Effect of NAD Kinase Homologues on the β-oxidation of Unsaturated Fatty Acids with the Double Bond at an Even Position in *Saccharomyces cerevisiae*", *Chinese Journal of Biotechnology*, vol. 22, No. 4, pp. 667-671, 2006, including an English-language abstract.

Zhang et al., "Progress of Engineered *Saccharomyces cerevisiae* of Xylose Metabolism and Fermentation for Ethanol Production", Apr. 20, vol. 35. No. 4, pp. 572-576, 2008, including an English-language abstract.

Shen et al., "Construction of Industrial *Saccharomyces cerevisiae* Expressing Xylose-Metabolizing Genes in XI Pathway", *China Biotechnology*, vol. 25, No. 9, pp. 69-73, 2005, including an English-language abstract.

International Search Report for PCT/JP2012/055294, mailed May 15, 2012, along with an English language translation.

Watanabe et al., "Ethanol production from xylose by recombinant *Saccharomyces cerevisiae* expressing protein engineered $NADP^+$-dependent xylitol dehydrogenase", *J. Biotechnol.*, vol. 130, No. 3, pp. 316-319, 2007.

Bieganowski et al., "Synthetic lethal and biochemical analyses of NAD and NADH kinases in *Saccharomyces cerevisiae* establish separation of cellular functions", *J. Biol. Chem.*, vol. 281, No. 32, pp. 22439-22445, 2006.

Zhang et al., "Effect of *FPS1* deletion on the fermentation properties of *Saccharomyces cerevisiae* ", *Lett. Appl. Microbiol.*, vol. 44, No. 2, pp. 212-217, 2007.

Yu et al., "Reduction of glycerol production to improve ethanol yield in an engineered *Saccharomyces cerevisiae* using glycerol as a substrate", *J. Biotechnol.*, vol. 150, No. 2, pp. 209-214, 2010.

Miyagi et al., "Two sources of mitochondrial NADPH in the yeast *Saccharomyces cerevisiae*", *J. Biol. Chem.*, vol. 284, No. 12, pp. 7553-7560, 2009.

Kawai et al., "Structure and function of NAD kinase and NADP phosphatase: key enzymes that regulate the intracellular balance of NAD(H) and NADP(H)", *Biosci. Biotechnol. Biochem.*, vol. 72, No. 4, pp. 919-930, 2008.

Extended European Search Report for European Patent Application No. 12749891.3, mailed Apr. 24, 2015.

English translation of Hatanaka et al., "NAD kinase Hakai Kabu ni yoru Xylose kara no Ethanol Hakko Shuritsu no Kaizen", Japan Society for Bioscience, Biotechnology, and Agrochemistry 2011 Nendo Taikai Koen Yoshishu, 2011, vol. 2011, p. 170, 3BO3a10.

* cited by examiner

XYLOSE-FERMENTING MICROORGANISM

SEQUENCE LISTING

The instant application contains a Sequence Listing which has been submitted electronically in ASCII format and is hereby incorporated by reference in its entirety. Said ASCII copy, created on Oct. 24, 2013, is named P43984_SL.txt and is 62,854 bytes in size.

TECHNICAL FIELD

The present invention relates to a microorganism deficient in the function of expressing NAD kinase gene. The present invention also relates to a method for preparing a fermentative microorganism whose xylose fermentation ability is increased by causing a deficiency in the function of NAD kinase gene. The present invention further relates to a method for producing ethanol, which comprises a step of contacting the above microorganism with xylose-containing raw materials.

BACKGROUND ART

In recent years, in terms of fossil fuel depletion and/or the necessity of $CO_2$ gas reduction, studies have been pursued to produce ethanol as a fuel from biomass such as corncob, rice straw, switchgrass, Erianthus, scrap wood and so on, which have been wasted. Since many thousands of years ago, humans have already had techniques to convert starch into ethanol through fermentation by the action of yeast *Saccharomyces cerevisiae*. Starch is a polysaccharide composed of glucoses linked via α-1,4 linkages and can be easily degraded by the action of hydrolases present in various organisms. Glucose is the most preferred carbon source for yeast *Saccharomyces cerevisiae*, and two molecules of ethanol are produced through fermentation from one molecule of glucose. In contrast, biomass contains cellulose or hemicellulose as a polysaccharide.

Among them, cellulose is a polysaccharide composed of glucoses linked via β-1,4 linkages and is in a crystalline structure. Cellulose has some problems, e.g., in that pretreatment is required to disrupt its crystalline structure and in that enzymes required for its degradation, such as cellobiohydrolase I, cellobiohydrolase II and endoglucanase, do not have sufficient activity. However, there is no problem in fermenting cellulose by the action of yeast *Saccharomyces cerevisiae*, because the sugar produced after degradation is glucose.

In contrast, hemicellulose comprises not only glucose, but also pentoses such as xylose and arabinose. However, yeast *Saccharomyces cerevisiae* is conventionally unable to ferment these pentoses. For this reason, techniques to allow genes for xylose reductase and xylitol dehydrogenase from xylose-fermentable yeast *Pichia stipitis* to be highly expressed in yeast *Saccharomyces cerevisiae* have often been used for xylose fermentation (FIG. 1). Xylose reductase in *Pichia stipitis* is an enzyme that uses NADPH as a major coenzyme, and one molecule of NADP is generated after reaction. On the other hand, xylitol dehydrogenase is an enzyme that uses NAD as a major coenzyme, and one molecule of NADH is generated after reaction. Thus, as shown in FIG. 1, the balance of NADP/NADPH or NAD/NADH remains unchanged during glucose fermentation, whereas this balance is shifted to increase NADP or NADH during xylose fermentation. This would be responsible for the low yield in ethanol fermentation from xylose.

Many attempts have been made to prepare a mutated xylose reductase whose coenzyme specificity is altered to NADH (Non-patent Document 1), to prepare a mutated xylitol dehydrogenase whose coenzyme specificity is altered to NADPH (Non-patent Document 2), to design an experiment where a gene for the glycolytic enzyme glyceraldehyde triphosphate dehydrogenase with coenzyme specificity for NADPH is introduced from another organism species (Non-patent Document 3), and to express transhydrogenases (which transfer hydrogen between NADPH and NAD or between NADP and NADH) derived from bacteria such as *E. coli* (Non-patent Document 4), but these attempts have not succeeded in providing sufficient effects.

PRIOR ART DOCUMENTS

Non-patent Documents

Non-patent Document 1: Petschacher B, Nidetzky B. Microb Cell Fact. 2008 Mar. 17; 7:9.

Non-patent Document 2: Watanabe S, Saleh A A, Pack S P, Annaluru N, Kodaki T, Makino K. J. Biotechnol. 2007 Jun. 30; 130(3): 316-9. Epub 2007 April 29.

Non-patent Document 3: Verho R, Londesborough J, Penttile M, Richard P. Appl Environ Microbiol. 2003 October; 69(10): 5892-7.

Non-patent Document 4: Mikael Anderlund et. al. Appl Environ Microbiol. 1999 June 65(6): 2333-2340

DISCLOSURE OF THE INVENTION

Under these circumstances, there is a demand for the development of a microorganism capable of maintaining its xylose fermentation ability over a long period of time.

Based on the concept that it is important to increase intracellular NAD or NADPH levels as a strategy for increasing the yield of ethanol in xylose fermentation, the inventors of the present invention have made extensive and intensive efforts with a focus on NAD(H) kinase. As a result, the inventors of the present invention have found that a decrease in NAD levels during the following reaction:

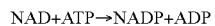

$$NAD+ATP \rightarrow NADP+ADP$$

can be prevented when NAD(H) kinase gene is disrupted. Then, the inventors of the present invention have prepared a yeast strain whose NAD kinase gene is disrupted and have performed xylose fermentation using this yeast strain. As a result, this strain was found to improve the yield of ethanol in comparison with the same strain of wild type.

The present invention is based on the above findings.

Namely, the present invention is directed to the following.

[1] A microorganism deficient in the function of expressing NAD kinase gene.

[2] The microorganism according to [1] above, wherein the NAD kinase gene is at least one selected from UTR1 gene and YEF1 gene.

[3] The microorganism according to [1] or [2] above, which is further deficient in the function of expressing FPS1 gene.

[4] The microorganism according to any one of [1] to [3] above, which is yeast.

[5] The microorganism according to any one of [1] to [3] above, which is *Saccharomyces cerevisiae*.

[6] The microorganism according to any one of [1] to [5] above, which is transformed with a xylose-metabolizing enzyme gene.

[7] The microorganism according to [6] above, wherein the xylose-metabolizing enzyme gene is at least one selected from the group consisting of xylose reductase gene, xylitol dehydrogenase gene and xylulose kinase gene.

[8] A method for preparing a microorganism whose xylose fermentation ability is increased by causing a deficiency in the function of expressing NAD kinase gene.

[9] The method according to [8] above, wherein the NAD kinase gene is at least one selected from UTR1 gene and YEF1 gene.

[10] The method according to [8] or [9] above, which further comprises a step of causing a deficiency in the function of expressing FPS1 gene.

[11] The method according to any one of [8] to [10] above, wherein the microorganism is yeast.

[12] The method according to any one of [8] to [10] above, wherein the microorganism is *Saccharomyces cerevisiae*.

[13] The method according to any one of [8] to [12] above, wherein the microorganism is transformed with a xylose-metabolizing enzyme gene.

[14] The method according to [13] above, wherein the xylose-metabolizing enzyme gene is at least one selected from the group consisting of xylose reductase gene, xylitol dehydrogenase gene and xylulose kinase gene.

[15] A method for producing ethanol, which comprises a step of contacting the microorganism according to any one of [1] to [7] above with xylose-containing raw materials.

[16] A microorganism deficient in the function of expressing FPS1 gene.

[17] The microorganism according to [16] above, which is yeast.

[18] The microorganism according to [16] above, which is *Saccharomyces cerevisiae*.

[19] The microorganism according to any one of [16] to [18] above, which is transformed with a xylose-metabolizing enzyme gene.

[20] The microorganism according to [19] above, wherein the xylose-metabolizing enzyme gene is at least one selected from the group consisting of xylose reductase gene, xylitol dehydrogenase gene and xylulose kinase gene.

[21] A method for preparing a microorganism whose xylose fermentation ability is increased by causing a deficiency in the function of expressing FPS1 gene.

[22] The method according to [21] above, wherein the microorganism is yeast.

[23] The method according to [21] above, wherein the microorganism is *Saccharomyces cerevisiae*.

[24] The method according to any one of [21] to [23] above, wherein the microorganism is transformed with a xylose-metabolizing enzyme gene.

[25] The method according to [24] above, wherein the xylose-metabolizing enzyme gene is at least one selected from the group consisting of xylose reductase gene, xylitol dehydrogenase gene and xylulose kinase gene.

[26] A method for producing ethanol, which comprises a step of contacting the microorganism according to any one of [16] to [20] above with xylose-containing raw materials.

The present invention provides a microorganism excellent in xylose fermentation ability. Moreover, the microorganism of the present invention shows high xylose fermentation ability, either on a small scale or on a large scale which involves stirring. The microorganism of the present invention can also maintain its xylose fermentation ability at high level even when used in long-term fermentation such as serial batch fermentation (serial fermentation in which cropped yeast is reused). Moreover, with the use of a method for preparing the microorganism of the present invention, bred lines with high xylose fermentation ability can also be prepared from a wide range of microorganisms which are used as hosts. The microorganism of the present invention allows efficient production of ethanol starting from xylose-containing raw materials. Moreover, the microorganism of the present invention also allows efficient production of ethanol, even starting from biomass with low amino acid content, as long as such biomass contains xylose.

BEST MODES FOR CARRYING OUT THE INVENTION

Figure 1:
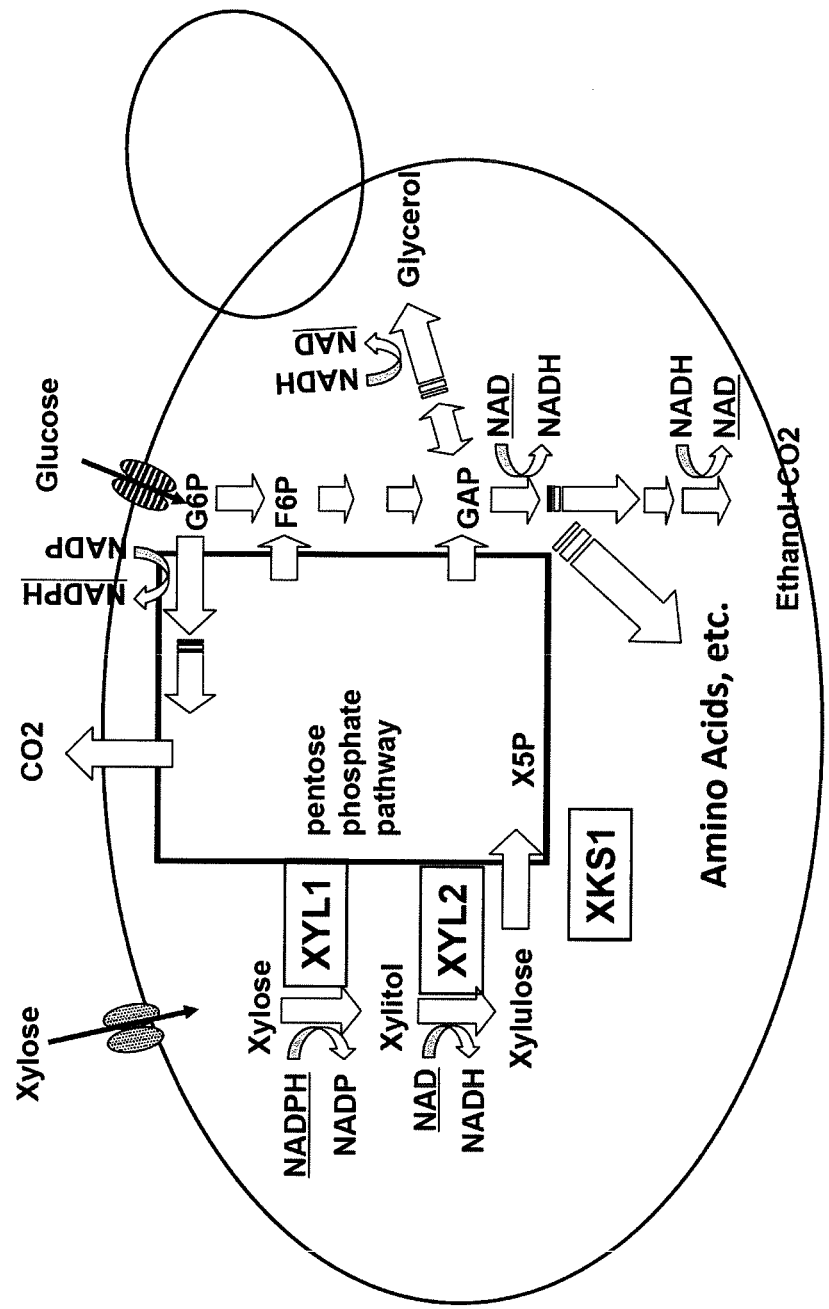
FIG. 1 shows the metabolic pathway of glucose and xylose.

The present invention will be described in more detail below. The following embodiments are illustrated to describe the present invention, and it is not intended to limit the present invention only to these embodiments. The present invention can be implemented in various modes, without departing from the spirit of the present invention.

It should be noted that all publications cited herein, including prior art documents, patent gazettes and other patent documents, are incorporated herein by reference. Moreover, this specification incorporates the contents disclosed in the specification and drawings of Japanese Patent Application No. 2011-040651 (filed on Feb. 25, 2011), based on which the present application claims priority.

The inventors of the present invention have found that when using a microorganism strain modified to suppress NAD kinase gene expression, the efficiency of ethanol production from xylose-containing raw materials is improved in comparison with a wild-type strain of the same species, and thus have completed the present invention. The inventors of the present invention have further found that when suppressing the expressions of glycerol channel genes, the efficiency of ethanol production from xylose-containing raw materials is further improved. The respective embodiments of the present invention will be described below.

1. Microorganism Deficient in the Function of NAD Kinase Gene

In a certain embodiment, the present invention provides a microorganism deficient in the function of expressing NAD kinase gene.

In the context of the present invention, the term "microorganism" is intended to mean an organism whose existence cannot be found by the unaided eye and whose size is equal to or smaller than that detectable under a microscope, etc. Examples of such a microorganism include prokaryotic organisms such as bacteria, cyanobacteria and archaebacteria, as well as eukaryotic organisms such as filamentous fungi, yeast, myxomycetes, basidiomycetes, unicellular algae and protozoa.

A preferred microorganism is of species with sugar fermentation ability, and more preferred is yeast, which may be either budding yeast or fission yeast. In a certain embodiment, the yeast may be budding yeast such as *Saccharomyces cerevisiae* NBRC1951, NBRC1952, NBRC1953, NBRC1954, X2180-1A (ATCC26786), CB11 (Berkley Stock Center), W303-1A (BY4848), etc. In another embodiment, the yeast may be fission yeast such as *Schizosaccharomyces japonicus* (*Hasegawaea japonicus*), *Schizosaccharomyces octosporus* (*Octosporomyces octosporus*), *Schizosaccharomyces pombe*, etc.

In the context of the present invention, the term "NAD kinase gene" is intended to mean a gene encoding NAD kinase protein, which may be either DNA or RNA. NAD kinase is an enzyme having the activity to convert nicotinamide adenine dinucleotide (NAD) into nicotinamide adenine dinucleotide phosphate (NADP) through phosphate addition (hereinafter referred to as "NAD kinase activity") (Magni G et al., (2006) Mini reviews in medicinal chemistry 6 (7): 739-46).

As used herein, the term "NAD kinase gene" is not limited to a gene (SEQ ID NO: 1 or 3) encoding a *Saccharomyces cerevisiae*-derived NAD kinase protein (SEQ ID NO: 2 or 4), and may also be a gene encoding a homolog protein which has NAD kinase activity and belongs to the same family as NAD kinase. Such proteins belonging to the same family as NAD kinase have been found in many plants and are highly conserved throughout the family. Since NAD kinase is an enzyme important for cell metabolism, a gene for this enzyme is highly conserved throughout the family. The genes for NAD kinases or homolog proteins thereof have already been analyzed for their nucleotide sequences in a plurality of microorganisms, and the sequence information thereof have been registered in the database (see Table 1).

In the case of using *Saccharomyces cerevisiae* to prepare the microorganism of the present invention, the NAD kinase gene is preferably UTR1 gene (SEQ ID NO: 1) or YEF1 gene (SEQ ID NO: 3).

In one embodiment, the NAD kinase gene may be a mutant with deletion, insertion, substitution or addition of one or more nucleotides in the nucleotide sequence of a polynucleotide encoding a polypeptide with NAD kinase activity. Such a mutant may be mutated in either or both of coding and non-coding regions. Mutations in coding regions may produce conservative or non-conservative amino acid deletions, insertions, substitutions and/or additions. As used herein, the term "NAD kinase gene" also encompasses a gene encoding the amino acid sequence shown in SEQ ID NO: 2 or SEQ ID NO: 4 or a gene encoding an amino acid sequence with deletion, substitution or addition of one or more amino acids (e.g., 1 to 40 amino acids, 1 to 20 amino acids, 1 to 15 amino acids, 1 to 10 amino acids, 1 to 9 amino acids, 1 to 8 amino acids, 1 to 7 amino acids, 1 to 6 amino acids, 1 to 5 amino acids, 1 to 4 amino acids, 1 to 3 amino acids, 1 to 2 amino acids, a single amino acid, etc.) or one or few amino acids in the above amino acid sequence.

In the context of the present invention, the expression "deficient in the function of expressing NAD kinase gene" is intended to mean that NAD kinase having inherent enzymatic functions is not expressed from the NAD kinase gene. Examples of such a state include not only those where no expression product is produced from the NAD kinase gene, but also those where an expression product (e.g., hnRNA, mRNA or protein) of this gene is expressed but loses its inherent normal functions. Such a functional deficiency in the NAD kinase gene may be caused by deletion, substitution and/or insertion of one or more nucleotides in the NAD kinase gene or its expression control region comprising a transcriptional regulatory region or a promoter region. It should be noted that there is no particular limitation on the site where the above deletion, substitution and/or insertion occurs or on the sequence to be deleted, substituted and/or inserted, as long as the normal functions of the NAD kinase gene can be lost. In a preferred embodiment, at least one of the gene sequences encoding the enzymatically active sites of NAD kinase is deleted.

Particularly in the case of being a eukaryotic organism, the microorganism of the present invention may have an effect in cases where the function of expressing the above NAD kinase is lost in at least one allele on the chromosome (heterozygote), but is preferably lost in both alleles (homozygote).

TABLE 1

| Species | Gene name | GenBank Accession No. of CDS/ the CDS position in chromosome or whole genome sequence |
|---|---|---|
| *Saccharomyces cerevisiae* | UTR1 | NM_001181707 (Saccharomyces Genome Database Accession No: YJR049C): SEQ ID NO: 1 |
| | YEF1 | NM_001178856: SEQ ID NO: 3 |
| *Schizosaccharomyces pombe* | SPCC24B10.02c | NM_001022996 |
| *Pichia stipitis* | NAD kinase | XM_001383120 |
| *Aspergillus oryzae* | NAD kinase | XM_001824067 |
| *Aspergillus niger* | NAD kinase | XM_001401229 |
| *Pichia angusta* | NAD kinase | Position 1304477-1306453 of whole genome sequence: AEOI_01000012 |

Moreover, the microorganism of the present invention may be deficient in the function of FPS1 gene, either alone or in addition to NAD kinase gene.

As used herein, the term "FPS1 gene" is not limited to a gene (Saccharomyces Genome Database Accession No: YLL043W, Genbank Accession No: NM_001181863.1, SEQ ID NO: 23) encoding a Saccharomyces cerevisiae-derived FPS1 protein (SEQ ID NO: 24), and may also be a gene encoding a protein which functions as a glycerol channel.

In one embodiment, the term "FPS1 gene" also encompasses a gene encoding the amino acid sequence shown in SEQ ID NO: 24 or a gene encoding an amino acid sequence with deletion, substitution or addition of one or more amino acids (e.g., 1 to 40 amino acids, 1 to 20 amino acids, 1 to 15 amino acids, 1 to 10 amino acids, 1 to 9 amino acids, 1 to 8 amino acids, 1 to 7 amino acids, 1 to 6 amino acids, 1 to 5 amino acids, 1 to 4 amino acids, 1 to 3 amino acids, 1 to 2 amino acids, a single amino acid, etc.) or one or few amino acids in the above amino acid sequence.

In the context of the present invention, the expression "deficient in the function of expressing FPS1 gene" is intended to mean that any FPS1 protein having inherent enzymatic functions is not expressed from the FPS1 gene. Examples of such a state include not only those where no expression product is produced from the FPS1 gene, but also those where an expression product (e.g., hnRNA, mRNA or protein) of this gene is expressed but loses its inherent functions as a glycerol channel. Such a functional deficiency in the FPS1 gene can be caused by deletion, substitution and/or insertion of one or more nucleotides in the FPS1 gene or its expression control region comprising a transcriptional regulatory region or a promoter region. It should be noted that there is no particular limitation on the site where the above deletion, substitution and/or insertion occurs or on the sequence to be deleted, substituted and/or inserted, as long as the functions of the FPS1 gene as a glycerol channel can be lost. In a preferred embodiment, at least one of the gene sequences encoding the active sites of the FPS1 protein is deleted.

Particularly in the case of being a eukaryotic organism, the microorganism of the present invention may have an effect in cases where the function of expressing the above FPS1 is lost in at least one allele on the chromosome (heterozygote), but is preferably lost in both alleles (homozygote).

2. Method for Preparing a Fermentative Microorganism Whose Xylose Fermentation Ability is Increased The present invention provides a method for preparing a fermentative microorganism whose xylose fermentation ability is increased by causing a deficiency in the function of expressing NAD kinase gene in a host microorganism.

Moreover, the above method may further comprise a step of causing a deficiency in the function of expressing FPS1 gene. Alternatively, without causing a deficiency in the function of expressing NAD kinase gene in a host microorganism, a fermentative microorganism whose xylose fermentation ability is increased can also be prepared by causing a deficiency only in the function of expressing FPS1 gene.

Techniques used to cause a deficiency in the function of expressing NAD kinase gene or FPS1 gene include knockout or knockdown techniques such as gene targeting or RNAi, etc.

(1) Gene Targeting

Gene targeting is a procedure for introducing a mutation into a specific gene on the chromosome by means of homologous recombination (Capeccchi, M. R. Science, 244, 1288-1292, 1989).

First, a targeting vector is constructed for use in causing a deficiency in the function of NAD kinase gene or FPS1 gene. For targeting vector construction, a genomic DNA library of a target microorganism is prepared. To ensure that the frequency of recombination is not reduced by polymorphism, etc., this genomic DNA library is preferably prepared from genomic DNAs derived from a microorganism of the same group as the target microorganism of gene targeting, preferably a microorganism of the same species. Such a library may be a commercially available one. Alternatively, the cDNA of NAD kinase or FPS1 or a partial sequence thereof may be used as a probe in screening to clone the DNA sequence of the genomic gene of NAD kinase or FPS1, or primers may be prepared based on the cDNA of NAD kinase or FPS1 or a partial sequence thereof to amplify the genomic NAD kinase gene or FPS1 gene by PCR. For details of how to prepare a genomic DNA library, reference may be made to the following: "Sambrook & Russell, Molecular Cloning: A Laboratory Manual Vol. 3, Cold Spring Harbor Laboratory Press 2001," "Ausubel, Current Protocols in Molecular Biology, John Wiley & Sons 1987-1997."

Next, the cloned genomic DNA is analyzed by sequencing, Southern blotting, restriction enzyme digestion or the like to identify the positions of exons (in the case of eukaryotic organisms) and restriction enzyme sites. Based on the sequence information thus analyzed, mutation-bearing sites and so on are determined.

In the present invention, mutations (deletion, substitution and/or insertion) to be introduced onto the chromosome are not limited in any way as long as the normal functions of NAD kinase gene or FPS1 gene are impaired, and these mutations may be located either in intron and/or exon regions of the NAD kinase gene or the FPS1 gene or in expression control regions of the NAD kinase gene or the FPS1 gene. The above mutations are preferably located in exon regions of the NAD kinase gene or the FPS1 gene, more preferably located to cause deletion of at least one exon in the NAD kinase gene or the FPS1 gene, and most preferably located to cause deletion of all exons. This is because such a mutation ensures functional impairment of the NAD kinase gene or the FPS1 gene.

The targeting vector may comprise not only homologous regions at the 3'- and 5'-sides of a mutation-bearing site (hereinafter referred to as 3'-arm and 5'-arm, respectively), but also a selection marker for use in recombinant selection. Examples of a selection marker include positive selection markers (e.g., neomycin resistance gene, hygromycin B phosphotransferase gene, kanamycin resistance gene), expression reporters for genes to be disrupted (e.g., LacZ, GFP (green fluorescence protein) and luciferase genes), negative selection markers (e.g., herpes simplex virus thymidine kinase gene (HSV-TK), diphtheria toxin A fragment (DTA)), etc. In particular, since the present invention uses a microorganism as a host, a gene for auxotrophic complementation, e.g., URA3 allows selection on a uracil-free agar medium, may also be used depending on the auxotrophy of the host. Likewise, the use of a drug resistance gene against cycloheximide (YAP1) allows selection on a cycloheximide-containing medium. Moreover, a sequence having such a selection marker inserted between 3'-arm and 5'-arm can be used to disrupt a target gene. The vector may comprise, at a position outside of each homologous region, an appropriate restriction enzyme cleavage site for linearization of the vector.

Figure 6:
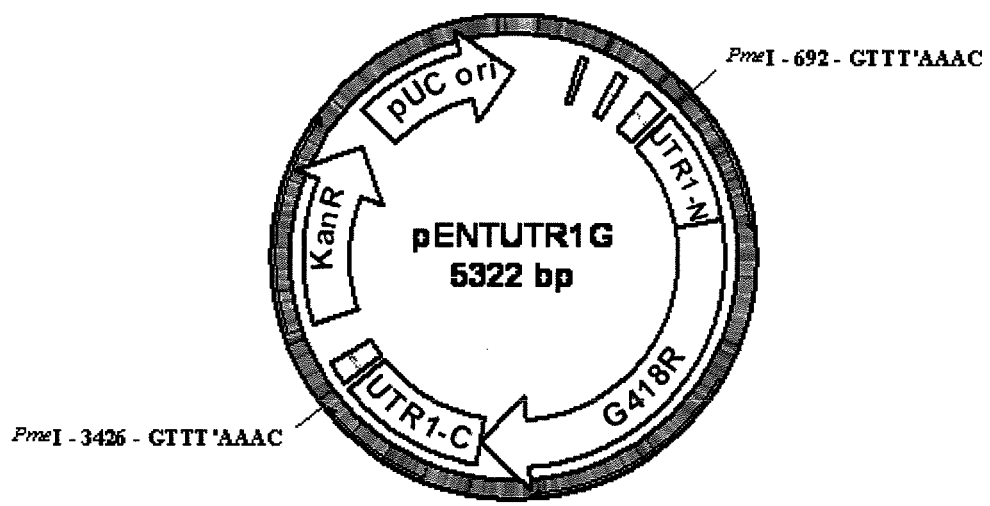
FIG. 6 shows a schematic view of plasmid pENTUTR1G used in the Example section.

FIG. 6 shows an example of the targeting vectors used in the Example section for knockout of *Saccharomyces cerevisiae* UTR1 gene. This construct is configured to comprise UTR1 genomic gene sequences encoding the N-terminal and C-terminal amino acid sequences of UTR1 protein as 5'-arm ("UTR1-N") and 3'-arm ("UTR1-C"), respectively, and geneticin resistance gene ("G418R") inserted as a positive selection marker between the 5'-arm and the 3'-arm.

This UTR1-N-G418R-UTR1-C fragment is excised from the vector with restriction enzymes, purified and then transformed into yeast cells to obtain a strain acquiring geneticin resistance by homologous recombination, followed by PCR to confirm UTR1 gene disruption.

Such a targeting vector can be constructed starting from a commercially available plasmid vector (e.g., pENTR/D-TOPO® (Invitrogen) or pBluescriptII (Stratagene)).

(2) RNA Interference

Other techniques to cause a deficiency in the function of expressing NAD kinase gene or FPS1 gene include RNA interference (RNAi) with siRNAs (small interfering RNAs), etc. RNAi is a multi-step process proceeding through a number of stages. First of all, double-stranded RNA (dsRNA) or hairpin-shaped shRNA (small hairpin RNA) expressed from an RNAi expression vector is recognized by Dicer and cleaved into siRNAs of 21 to 23 nucleotides. These siRNAs are then integrated into an RNAi targeting complex, which is called the RNA-induced silencing complex (RISC), and the complexes between RISC and siRNAs bind to target mRNA containing sequences complementary to the siRNA sequences and thereby cleave the mRNA. The target mRNA is cleaved in the center of its region complementary to the siRNA, finally leading to rapid degradation of the target mRNA and reduced protein expression levels. The most potent siRNA duplexes are known to be sequences of 21 nucleotides in length, each comprising a 19 bp duplex with an overhang of two uridine residues at the 3'-terminal end (Elbashir S. M. et al., Genes and Dev, 15, 188-200 (2001)).

Thus, to obtain a microorganism knocked down for NAD kinase gene or FPS1 gene, nucleotides covering a sequence complementary to a part of the NAD kinase gene as shown in Table 1 or a FPS1 gene sequence (e.g., but not limited to, SEQ ID NO: 23) are first inserted as dsRNA or shRNA in an expressible state into an appropriate RNAi expression vector to thereby prepare an RNAi vector. The above vector may then be introduced into host cells, followed by selection of transformants to thereby obtain a microorganism knocked down for NAD kinase gene or FPS1 gene.

Design and synthesis of dsRNA or shRNA may be accomplished by using a commercially available DNA/RNA synthesizer (e.g., Applied Biosystems model 394) or may be entrusted to a third party (e.g., TAKARA Bio).

A deficiency in the function of expressing NAD kinase gene or FPS1 gene can be confirmed as a reduction in the expression level of normal NAD kinase gene or normal FPS1 gene. The expression level of NAD kinase gene or FPS1 gene can be measured using an extract of the microorganism of the present invention by RT-PCR and agarose gel electrophoresis, Real-Time PCR, Northern blotting, microarray analysis, as well as mass spectrometry, etc. Primers or probes for use in these measurements may be designed and synthesized on the basis of the sequence of the NAD kinase gene or the FPS1 gene. Confirmation of whether an expression product of NAD gene is normal can be accomplished by sequence analysis of the expression product.

The microorganism of the present invention, which is characterized by being deficient in the function of expressing NAD kinase gene or FPS1 gene, may further have a xylose-metabolizing enzyme gene introduced in an expressible state. The term "xylose-metabolizing enzyme gene" is intended to mean a gene encoding a protein having the activity to catalyze any reaction among a series of chemical reactions for degrading xylose into ethanol (hereinafter referred to as "xylose-metabolizing activity") (such a protein is hereinafter referred to as a "xylose-metabolizing enzyme"). Examples of such a xylose-metabolizing enzyme gene include xylose reductase gene, xylitol dehydrogenase gene, and xylulose kinase gene.

Such a xylose-metabolizing enzyme gene may be, for example, derived from *Pichia stipitis, Saccharomyces cerevisiae, E. coli, Lactobacillus casei, Lactobacillus acidophilus, Aspergillus fumigatus, Staphylococcus aureus, Pichia pastoris, Schizosaccharomyces pombe*, etc.

The microorganism of the present invention is preferably transformed with at least one xylose-metabolizing enzyme gene selected from the group consisting of xylose reductase gene, xylitol dehydrogenase gene or xylulose kinase gene, and may be transformed with two or more of these genes or with all of the three genes.

Examples of xylose reductase gene, xylitol dehydrogenase gene or xylulose kinase gene include, but are not limited to, those listed below.

TABLE 2

| Xylose reductase genes | | | |
|---|---|---|---|
| Microorganism species | Gene name | GenBank Accession No. (chromosome or whole genome sequence) | GenBank Accession No. of CDS/the CDS position in chromosome or whole genome sequence |
| S. cerevisiae | GRE3 (YHR104W) | NC_001140 | NM_001179234.1 |
| Lactobacillus acidophilus | LBA1037 | NC_006814 | Position 1026933-1027815 of NC_006814 |
| Pichia pastoris | PAS_chr3_0744 | NC_012965 | XM_002492928.1 |
| Pichia stipitis | XYL1 | NC_009045 | X59465 |
| Schizosaccharomyces pombe | yak3 | NC_003424 | XM_001019927.1 |
| Aspergillus fumigatis | AFUA_1G04820 | NC_007194 | XM_745138.1 |

TABLE 3

Xylitol dehydrogenase genes

| Microorganism species | Gene name | GenBank Accession No. (chromosome or whole genome sequence) | GenBank Accession No. of CDS/the CDS position in chromosome or whole genome sequence |
|---|---|---|---|
| S. cerevisiae | XYL2 (YLR070C) | NC_001144 | NM_001181957.1 |
| S. cerevisiae | SOR1 (YJR159W) | NC_001142 | NM_001181817.1 |
| Aspergillus fumigatus | AFUA_1G16270 | NC_007194 | XM_747900.1 |
| Staphylococcus aureus | SAB0195 | NC_007622 | Position 243313-244338 of NC_007622 |
| Pichia stipitis | XYL2 | NC_009068 (SEQ ID NO: 11) | X55392 |

TABLE 4

Xylulose kinase genes

| Microorganism species | Gene name | GenBank Accession No. (chromosome or whole genome sequence) | GenBank Accession No. of CDS/the CDS position in chromosome or whole genome sequence |
|---|---|---|---|
| S. cerevisiae | XKS1 (YGR194C) | NC_001139 | Position 886078-887880 of NC_001139 |
| E. coli | ECBD0170 | NC_012947 | Position 181347-182801 of NC_012947 |
| Pichia stipitis | XKS1 | (SEQ ID NO: 13) | XM_001387288.1 |
| Staphylococcus aureus | xylB | NC_010999 | Position 397478-398944 of NC_010999 |

Xylose reductase is an enzyme catalyzing the following reaction during xylose degradation.

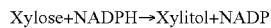
Xylose+NADPH→Xylitol+NADP

Xylitol dehydrogenase is an enzyme catalyzing the following reaction during xylose degradation.

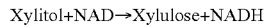
Xylitol+NAD→Xylulose+NADH

Xylulose kinase is an enzyme catalyzing the following reaction during xylose degradation.

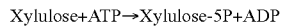
Xylulose+ATP→Xylulose-5P+ADP

In one embodiment, the xylose-metabolizing enzyme gene (e.g., xylose reductase, xylitol dehydrogenase or xylulose kinase) may be a mutant thereof as long as it encodes a protein having xylose-metabolizing activity. Examples of such a mutant include those having deletion, insertion, substitution or addition of one or more nucleotides in the nucleotide sequence of a polynucleotide encoding the above xylose-metabolizing enzyme protein. These mutants may be mutated in either or both of coding and non-coding regions. Mutations in coding regions may produce conservative or non-conservative amino acid deletions, insertions, substitutions and/or additions. As used herein, the term "xylose-metabolizing enzyme gene" also encompasses a gene (e.g., SEQ ID NO: 9, 11 or 13) encoding the amino acid sequence shown in SEQ ID NO: 10, 12 or 14 or a gene encoding an amino acid sequence with deletion, substitution or addition of one or more amino acids (e.g., 1 to 40 amino acids, 1 to 20 amino acids, 1 to 15 amino acids, 1 to 10 amino acids, 1 to 9 amino acids, 1 to 8 amino acids, 1 to 7 amino acids, 1 to 6 amino acids, 1 to 5 amino acids, 1 to 4 amino acids, 1 to 3 amino acids, 1 to 2 amino acids, a single amino acid, etc.) or one or few amino acids in the above amino acid sequence.

It is well known in the art that some amino acids in the amino acid sequence of a polypeptide can be easily modified without significantly affecting the structure or function of this polypeptide. In addition to artificial modifications, it is also well known that there are naturally occurring mutants of a protein, which do not significantly alter the structure or function of the protein.

Those skilled in the art would be able to easily modify one or more amino acids in the amino acid sequence of a polypeptide by using well-known techniques. For example, in accordance with known procedures for point mutagenesis, any nucleotide in a polynucleotide encoding a polypeptide can be modified. Moreover, primers corresponding to any site in a polynucleotide encoding a polypeptide may be designed and used to prepare a deletion mutant or an addition mutant. Further, when using the procedures described herein, it is possible to easily determine whether or not the prepared mutant enzymes have desired activity.

Preferred mutant enzymes have conservative or non-conservative amino acid substitutions, deletions or additions, preferably silent substitutions, additions and deletions, and particularly preferably conservative substitutions. These modifications do not alter the polypeptide activity intended in the present invention.

Typical examples of conservative substitutions are replacement of one amino acid with another amino acid, each being selected from aliphatic amino acids Ala, Val, Leu and Ile, interchange between hydroxyl residues Ser and Thr, interchange between acidic residues Asp and Glu, replacement between amide residues Asn and Gln, interchange between basic residues Lys and Arg, as well as replacement between aromatic residues Phe and Tyr.

As described in detail above, further guidance as to which amino acid change is likely to be phenotypically silent (i.e., likely to have no significantly adverse effect on functions) can be found in Bowie, J. U. et al., "Deciphering the Message in Protein Sequences: Tolerance to Amino Acid Substitutions," Science 247:1306-1310 (1990), which is incorporated herein by reference.

With the use of the above polynucleotides according to the present invention, polypeptides having xylose-metabolizing enzyme activity can be synthesized in transformants or cells.

The xylose-metabolizing enzyme gene is preferably introduced in a state of being integrated into an expression vector expressible in host cells. Such an expression vector may comprise the following elements (i) to (iii):
(i) a promoter transcribable in host cells;
(ii) the xylose-metabolizing enzyme gene ligated to the promoter; and
(iii) an expression cassette comprising, as constituent elements, signals that function in the host cells for transcription termination and polyadenylation of an RNA molecule.

Examples of such a vector include pYE22m (for yeast: Biosci. Biotech. Biochem., 59, 1221-1228, 1995), YCp50 (for yeast: X70276), YIp1 (for yeast: X70480), etc.

Any combination of promoter/terminator may be used for regulating gene expression in host cells, as long as it functions in the host cells. For example, promoters available for use in yeast include, but are not limited to, TDH3p, PYK1p, PGK1p, TPI1p, GAL1p, GAL10p, ADH2p, PHO5p, CUP1p, MF(ALPHA)1p, etc. As a promoter for constitutively high expression, it is possible to use a promoter such as TDH3p, TPI1p, PGK1p, PGI1p, PYK1p, ADH1p, etc.

Selection markers available for use in transformation include auxotrophic markers (URA3, LEU2), drug resistance markers (hygromycin resistance, geneticin resistance), copper resistance gene (CUP1) (Marin et al., Proc. Natl. Acad. Sci. USA, 81, 337 1984), cerulenin resistance gene (fas2m, PDR4) (Junji Inokoshi et al., Biochemistry, vol. 64, p. 660, 1992; Hussain et al., gene, 101, 149, 1991) and so on.

For transformation of host cells, commonly used known techniques can be used. For example, in the case of prokaryotic organisms, electroporation (Mackenxie D. A. et al. Appl. Environ. Microbiol., 66, 4655-4661, 2000) or heat shock method may be used for transformation. Likewise, in the case of yeast, transformation may be accomplished by, but is not limited to, electroporation, spheroplast method (Proc. Natl. Acad. Sci. USA, 75 p1929 (1978)), lithium acetate method (J. Bacteriology, 153, p163 (1983)), Proc. Natl. Acad. Sci. USA, 75 p1929 (1978), and other methods as described in Methods in yeast genetics, 2000 Edition: A Cold Spring Harbor Laboratory Course Manual.

In addition, as for standard cloning techniques, reference may be made to "Sambrook & Russell, Molecular Cloning: A Laboratory Manual Vol. 3, Cold Spring Harbor Laboratory Press 2001," "Methods in Yeast Genetics, A laboratory manual (Cold Spring Harbor Laboratory Press, Cold Spring Harbor, N.Y.)," etc.

3. Method for Producing Ethanol

The microorganism of the present invention prepared as above has increased xylose fermentation ability in comparison with a wild-type microorganism of the same species. As used herein, the term "xylose fermentation" is intended to mean that ethanol is produced by assimilation of xylose. Namely, xylose fermentation refers to ethanol fermentation from xylose. Ethanol fermentation refers to a reaction in which ethanol is produced through the fermentation process.

Thus, when cultured in the presence of xylose-containing raw materials, the microorganism of the present invention shows reduced production of by-products, i.e., xylitol and glycerol, in comparison with a wild-type microorganism of the same species which is cultured under the same conditions. As a consequence, more ethanol is produced by the microorganism of the present invention.

Based on this finding, the present invention provides, in another embodiment, a method for producing ethanol, which comprises a step of contacting the microorganism of the present invention with xylose-containing raw materials.

The step of contacting the microorganism of the present invention with xylose-containing materials may be accomplished by mixing the microorganism of the present invention with xylose-containing materials. Preferably, the microorganism of the present invention is contacted in an active state with xylose-containing materials.

Examples of techniques for contacting the microorganism of the present invention in an active state with xylose-containing materials include those for culturing the microorganism of the present invention under culture conditions allowing the microorganism of the present invention to grow and in the presence of xylose-containing raw materials. Such culture conditions will vary depending on the species of microorganism. For example, in the case of yeast, culture may be accomplished at 30° C. in an appropriate medium, e.g., YPD medium (10 g/L yeast extract, 20 g/L polypeptone, 20 g/L glucose), SX medium (50 g/l xylose, 6.7 g/l yeast nitrogen base free from amino acids, 20 mg/l adenine, 20 mg/l histidine, 100 mg/l leucine, 20 mg/l tryptophan), which is supplemented with xylose-containing raw materials.

Alternatively, prior to culture in the presence of xylose-containing raw materials, the microorganism of the present invention may be cultured to increase the number of microbial cells under culture conditions allowing the microorganism of the present invention to grow, followed by fermentation with the microorganism of the present invention in the presence of xylose-containing raw materials.

However, culture conditions are not limited to those mentioned above. Those skilled in the art would be able to select suitable culture conditions as appropriate for the species of microorganism and to actually culture the microorganism.

The xylose fermentation ability can be confirmed by contacting the microorganism of the present invention with xylose-containing raw materials and, after passing a certain period of time, measuring ethanol production level in the system.

Moreover, the xylose fermentation ability can also be measured as the yield of ethanol relative to xylose assimilation level. The yield of ethanol relative to xylose assimilation level can be calculated as follows.

First, the production of ethanol ($C_2H_5OH$) from xylose ($C_5H_{10}O_5$) is represented by the following reaction scheme.

$$6C_5H_{10}O_5 \rightarrow 10C_2H_5OH + 10CO_2 + 10ATP$$

Based on this reaction scheme as well as xylose molecular weight (150) and ethanol molecular weight (46), the relationship represented by the following equation can be established between xylose assimilation level and ethanol production level.

Ethanol production level=xylose assimilation level×{(10×46)/(6×150)}

Thus, the case where ethanol is produced in an amount of "xylose assimilation level×{(10×46)/(6×150)}=xylose assimilation level×0.51" can be set to 100% ethanol yield.

Xylose assimilation level and ethanol production level can be easily determined when the fermentation system containing the microorganism of the present invention and xylose-containing raw materials is analyzed for ingredients by known analysis procedures such as high performance liquid chromatography, etc.

"Xylose-containing raw materials" are not limited in any way as long as they are raw materials containing xylose. Preferred are raw materials derived from xylose-containing organisms, i.e., "xylose-containing biomass." Biomass is defined as "renewable, organism-derived organic resources, excluding fossil resources" in the "Biomass Nippon Strategy" published by the Japanese Ministry of Agriculture, Forestry and Fisheries.

Accordingly, based on this definition, the term "xylose-containing biomass" can be defined as "renewable, organism-derived organic resources containing xylose, excluding fossil resources."

Specific examples of xylose-containing biomass include, but are not limited to, non-edible parts of sugar cane, maize, beet, potato, sweet potato, wheat, kaoliang (Sorghum), sorghum and so on, as well as scrap wood, pulp spent liquor, bagasse, chaff, corncob, rice straw, switchgrass, Erianthus, napier grass, etc.

EXAMPLES

The present invention will be further described in more detail by way of the following illustrative examples, although the present invention is not limited to the embodiments disclosed herein.

Test Methods:

The test items and test methods used in the following examples are shown below. Unless otherwise specified, the test methods in the examples illustrated below were in accordance with the following.

<Obtaining of UTR1 and YEF1 Genes>

Figure 2:
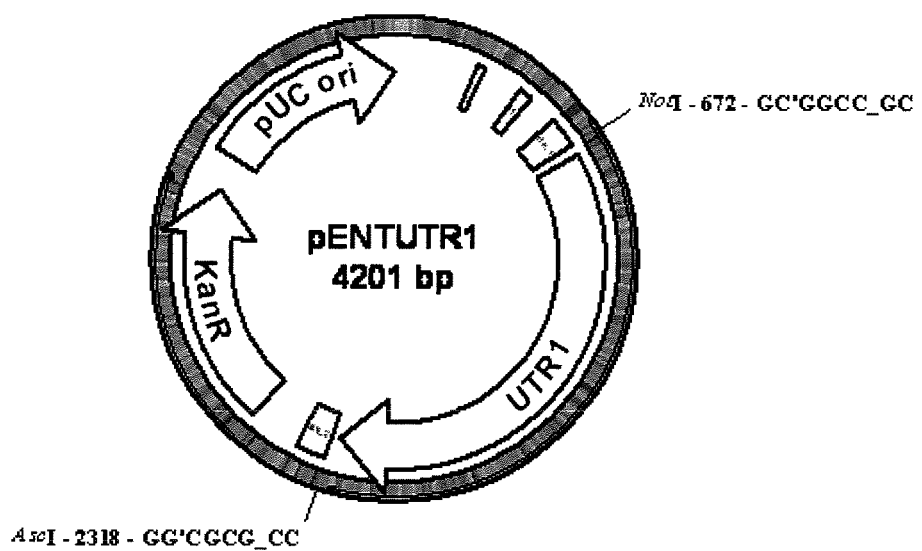
FIG. 2 shows a schematic view of plasmid pENTUTR1 used in the Example section.
Figure 3:
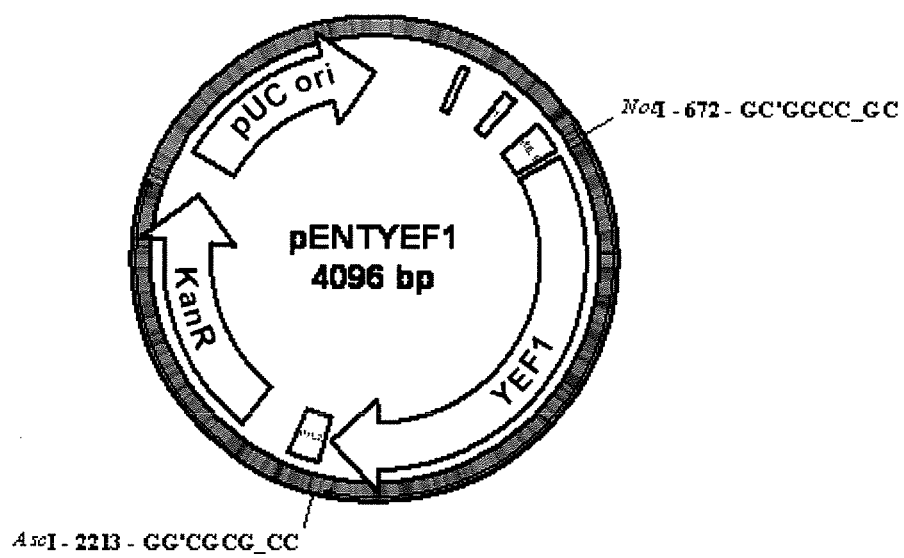
FIG. 3 shows a schematic view of plasmid pENTYEF1 used in the Example section.

Yeast Saccharomyces cerevisiae UTR1 gene has already been cloned and its nucleotide sequence has been reported (Saccharomyces Genome Database Accession No. YJR049C). Likewise, yeast Saccharomyces cerevisiae YEF1 gene has also already been cloned and its nucleotide sequence has been registered in the Genbank (Genbank Accession No. NM_001178856). Thus, the UTR1 gene (genome sequence: SEQ ID NO: 1) and the YEF1 gene (genome sequence: SEQ ID NO: 3) can be obtained based on their nucleotide sequence information by being PCR amplified and isolated using, as PCR templates, chromosomal DNAs prepared from yeast Saccharomyces cerevisiae having the respective genes. More specifically, in this case, chromosomal DNAs of yeast Saccharomyces cerevisiae X2180-1A (ATCC26786) (MATa SUC2 mal mel gal2 CUP1) were used as templates in PCR with primers UTR1F1 and UTR1R1 to obtain UTR1 and with primers YEF1F1 and YEF1R1 to obtain YEF1. Using Invitrogen pENTR™ Directional TOPO Cloning Kits, the obtained DNA fragments were each inserted into a vector, pENTR™/D-TOPO®, to thereby obtain plasmid pENTUTR1 (FIG. 2) or pENTYEF1 (FIG. 3). The inserted genes were both confirmed for their sequences by DNA sequencing. The chromosomal DNAs used for obtaining both genes are not limited to the strain mentioned above and may be prepared from any yeast strain as long as it belongs to Saccharomyces cerevisiae. PCR amplification of the target genes from chromosomal DNAs and the subsequent isolation thereof, including preparation of PCR primers, may be accomplished in a manner well known to those skilled in the art.

UTR1F1:
(SEQ ID NO: 5)
5' CACCGTTTAAACTCTAGAATGAAGGAGAATGACATGAATAAT 3'

UTR1R1:
(SEQ ID NO: 6)
5' GTTTAAACGGATCCTTATACTGAAAACCTTGCTTGAGA 3'

YEF1F1:
(SEQ ID NO: 7)
5' CACCGTTTAAACTCTAGAATGAAAACTGATAGATTACTGATTA 3'

YEF1R1:
(SEQ ID NO: 8)
5' GTTTAAACGAGCTCTTAGATTGCAAAATGAGCCTGAC 3'

<Procedures for Preparation of Template DNA for PCR>

Yeast cells were suspended in 50 µl of Lysis buffer (0.125 mg/ml zymolyase 100T, 1 M sorbitol, 40 mM potassium phosphate buffer pH 6.8, 1 mM dithiothreitol). After incubation at 30° C. for 1 hour, 5 µl of protease E (1 mg/ml) was added and the suspension was further incubated at 55° C. for 20 minutes and at 99° C. for 10 minutes. The suspension was centrifuged at 15,000 rpm for 10 minutes and the resulting supernatant was used as template DNA.

<Unit Preparation for UTR1 or YEF1 Gene Disruption>

Figure 4:
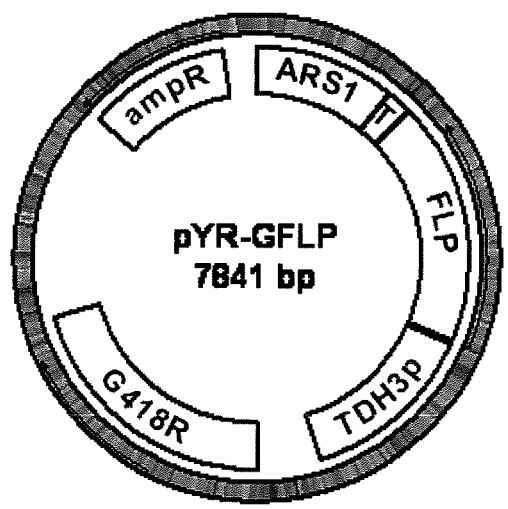
FIG. 4 shows a schematic view of plasmid pYRGFLP used in the Example section.
Figure 5:
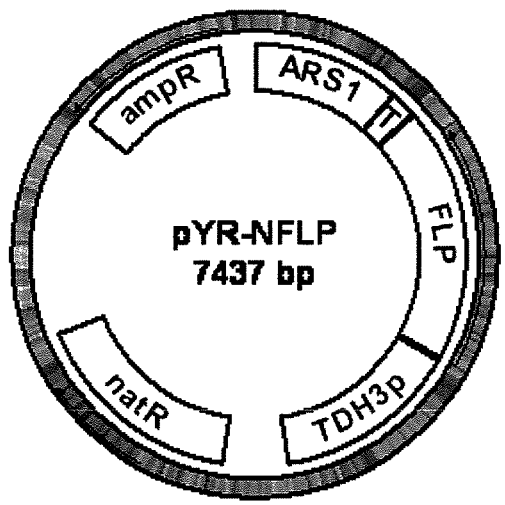
FIG. 5 shows a schematic view of plasmid pYRNFLP used in the Example section.
Figure 7:
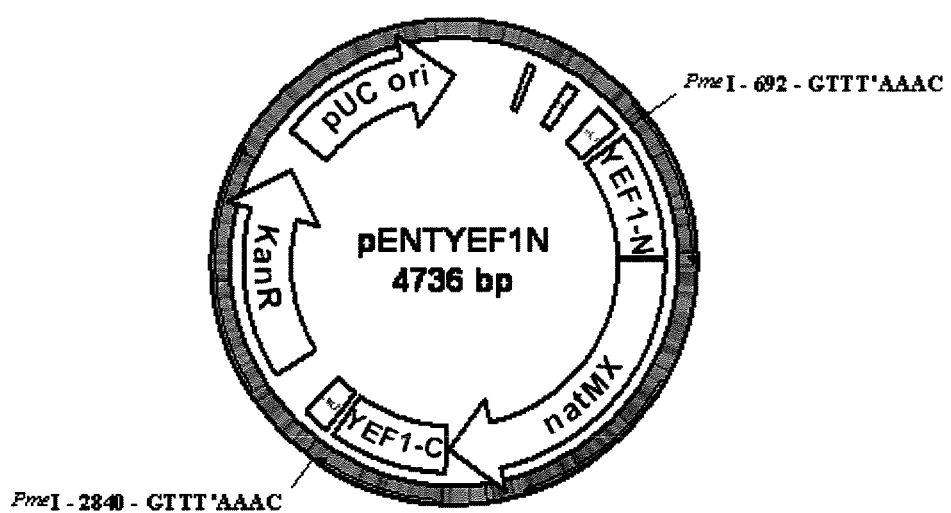
FIG. 7 shows a schematic view of plasmid pENTYEF1N used in the Example section.

For UTR1 gene disruption, the UTR1 gene in pENTUTR1 was cleaved with BsaAI and FspI, into which G418 resistance marker gene (PGK1p::KanMX) excised with PmeI from plasmid pYRGFLP (FIG. 4) was then inserted to obtain plasmid pENTUTR1G (FIG. 6). For YEF1 gene disruption, the YEF1 gene in pENYEF1 was cleaved with BstEII and StuI, into which Nat resistance marker gene (TEF1p::NatMX) excised with PmeI from plasmid pYRN-FLP (FIG. 5) was then inserted to obtain plasmid pENTYEF1N (FIG. 7). This pENTUTR1G or pENTYEF1N was cleaved with PmeI and electrophoresed on an agarose gel, followed by excising a DNA fragment of approximately 3.3 kbp (having N-terminal and C-terminal partial sequences from UTR1 and comprising G418 resistance marker gene (PGK1p::KanMX) in the center) or a DNA fragment of approximately 2.1 kbp (having N-terminal and C-terminal partial sequences from YEF1 and comprising Nat resistance marker gene (TEF1p::NatMX) in the center) from the agarose gel. These DNA fragments were purified and extracted from the gel. Their purification and extraction were accomplished by using an Illustra™ GFX™ PCR DNA and Gel Band Purification kit in accordance with the instruction manual.

<Yeast Strains>

In the present invention, S. cerevisiae strain X2180-1A was used for obtaining of UTR1, while S. cerevisiae strains HH1467, 468, 472 and 473 were used for breeding of UTR1 disruptants. For breeding of YEF1 disruptants, S. cerevisiae strain HH472 was used. In all strains used for the above purposes, expression units for P. stipitis xylose reductase gene (XYL1; SEQ ID NO: 9), P. stipitis xylitol dehydrogenase gene (XYL2; SEQ ID NO: 11) and S. cerevisiae xylulose kinase gene (XKS1; SEQ ID NO: 13) were integrated into certain regions in the chromosome under the control of promoters as shown for their genotypes, without being limited thereto.

(1) S. cerevisiae X2180-1A (ATCC26786) (MATa SUC2 mal mel gal2 CUP1)

(2) S. cerevisiae HH467 (MATa leu2-3,112 trp1-1 his3-11, 15 ade2-1 can1-100 rad5-535 ura3-1::URA3::TDH3p::XYL1::TDH3p::XYL2::TDH3p::XKS1)

(3) *S. cerevisiae* HH468 (MATa ade1 MAL61 MAL62 MAL63 AGT1 MAL12 MAL31 MAL32 ura3::URA3:: TDH3p::XYL1::TDH3p::XYL2::TDH3p::XKS1)

(4) *S. cerevisiae* HH472 (MATa SUC2 mal mel gal2 CUP1 GAT1::TDH3p::XYL1::PYK1p::XYL2::TPI1p::XKS1)

(5) *S. cerevisiae* HH473 (MATa SUC2 mal mel gal2 CUP1 YCT1::TDH3p::XYL1::PYK1p::XYL2::TPI1p::XKS1)

(6) *S. cerevisiae* CB11 (Berkley Stock Center) (MATa ade1 MAL61 MAL62 MAL63 AGT1 MAL12 MAL31 MAL32)

(7) *S. cerevisiae* W303-1A (BY4848) (MATa ura3-1 leu2-3,112 trp1-1 his3-11, 15 ade2-1 can1-100 rad5-535)

Among the above strains, (6) is the parent strain of HH468 and (7) is the parent strain of HH467, both of which are commercially available ((6): deposited under FERM BP-4198 with the Fermentation Research Institute, the Agency of Industrial Science and Technology, (7): NBRP ID No. BY4848). Likewise, (1) is the parent strain of HH472 and HH473 and is commercially available (ATCC ID No. ATCC26786). The respective strains are shown along with their genotypes.

<Breeding of UTR1 or YEF1 Gene Disruptants>

HH467, 468, 472 and 473 were transformed with the prepared DNA fragment of approximately 3.3 kbp (having N-terminal and C-terminal partial sequences from UTR1 and comprising geneticin resistance gene (PGK1p::KanMX) in the center) or of approximately 2.1 kbp (having N-terminal and C-terminal partial sequences from YEF1 and comprising Nat resistance marker gene (TEF1p::NatMX) in the center), and then applied onto a 300 μg/ml geneticin-containing YPD (10 g/L yeast extract, 20 g/L polypeptone, 20 g/L glucose* (added after being sterilized by filtration*)) medium for UTR1 disruptants or applied onto a 50 μg/ml clonNAT (nourseothricin dihydrogen sulfate)-containing YPD (10 g/L yeast extract, 20 g/L polypeptone, 20 g/L glucose* (added after being sterilized by filtration*)) medium for YEF1 disruptants. Some of the grown colonies were subjected to PCR with primers upUTR1_F1 and pPGK657-r1 or with primers downUTR1_R and G418_F1 for UTR1 disruptants to verify fragment amplification, thereby confirming that the UTR1 gene was disrupted. For YEF1 disruptants, PCR was performed with primers YEF1U_F and natMX-r2 or with primers YEF1D_R and natMX-f2 to verify fragment amplification, thereby confirming that the YEF1 gene was disrupted. Further, the transformants were applied onto YPGly (10 g/L yeast extract, 20 g/L polypeptone, 20 g/L glycerol) medium to verify their growth, thereby confirming that they were not respiratory deficient strains. In the embodiments illustrated here, the geneticin resistance or clonNAT resistance marker gene is used as a marker, although other markers may also be used depending on the genotype of host. When using a gene for complementation of the host's auxotrophy, e.g., URA3, selection can be conducted on a uracil-free agar medium. Alternatively, when using YAP1, a drug resistance gene against cycloheximide, selection can be conducted on a cycloheximide-containing YPD medium.

```
                                        (SEQ ID NO: 15)
upUTR1_F1:      5' CTACGCAAAGAGAACGGAG 3'

(SEQ ID NO: 16)
pPGK657-r1:     5' GCAATCAATAGGAAGACAGG 3'

(SEQ ID NO: 17)
downUTR1_R:     5' ATGTCACGCTTACATTCACG 3'

(SEQ ID NO: 18)
G418_F1:        5' TGGTTGTAACACTGGCAGAG 3'

(SEQ ID NO: 19)
YEF1U_F:        5' AGCGTTGTGAAAGGGAAATG 3'

(SEQ ID NO: 20)
natMX-r2:       5' GTGTCGTCAAGAGTGGTACC 3'

(SEQ ID NO: 21)
YEF1D_R:        5' TCTTCGACACTGCAAACGAC 3'

(SEQ ID NO: 22)
natMX-f2:       5' TCTACATGAGCATGCCCTGC 3'
```

<Xylose Fermentation Test on a Small Scale>

In this xylose fermentation test, the fermentation test medium used was YPX (10 g/L yeast extract, 20 g/L polypeptone, 50 g/L xylose* (added after being sterilized separately*)) or CSLX (0.5% corn steep liquor, 5 g/L urea, 1 mg/L pyridoxal hydrochloride, 1 mg/L thiamine hydrochloride, 0.1 mg/L biotin, 10 mg/L pantothenic acid**, 1 mg/L magnesium sulfate, 2 mg/L zinc sulfate, 50 g/L xylose*, pH 5.0 (added after being sterilized by filtration**, added after being sterilized separately*)). Yeast provided for the fermentation experiment was cultured as follows. A loopful of test yeast was inoculated into YPD (10 ml) and cultured in an incubator at 30° C. for 20 hours under shaking conditions. From the cultured solution, the yeast cells were collected and then suspended in fresh YPD (20 ml) and cultured at 30° C. for 3 hours under shaking conditions. The yeast cells were collected and washed twice with the medium to be used for the fermentation test, and then inoculated into 2 ml of the medium at $OD_{600}$=20 or $OD_{600}$=25. The suspension was transferred to a microtube of 3 ml volume and capped, followed by incubation at 30° C. Aliquots were sampled as appropriate, centrifuged and filtered, followed by high performance liquid chromatography to analyze their ingredients.

<Xylose Fermentation Test on a Large Scale>

In this fermentation test using a medium bottle of 100 ml volume, a silicon tube of 4 mm inner diameter was inserted through the cap of the bottle. The length of the tube was adjusted such that the tube was not immersed in the medium. The tube was equipped with a check valve through which gases would escape when the internal pressure was elevated, whereby the pressure would be able to be adjusted to the same level as the external pressure. Yeast provided for the fermentation test was cultured as follows. A loopful of test yeast was inoculated into YPD (10 ml) and cultured in an incubator at 30° C. for 20 hours under shaking conditions. The cultured solution was inoculated in its entirety into YPD (100 ml) in a 300 ml Erlenmeyer flask and cultured in an incubator at 30° C. for 20 hours under shaking conditions, followed by centrifugation to collect all the yeast cells. The yeast cells were suspended again in YPD (200 ml) in a 500 ml Erlenmeyer flask and cultured at 30° C. for 6 hours under shaking conditions. The yeast cells were collected and washed twice with the medium to be used for the fermentation test, and then inoculated into 45 ml of the medium at $OD_{600}$=20. The medium bottle was soaked in a water bath until reaching the depth of the medium and was kept at a temperature of 30° C. to effect fermentation while stirring at a rate of 60 rpm with a sterile stirrer bar. 1 ml aliquots of the fermented mash were sampled as appropriate, centrifuged and filtered, followed by high performance liquid chromatography to analyze their ingredients.

<Xylose Fermentation Test in Serial Batch Fermentation Mode>

Yeast from the fermentation test conducted on a 45 ml scale was collected by centrifugation, inoculated into 10 ml of CSLX medium at $OD_{600}$=100 and then transferred to a capped sterile plastic tube of 50 ml volume to effect fermentation at 30° C. After 48 hours, 1 ml of the fermented mash was sampled, centrifuged and filtered, followed by high performance liquid chromatography to analyze its ingredients. The remainder of the yeast was collected in its entirety and used for the next round of fermentation to conduct a fermentation test in the same manner.

<Measurement of Ethanol, Xylose, Glycerol and Xylitol>

From the fermented mash, aliquots were sampled as appropriate, centrifuged and filtered. The supernatants were each quantified by high performance liquid chromatography under the conditions shown below. The concentrations of ingredients in the test samples were calculated from the peak areas of their respective pure samples at known concentrations.

(1) Separation Column and Conditions
Column: Shodex SUGAR SH-G (6.0×50 mm)+SH1011 (8.0×300 mm)
Eluent: 5 mM $H_2SO_4$
Flow rate: 0.6 ml/min
Column oven: 60° C.
Detector: diode array detector (DAD) 280 nm (for furfurals) differential refractive index detector (RI) (for other sugars)

(2) System Configuration
HPLC main unit: Hitachi L-2000 series
Pump: L-2130
Autosampler: L-2200
DAD detector: L-2450
RI detector: L-2490
Column oven: Shimadzu CTO-10A Example 1

Xylose Fermentation Test on UTR1 Disruptants in YPX Medium (1)

Figure 8:
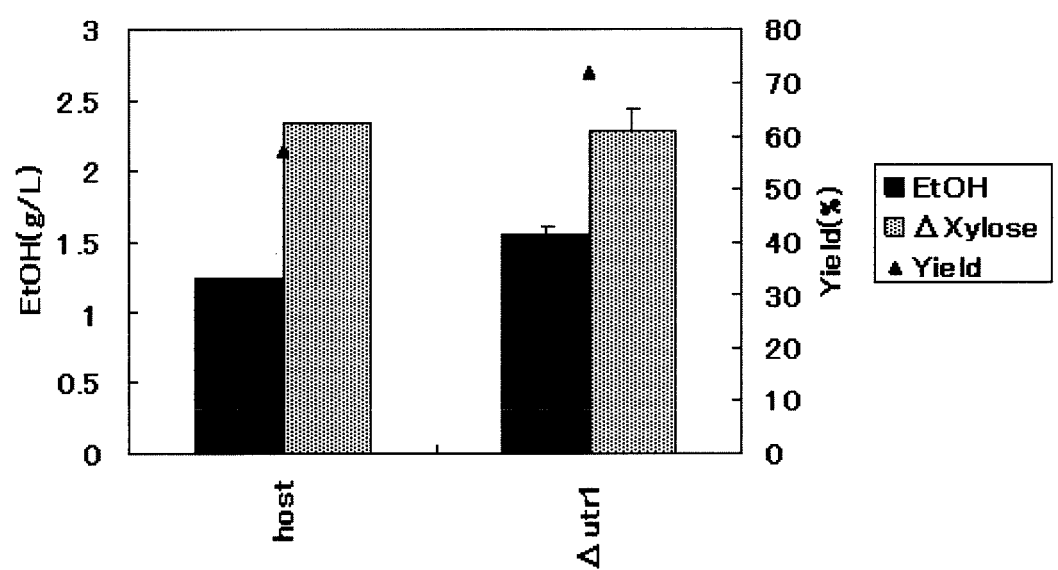
FIG. 8 shows the results of xylose fermentation test using the microorganism of the present invention (medium: YPX, host: HH473). In the figure, "ΔXylose" denotes a decrement in xylose level, while "Δutr1" denotes "UTR1 gene disruption."
Figure 9:
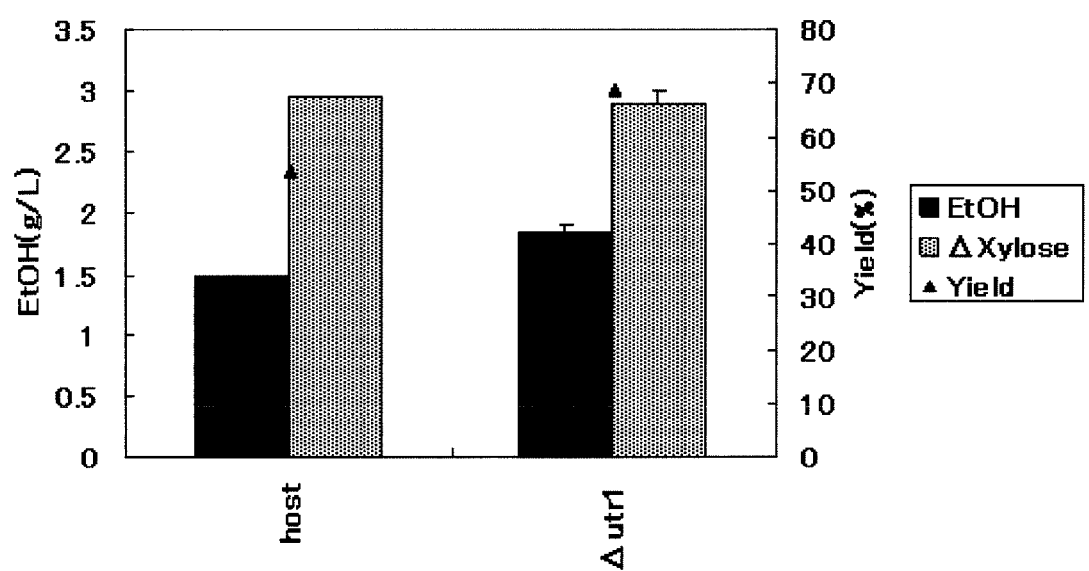
FIG. 9 shows the results of xylose fermentation test using the microorganism of the present invention (medium: YPX, host: HH468). In the figure, "ΔXylose" denotes a decrement in xylose level, while "Δutr1" denotes "UTR1 gene disruption."

HH467 and HH468 were used as hosts to breed UTR1 disruptants. For each case, the parent strain (n=1) and three bred strains (n=2) were each cultured in YPD as described in the test methods, inoculated into YPX medium (2 ml) at $OD_{600}$=20, and then transferred to a microtube to conduct a fermentation test at 30° C. under static conditions. After 24 hours, the yeast cells were separated by centrifugation and the supernatant was quantified for ethanol and xylose by high performance liquid chromatography. The yield of ethanol was expressed as a percentage, assuming that ethanol production in an amount of xylose assimilation level×0.51 was set to 100% yield. The results obtained are shown in FIGS. 8 and 9. In either case of using HH467 or HH468 as a host, the UTR1 disruptants showed an increase in the yield of ethanol produced from xylose when compared to their parent strains. Moreover, their xylose assimilation levels were almost the same as those of their parent strains. It can be confirmed that UTR1 disruption is effective in increasing the yield of ethanol produced from xylose.

Example 2

Xylose Fermentation Test on UTR1 Disruptants in YPX Medium (2)

Figure 10:
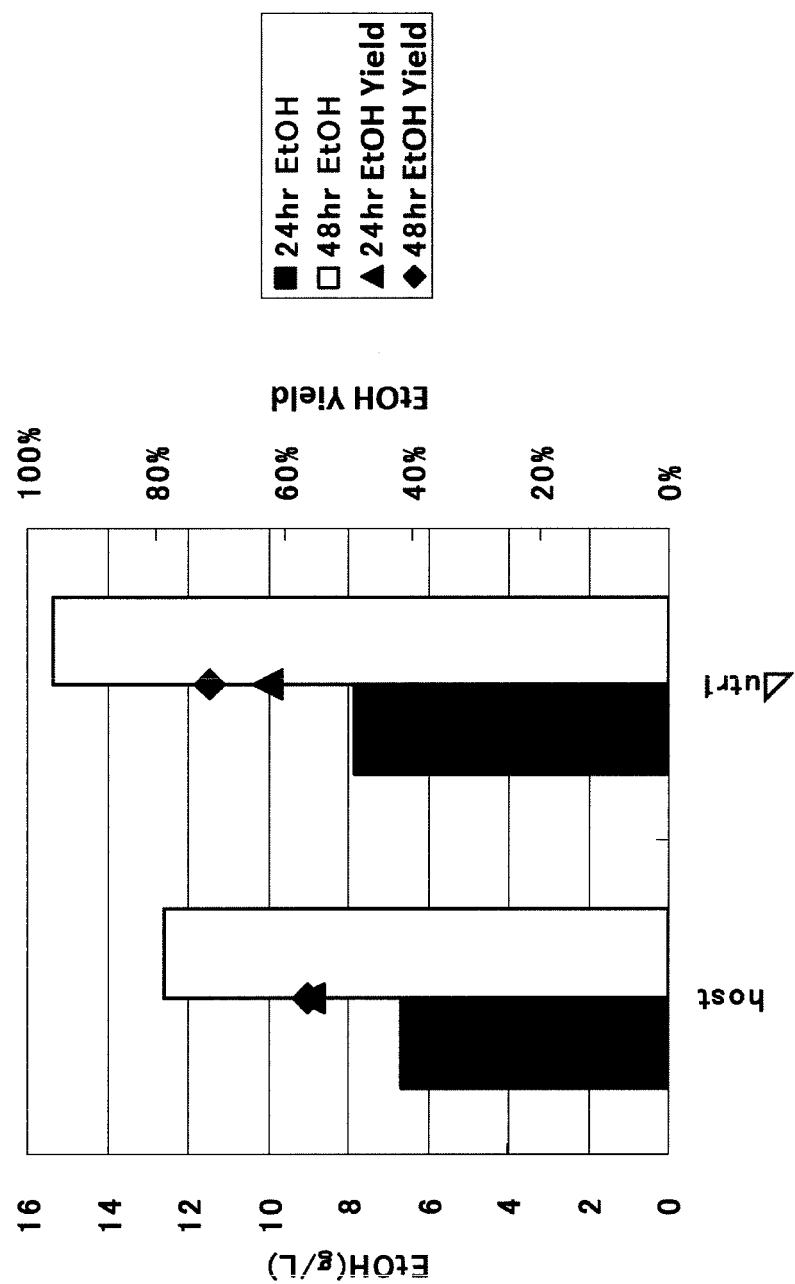
FIG. 10 shows the results of xylose fermentation test using the microorganism of the present invention (medium: YPX, host: HH473). In the figure, "Δutr1" denotes "UTR1 gene disruption."
Figure 11:
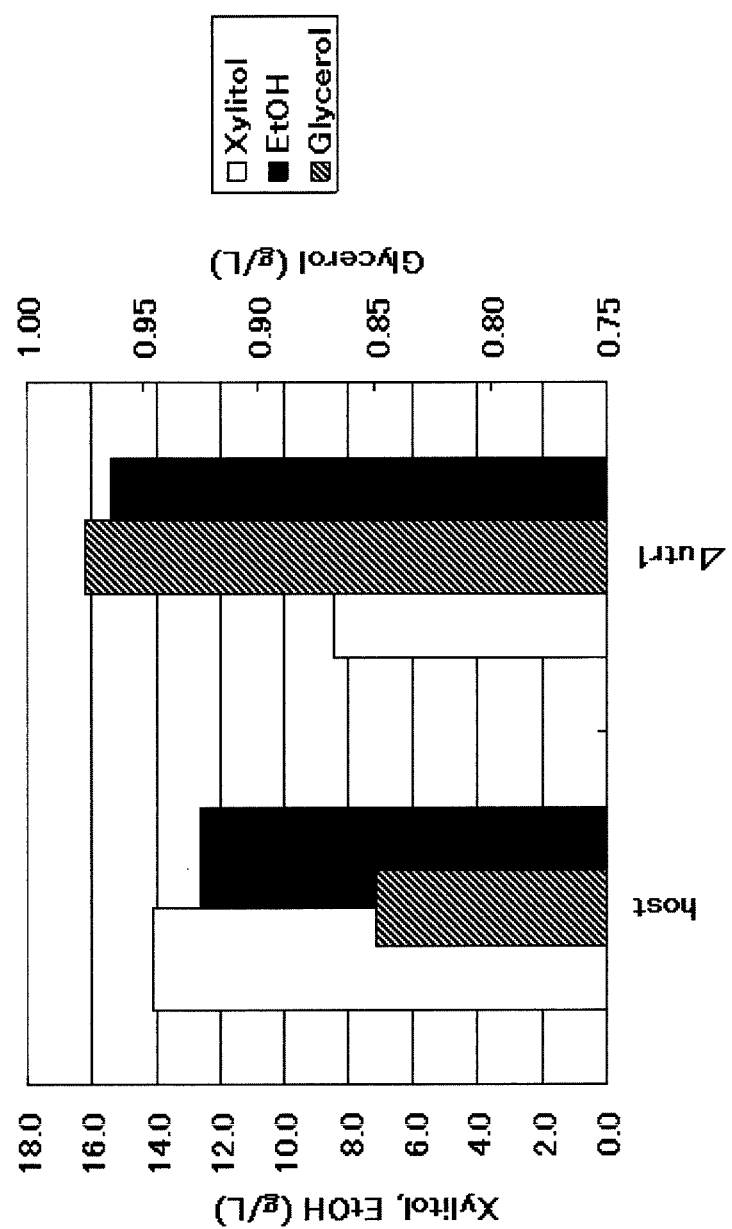
FIG. 11 shows the results of xylose fermentation test using the microorganism of the present invention (medium: YPX, host: HH473, measured after 48 hours). In the figure, "Δutr1" denotes "UTR1 gene disruption."

HH473 was used as a host to breed a UTR1 disruptant. The strain HH473 is a strain bred from X2180-1A and is not auxotrophic unlike HH467 and HH468. For each case, one strain was cultured in YPD as described in the test methods, inoculated into YPX medium (2 ml) at $OD_{600}$=25, and then transferred to a microtube to conduct a fermentation test at 30° C. under static conditions. After 24 or 48 hours, the yeast cells were separated by centrifugation and the supernatant was quantified for ethanol and xylose by high performance liquid chromatography. The yield of ethanol was expressed as a percentage, assuming that ethanol production in an amount of xylose assimilation level×0.51 was set to 100% yield. The results obtained are shown in FIG. 10. Even in the case of HH473 which is not auxotrophic for amino acids, the UTR1 disruptant showed an increase in the yield of ethanol produced from xylose when compared to its parent strain. The levels of by-products, i.e., xylitol and glycerol measured after 48 hours are also shown along with ethanol (FIG. 11). In the UTR1 disruptant, xylitol production level was significantly lower than in the parent strain.

Next, the strain HH472 was used as a host to obtain a UTR1 disruptant. The strain HH472 differs from the strain HH473 in the region where the expression cassette TDH3p::XYL1::PYK1p::XYL2::TPI1p::XKS1 is inserted.

Figure 12:
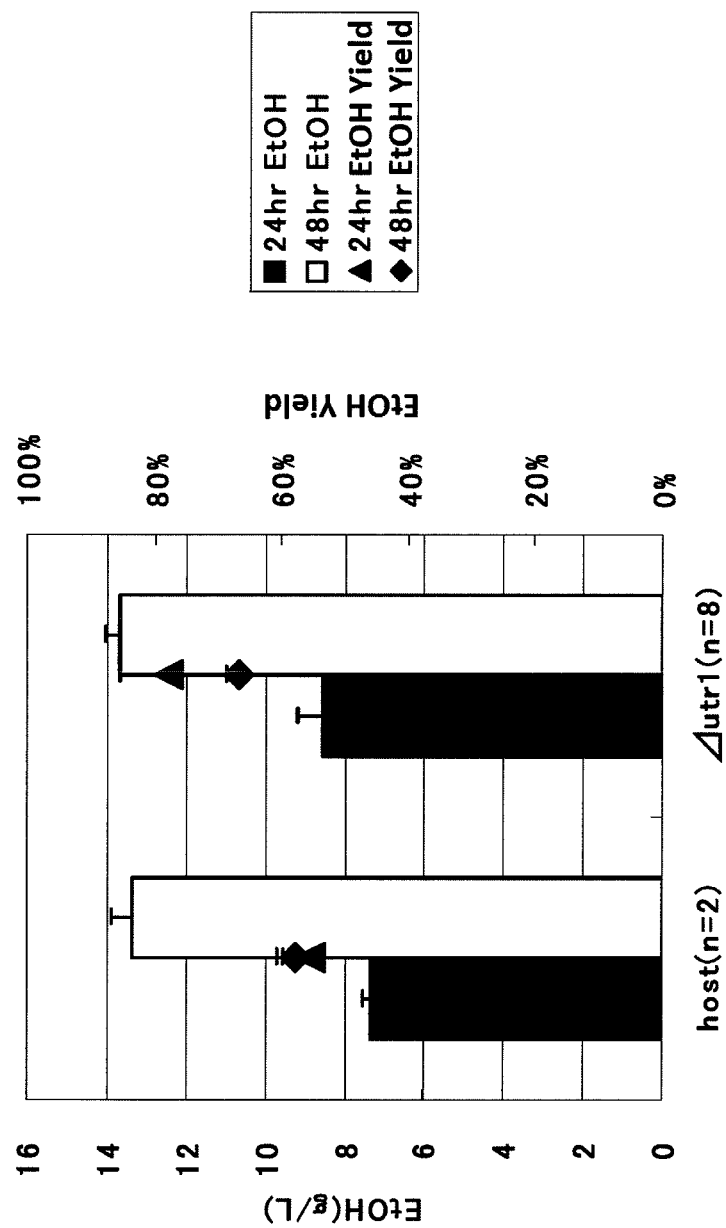
FIG. 12 shows the results of xylose fermentation test using the microorganism of the present invention (medium: YPX, host: HH472). In the figure, "Δutr1" denotes "UTR1 gene disruption."
Figure 13:
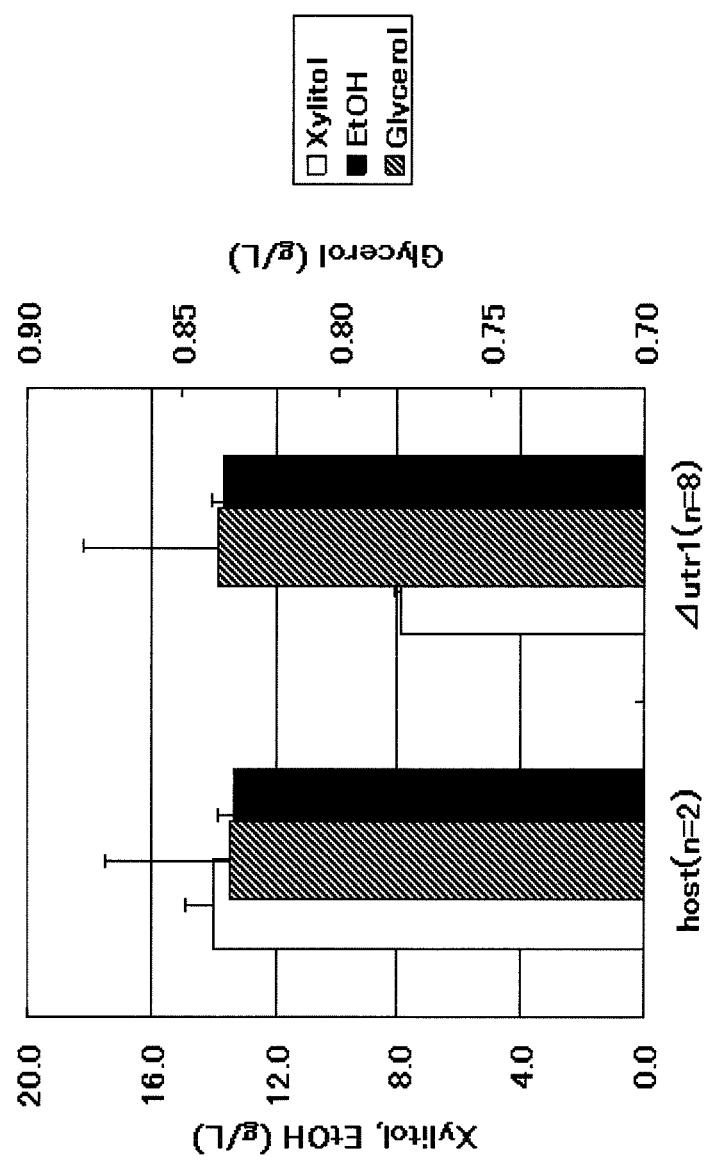
FIG. 13 shows the results of xylose fermentation test using the microorganism of the present invention (medium: YPX, host: HH472, measured after 48 hours). In the figure, "Δutr1" denotes "UTR1 gene disruption."

To confirm reproducibility, the same fermentation test as above was conducted at n=2 for the parent strain and at n=8 for the UTR1 disruptant. As a result, the UTR1 disruptant showed significantly high ethanol yield (FIG. 12), whereas its xylitol production level was low (FIG. 13).

Example 3

Xylose Fermentation Test on UTR1 Disruptants in CSLX Medium

Figure 14:
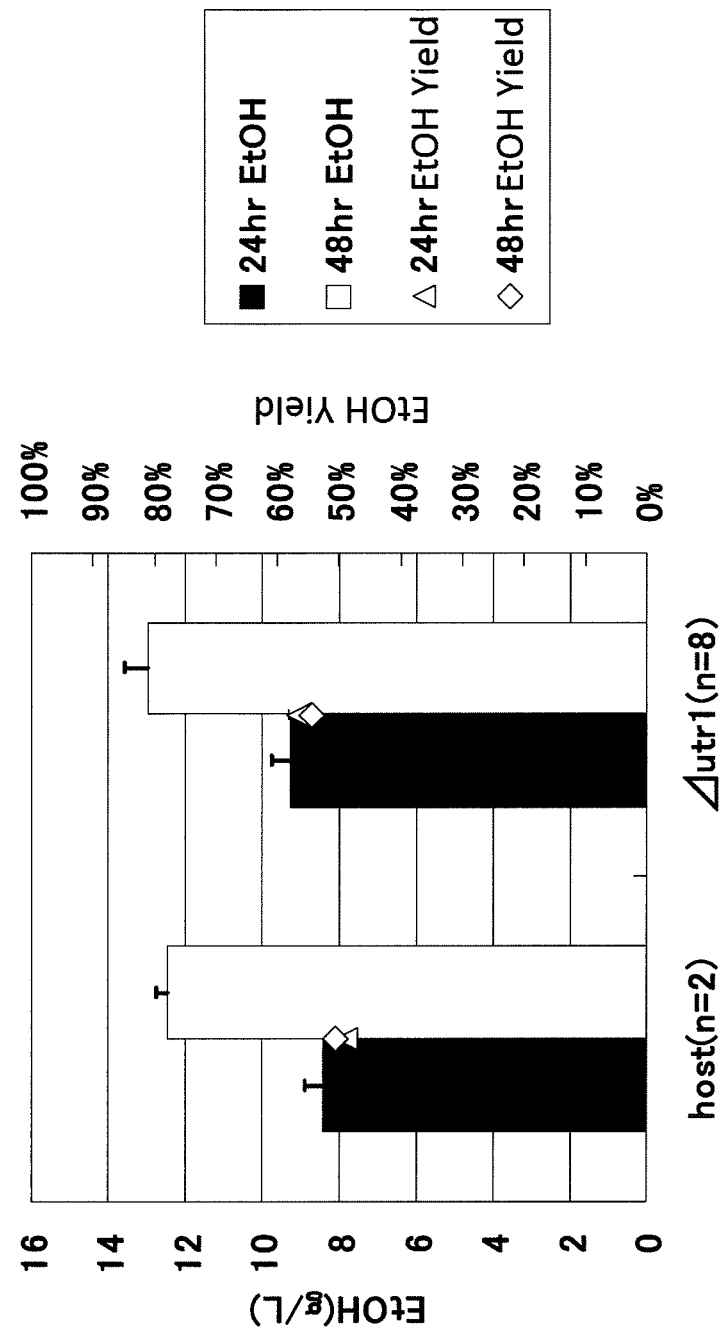
FIG. 14 shows the results of xylose fermentation test using the microorganism of the present invention (medium: CSLX, host: HH472). In the figure, "Δutr1" denotes "UTR1 gene disruption."
Figure 15:
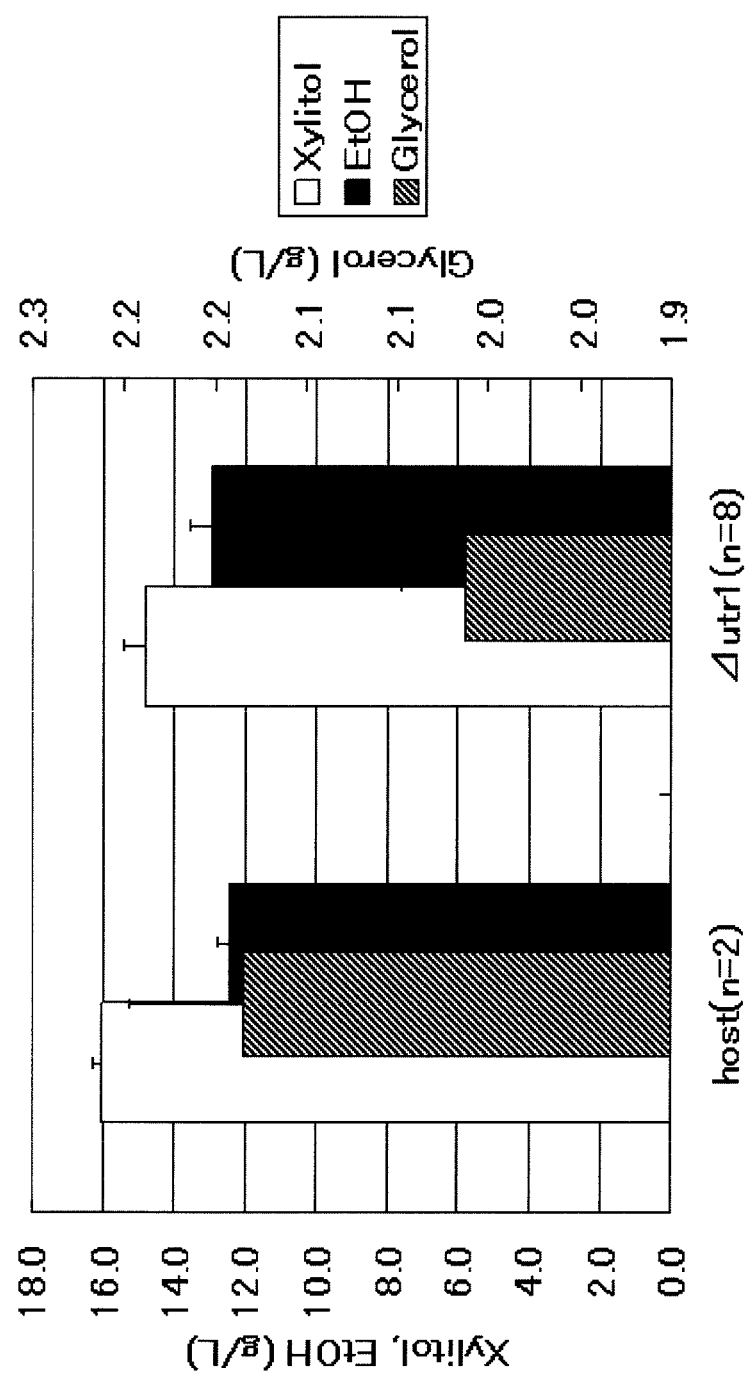
FIG. 15 shows the results of xylose fermentation test using the microorganism of the present invention (medium: CSLX, host: HH472, measured after 48 hours). In the figure, "Δutr1" denotes "UTR1 gene disruption."
Figure 16:
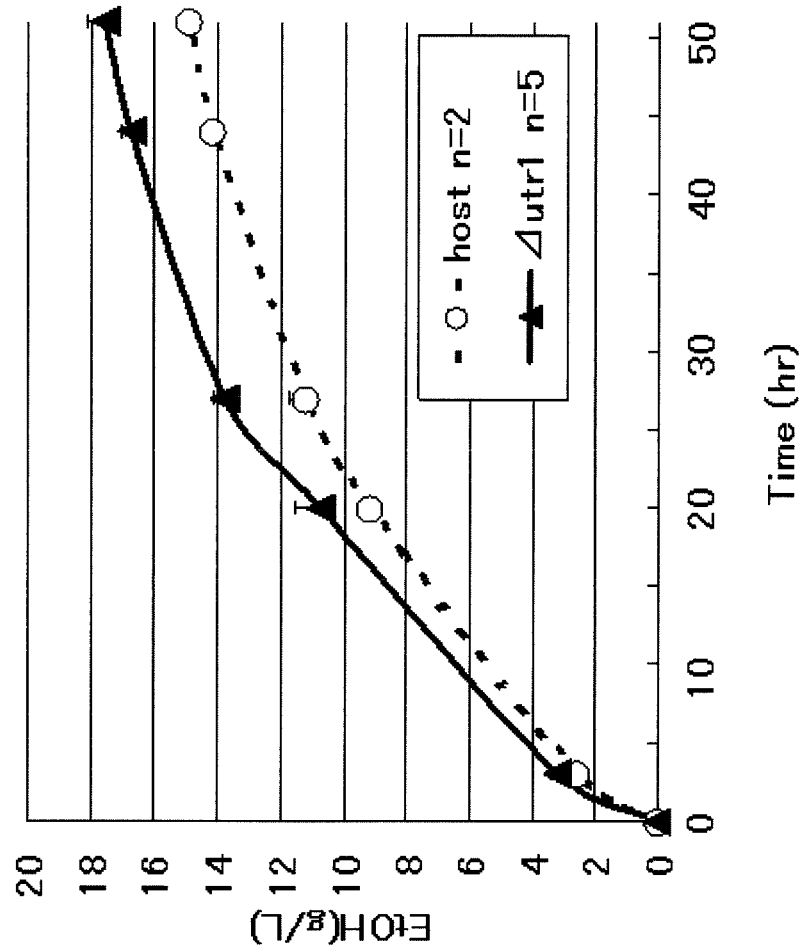
FIG. 16 shows the results of xylose fermentation test using the microorganism of the present invention (medium: CSLX, host: HH472, 45 mL scale, measured after 48 hours). In the figure, "Δutr1" denotes "UTR1 gene disruption."
Figure 17:
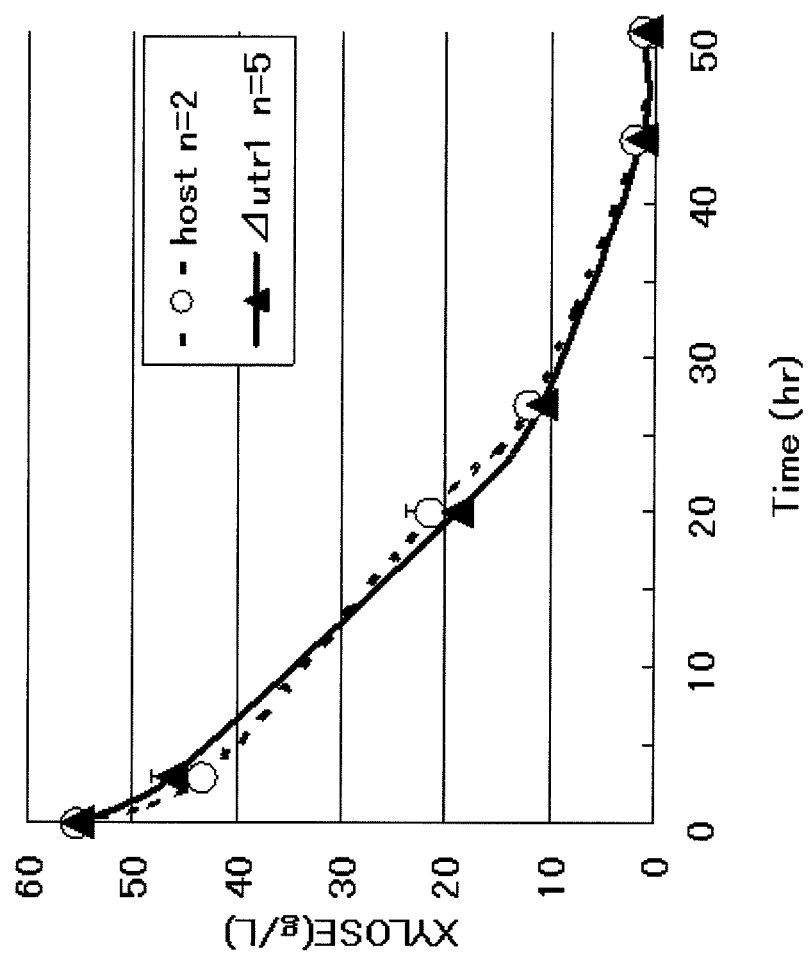
FIG. 17 shows the results of xylose fermentation test using the microorganism of the present invention (medium: CSLX, host: HH472, 45 mL scale, measured after 48 hours). In the figure, "Δutr1" denotes "UTR1 gene disruption."
Figure 18:
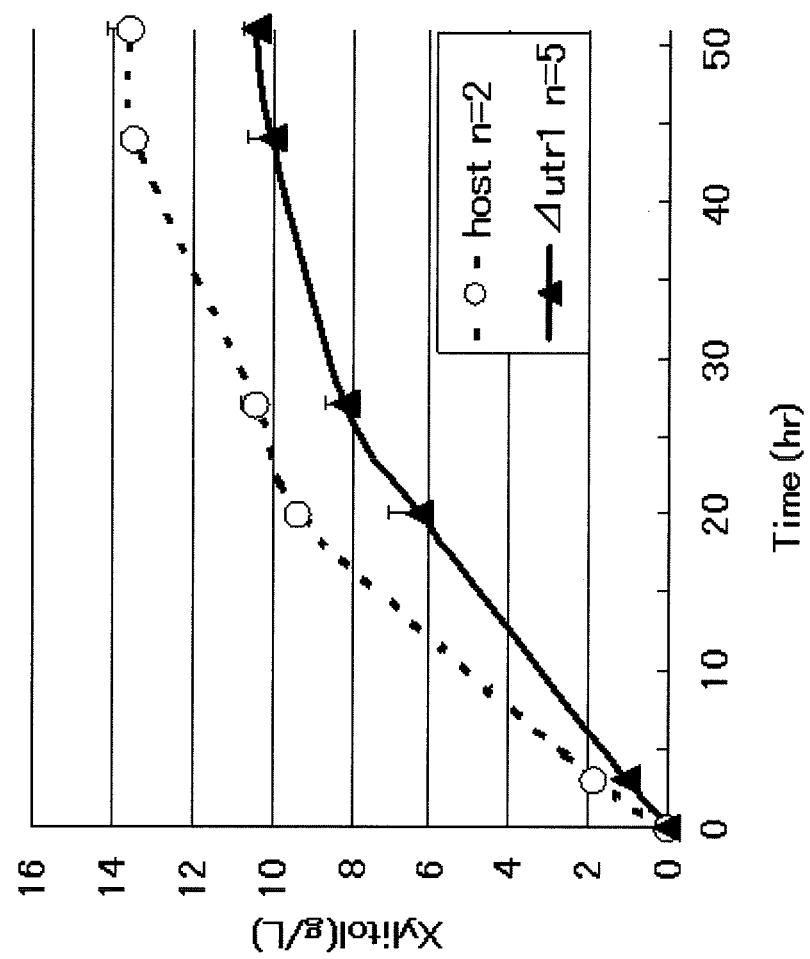
FIG. 18 shows the results of xylose fermentation test using the microorganism of the present invention (xylitol production level, medium: CSLX, host: HH472, 45 mL scale, measured after 48 hours). In the figure, "Δutr1" denotes "UTR1 gene disruption."
Figure 19:
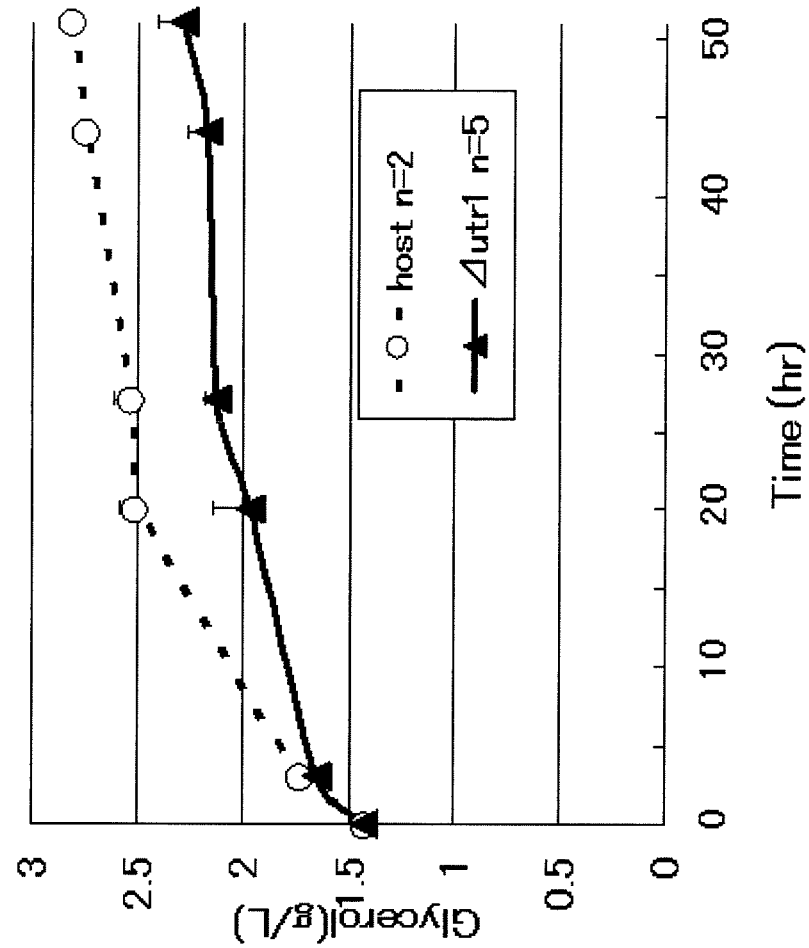
FIG. 19 shows the results of xylose fermentation test using the microorganism of the present invention (glycerol production level, medium: CSLX, host: HH472, 45 mL scale, measured after 48 hours). In the figure, "Δutr1" denotes "UTR1 gene disruption."

The UTR1 disruptant bred from HH472 as a parent strain in Example 2 (n=8) and the parent strain (n=2) were used to conduct a fermentation test in CSLX medium. After being cultured in YPD as described in the test methods, each strain was inoculated into CSLX medium (2 ml) at $OD_{600}$=25 and then transferred to a microtube to conduct a fermentation test at 30° C. under static conditions. After 24 or 48 hours, the yeast cells were separated by centrifugation and the supernatant was quantified for ethanol, xylose, xylitol and glycerol by high performance liquid chromatography. The yield of ethanol was expressed as a percentage, assuming that ethanol production in an amount of xylose assimilation level×0.51 was set to 100% yield. The production level and yield of ethanol are shown in FIG. 14. The UTR1 disruptant showed a significant increase in the yield of ethanol produced from xylose when compared to its parent strain. The levels of by-products, i.e., xylitol and glycerol measured after 48 hours are also shown along with ethanol (FIG. 15). Both levels were lower than in the parent strain. In light of the fact that degradation products of biomass are substantially free from amino acids, it can be regarded as a particularly important result that a similar effect was observed even in CSLX medium whose amino acid content is only about one-fourth of that in YPX. This result indicates that the microorganism of the present invention is useful for ethanol production starting from xylose-containing biomass.

Example 4

Xylose Fermentation Test on UTR1 Disruptants in CSLX Medium on a 45 Ml Scale

The UTR1 disruptant bred from HH472 as a parent strain in Example 2 and the parent strain were each cultured in YPD as described in the test methods at n=2 for the parent strain and at n=5 for the UTR1 disruptant, and then inoculated into CSLX medium (45 ml) in a 100 ml medium bottle at $OD_{600}$=20. At 30° C., a fermentation test was conducted while stirring with a magnet stirrer (60 rpm). After 3, 20, 27, 44 and 51 hours, aliquots were sampled, centrifuged to separate the yeast cells, and then quantified for ethanol, xylose, xylitol and glycerol by high performance liquid chromatography. The yield of ethanol was expressed as a percentage, assuming that ethanol production in an amount of xylose assimilation level×0.51 was set to 100% yield. The time courses of individual ingredients are shown in FIGS. 16 to 19. The UTR1 disruptant showed a reduction in the production levels of xylitol and glycerol and showed an increase in the production level and yield of ethanol when compared to the parent strain. Moreover, the speed of xylose assimilation was the same as in the parent strain. In the case of fermentation under stirring conditions without aeration, UTR1 disruption was also found to cause a reduction in the production levels of xylitol and glycerol, which are by-products of ethanol fermentation, and an increase in the production level of ethanol.

Example 5

Figure 20:
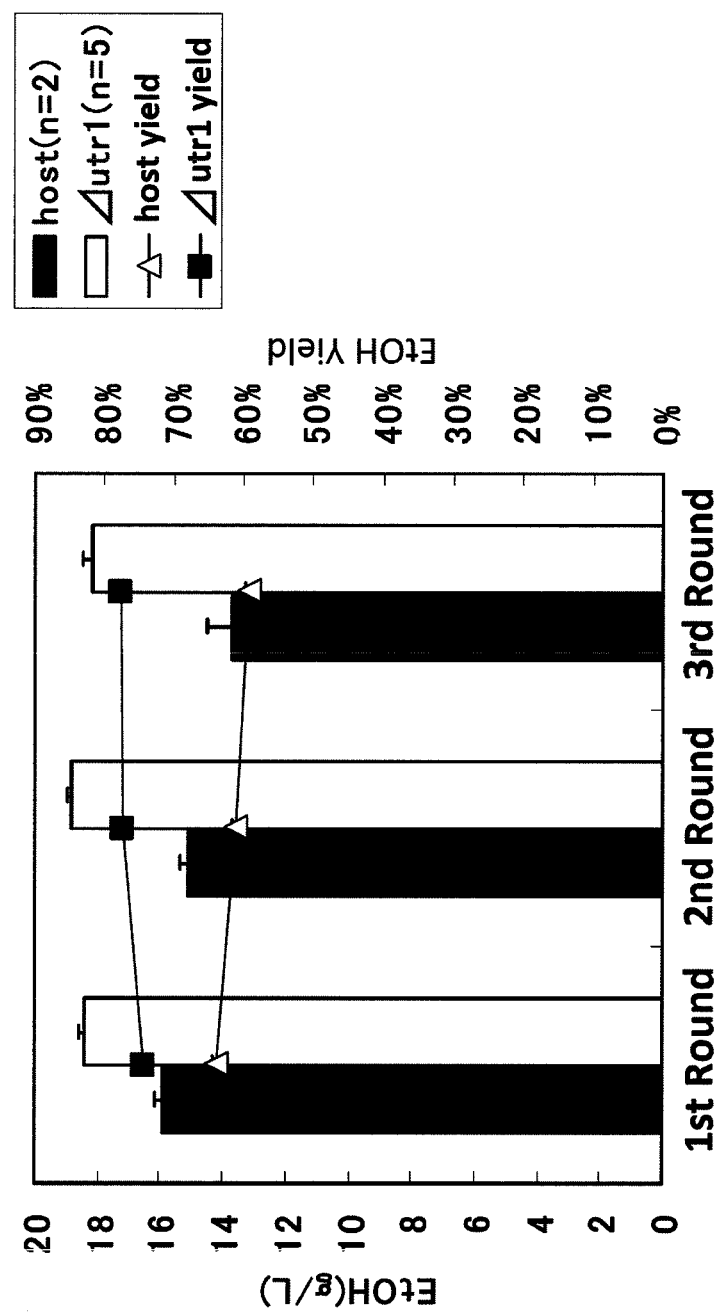
FIG. 20 shows the results of serial batch xylose fermentation test using the microorganism of the present invention (medium: CSLX, host: HH472, measured after 48 hours). In the figure, "Δutr1" denotes "UTR1 gene disruption."
Figure 21:
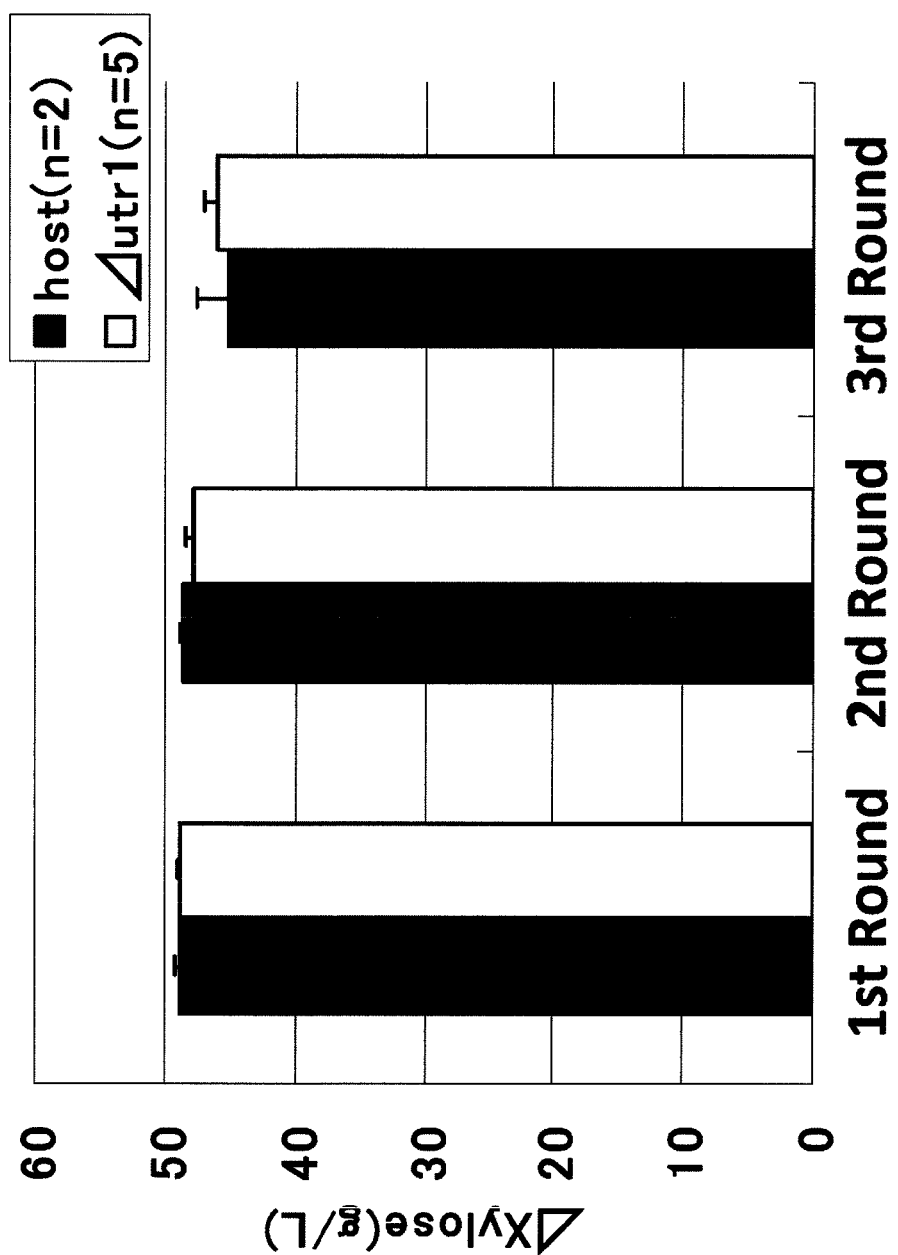
FIG. 21 shows the results of continuous xylose fermentation test using the microorganism of the present invention (xylose assimilation level, medium: CSLX, host: HH472, measured after 48 hours). In the figure, "Δutr1" denotes "UTR1 gene disruption."
Figure 22:
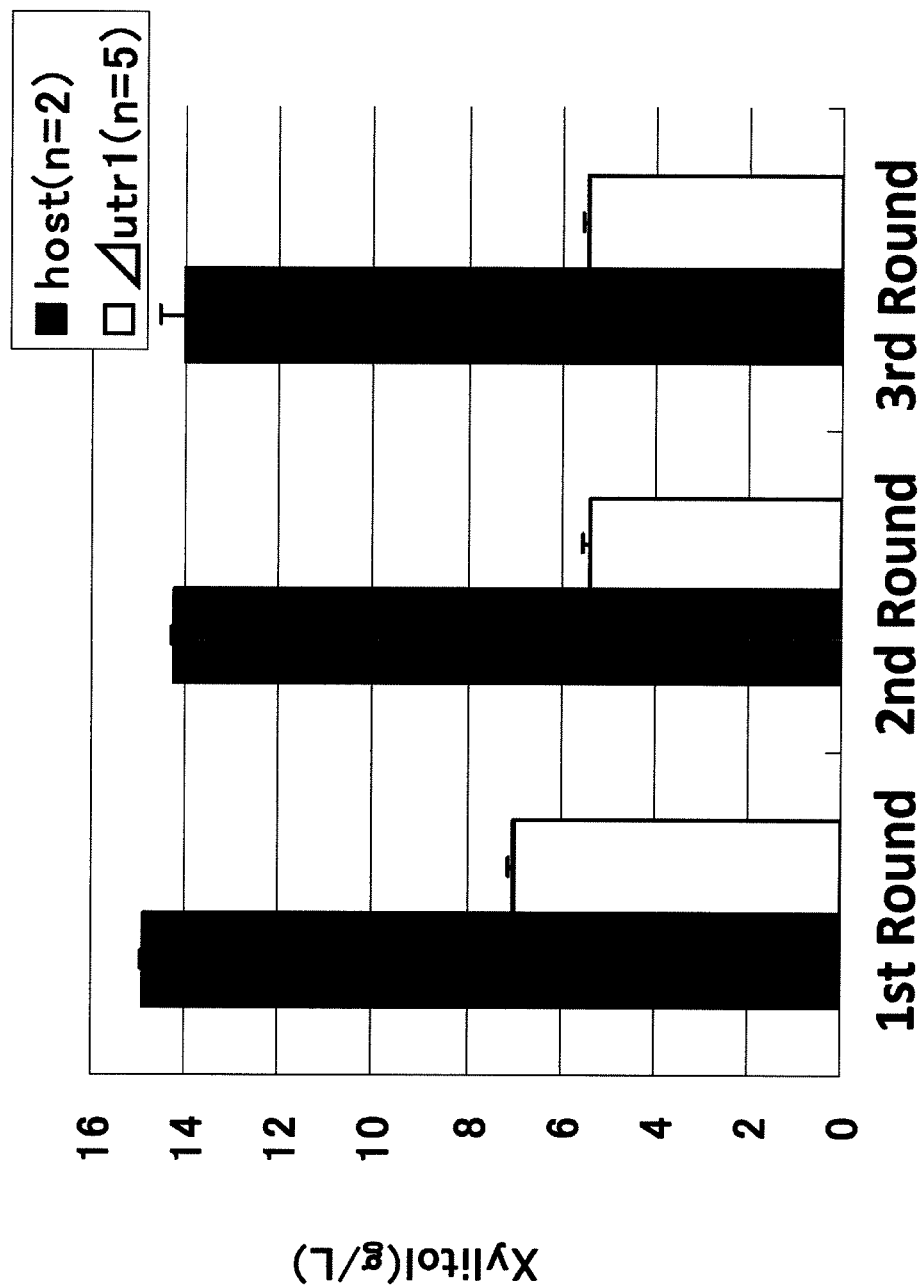
FIG. 22 shows the results of continuous xylose fermentation test using the microorganism of the present invention (xylitol production level, medium: CSLX, host: HH472, measured after 48 hours). In the figure, "Δutr1" denotes "UTR1 gene disruption."
Figure 23:
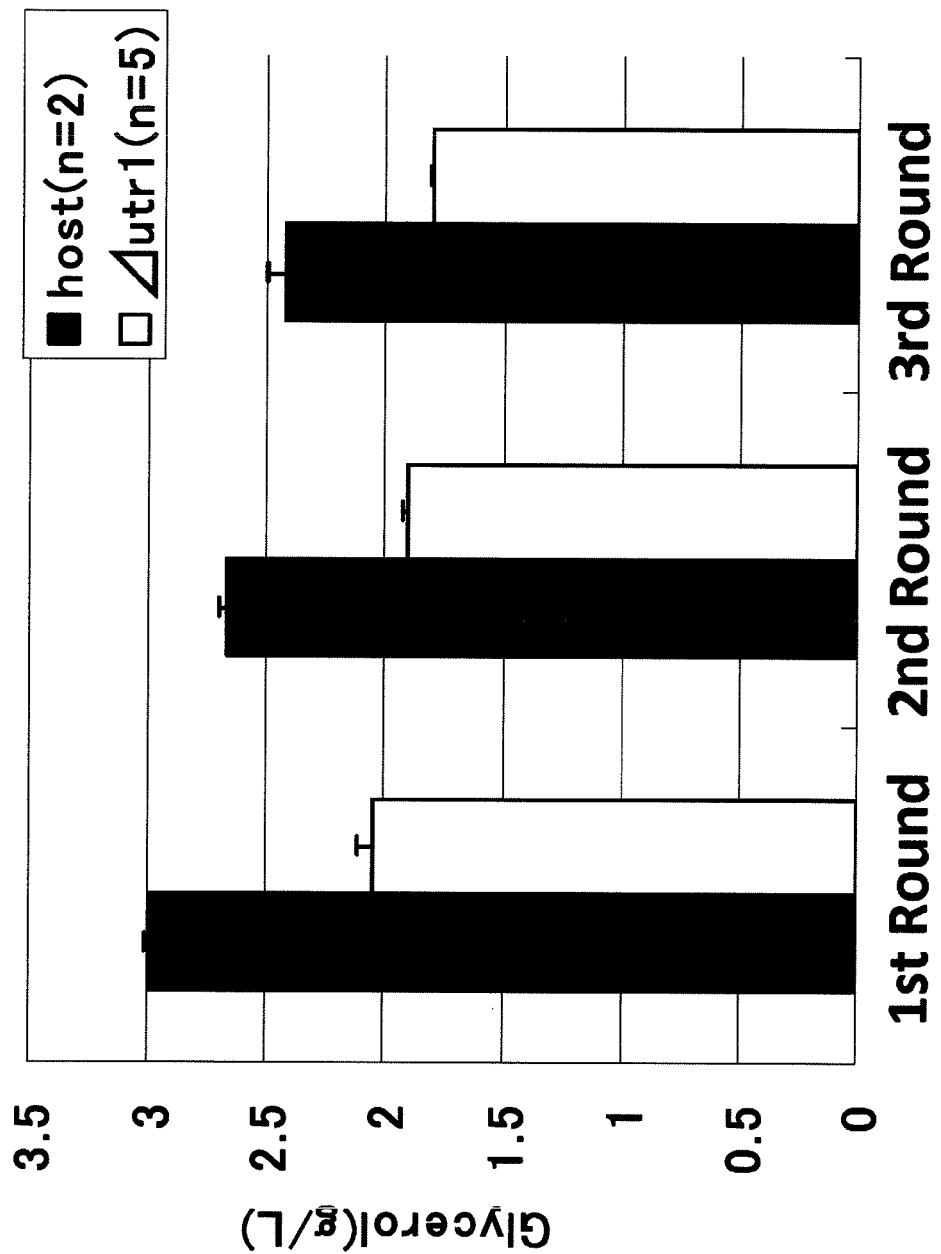
FIG. 23 shows the results of continuous xylose fermentation test using the microorganism of the present invention (glycerol production level, medium: CSLX, host: HH472, measured after 48 hours). In the figure, "Δutr1" denotes "UTR1 gene disruption."

Serial Batch Xylose Fermentation Test on UTR1 Disruptants in CSLX Medium on a 10 ml Scale The parent strain (n=2) and the UTR1 disruptant (n=5) from the fermentation test conducted on a 45 ml scale in Example 4 were each collected by centrifugation, inoculated into 10 ml of CSLX medium at $OD_{600}$=100 and then transferred to a capped sterile plastic tube of 50 ml volume to effect fermentation at 30° C. under static conditions. After 48 hours, aliquots were sampled, centrifuged, filtered and then quantified for ethanol, xylose, xylitol and glycerol by high performance liquid chromatography. The yield of ethanol was calculated as a percentage, assuming that ethanol production in an amount of xylose assimilation level×0.51 was set to 100% yield. Yeast cells in the remainder of the fermented mash were collected in their entirety and used for the next round of fermentation in the same manner. The fermentation was repeated three times in succession. FIG. 20 shows the yield of ethanol production, FIG. 21 shows xylose assimilation level, FIG. 22 shows xylitol production level, and FIG. 23 shows glycerol production level. Even in the case of repeating fermentation in succession, the UTR1 disruptant was higher in both the production level of ethanol and the yield of ethanol than the parent strain. In particular, the yield of ethanol tended to decrease in the parent strain with increase in the number of fermentation rounds, whereas the yield of ethanol conversely tended to increase in the UTR1 disruptant. Moreover, the production levels of by-products, i.e., xylitol and glycerol were low even in the case of serial batch fermentation. Xylose assimilation level was found to slightly decrease with increase in the number of fermentation rounds, although this tendency was also seen in the parent strain. This result indicated that the UTR1 disruptant produced the same effect even in serial batch fermentation. In ethanol production from biomass, the property of being fermentable in a continuous manner is significantly meaningful because it is very important to reduce the production costs.

Example 6

Xylose Fermentation Test on UTR1, YEF1 and UTR1 YEF1 Disruptants in YPX Medium

Figure 24:
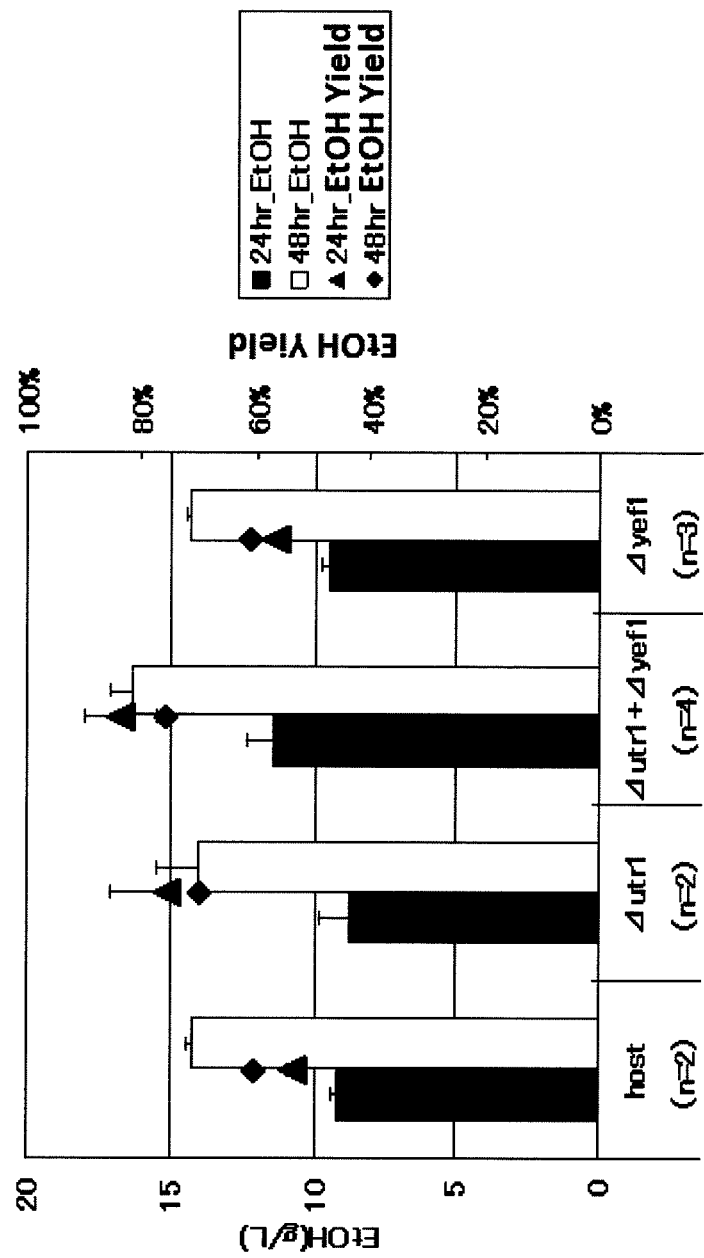
FIG. 24 shows the results of xylose fermentation test (2) using the microorganism of the present invention (medium: YPX, host: HH472). In the figure, "Δutr1" and "Δyef1" denote "UTR1 gene disruption" and "YEF1 gene disruption," respectively.
Figure 25:
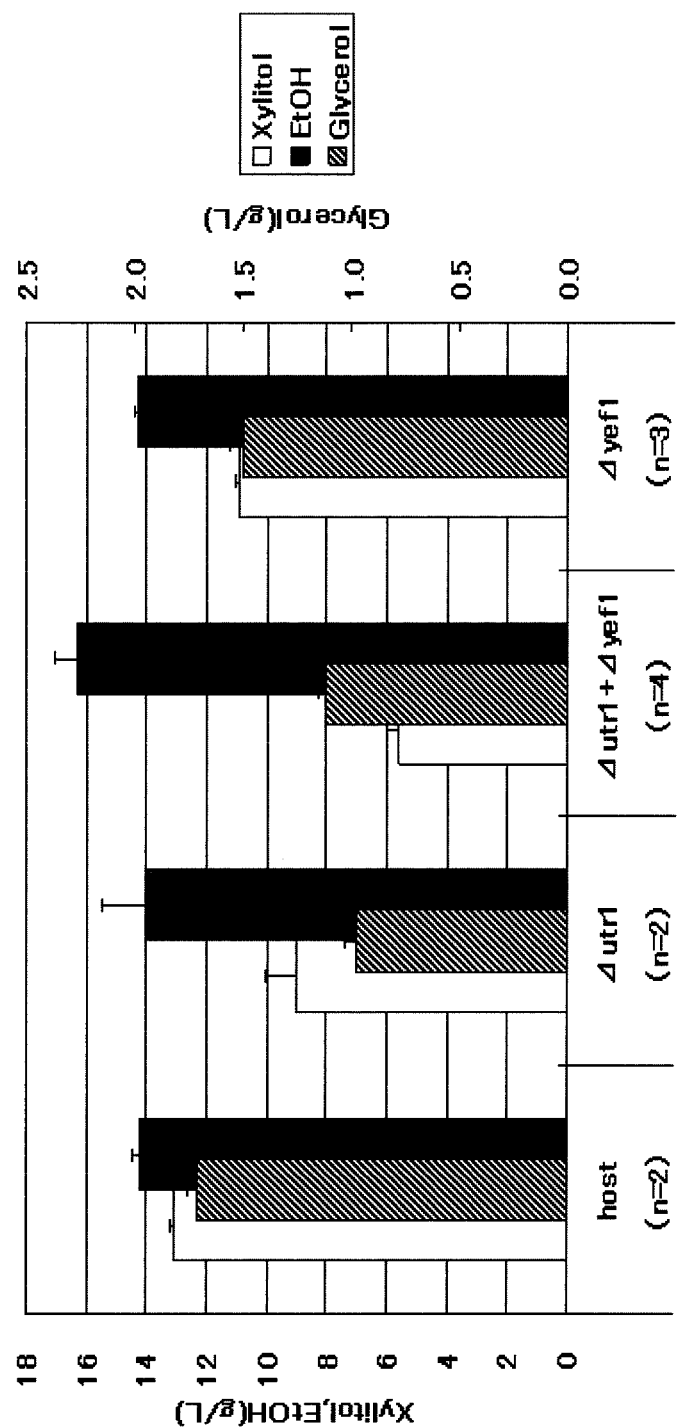
FIG. 25 shows the results of xylose fermentation test (2) using the microorganism of the present invention (medium: YPX, host: HH472, measured after 48 hours). In the figure, "Δutr1" and "Δyef1" denote "UTR1 gene disruption" and "YEF1 gene disruption," respectively.

UTR1, YEF1 and UTR1 YEF1 disruptants prepared using HH472 as a host were bred. The strain HH472 is a strain bred from X2180-1A and is not auxotrophic unlike HH467 and HH468. The parent strain (n=2), the UTR1 disruptant (n=2), the YEF1 disruptant (n=3) and the UTR1 YEF1 disruptant (n=4) were each cultured in YPD as described in the test methods, inoculated into YPX medium (2 ml) at $OD_{600}$=25, and then transferred to a microtube and allowed to stand at 30° C. to conduct a fermentation test. After 24 or 48 hours, the yeast cells were separated by centrifugation and the supernatant was quantified for ethanol and xylose by high performance liquid chromatography. The yield of ethanol was expressed as a percentage, assuming that ethanol production in an amount of xylose assimilation level×0.51 was set to 100% yield. The results obtained are shown in FIG. 24. The UTR1 disruptant showed an increase in the yield of ethanol produced from xylose when compared to the parent strain. The YEF1 disruptant showed only a slight increase in the yield of ethanol produced from xylose when compared to the parent strain, whereas the UTR1 YEF1 disruptant, in which both UTR1 and YEF genes were disrupted, showed a greater increase in the yield of ethanol than the UTR1 disruptant. The levels of by-products, i.e., xylitol and glycerol measured after 48 hours are also shown along with ethanol in FIG. 25. The UTR1 YEF1 disruptant achieved lower production levels of xylitol and glycerol and a higher production level of ethanol than the UTR1 disruptant. Disruption of both UTR1 and YEF1 genes was found to achieve a higher effect.

<Conclusion>

As described above, it was found that NADH reoxidation reaction limited the rate of ethanol fermentation from xylose. This finding indicates that the yield of ethanol can be increased upon disruption of NAD kinase UTR1 gene and/or YEF1 gene. The microorganism of the present invention can be prepared as a strain that is either auxotrophic or not auxotrophic for amino acids which require NAD and/or NADPH for their synthesis, and the thus prepared microorganisms can exert the same effect when used in xylose fermentation. Moreover, in cases where the microorganism of the present invention is used for xylose fermentation, a high fermentation effect can be observed either in a nutrient-rich medium such as YPX or in an industrially used nutrient-poor medium such as corn steep liquor and urea (CSLX).

Example 7

Preparation of FPS1 Disruptant

<Obtaining of FPS1 Gene>

Yeast *Saccharomyces cerevisiae* FPS1 gene (SEQ ID NO: 23) has already been reported as to its nucleotide sequence (Saccharomyces Genome Database Accession No. YLL043W). In addition, the amino acid sequence of FPS1 protein encoded by this gene is shown in SEQ ID NO: 24.

Figure 26:
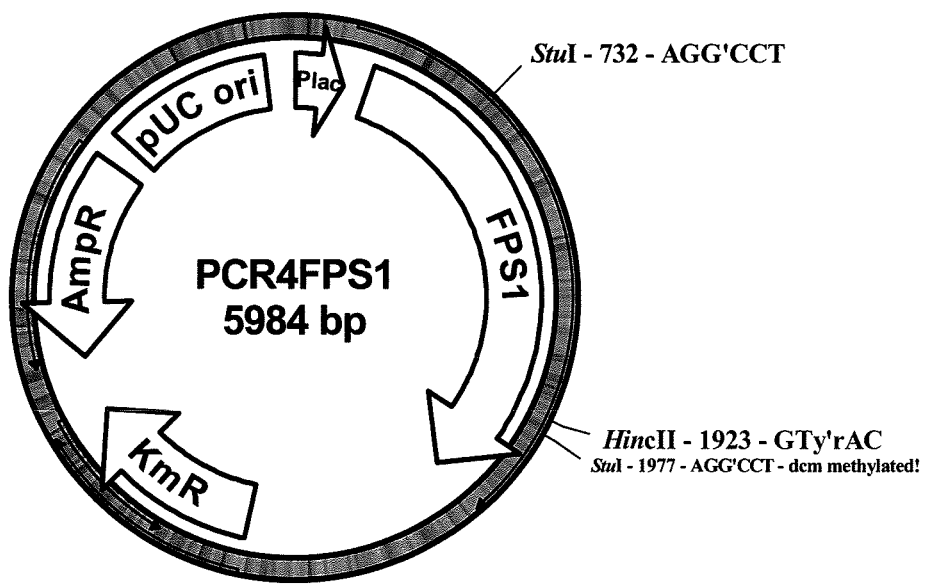
FIG. 26 shows a schematic view of plasmid pCR4FPS1 used in the Example section.

Based on its nucleotide sequence information, the FPS1 gene can be obtained by being PCR amplified and isolated using, as a PCR template, chromosomal DNA prepared from yeast *Saccharomyces cerevisiae*. More specifically, in this example, chromosomal DNA of yeast *Saccharomyces cerevisiae* X2180-1A (ATCC26786) (MATa SUC2 mal mel gal2 CUP1) was used as a template in PCR with primers FPS1NFSCXB and FPS1CRB shown below to obtain FPS1. Using an Invitrogen TOPO TA Cloning® Kit for sequencing, the obtained DNA fragment was inserted into a vector, pCR® 4-TOPO, to thereby obtain plasmid pCR4FPS1 (FIG. 26). The inserted genes were both confirmed for their sequences by DNA sequencing. The chromosomal DNAs used for obtaining both genes are not limited to the strain mentioned above and may be prepared from any yeast strain as long as it belongs to *Saccharomyces cerevisiae*. PCR amplification of the target genes from chromosomal DNAs and the subsequent isolation thereof, including preparation of PCR primers, may be accomplished in a manner well known to those skilled in the art.

```
FPS1NFSCXB:
                                              (SEQ ID NO: 25)
    5' GAGCTCTAGAATGAGTAATCCTCAAAAAGCTC 3'

FPS1CRB:
                                              (SEQ ID NO: 26)
    5' GGATCCTCATGTTACCTTCTTAGCATTAC 3'
```

<Unit Preparation for FPS1 Gene Disruption>

Figure 27:
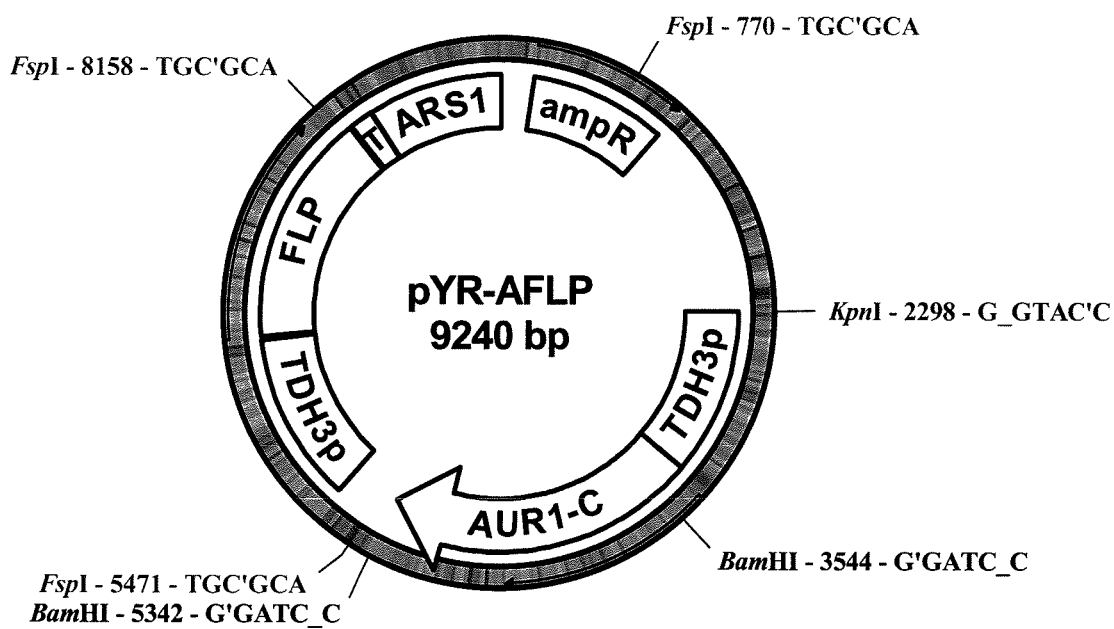
FIG. 27 shows a schematic view of plasmid pYR-AFLP used in the Example section.
Figure 28:
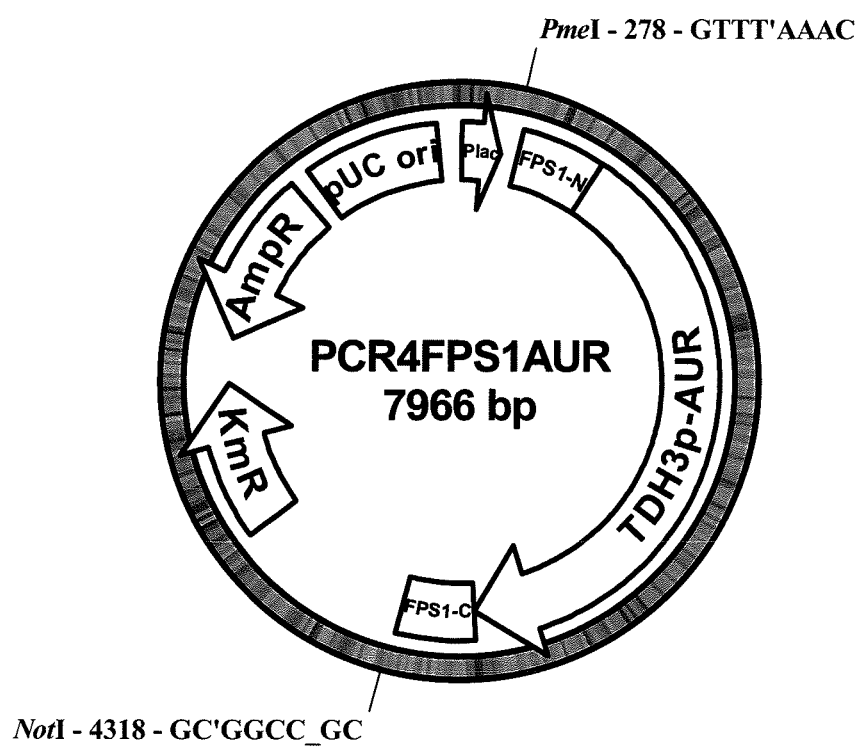
FIG. 28 shows a schematic view of plasmid pCR4FPS1AUR used in the Example section.

To prepare a unit for FPS1 gene disruption, the FPS1 gene in pCR4FPS1 was cleaved with StuI and HincII and then blunted. AUR (aureobasidin) resistance marker gene (TDH3p::AUR1-C) excised with KpnI and FspI from plasmid pYRAFLP (FIG. 27) was inserted into this site to obtain plasmid pCR4FPS1AUR (FIG. 28). This pCR4FPS1AUR was cleaved with PmeI and NotI and then electrophoresed on an agarose gel, followed by excising a DNA fragment of approximately 4.0 kbp (having N-terminal and C-terminal partial sequences from FPS1 and comprising aureobasidin resistance marker gene (TDH3p::AUR1-C) in the center) from the agarose gel. The DNA fragment was purified and extracted from the gel. Its purification and extraction were accomplished by using an Illustra™ GFX™ PCR DNA and Gel Band Purification kit in accordance with the instruction manual.

<Breeding of FPS1 Gene Disruptants>

HH472 or a disruptant thereof, in which either or both of the UTR1 gene and the YEF1 gene were disrupted, was transformed with the prepared DNA fragment of approximately 4.0 kbp (having N-terminal and C-terminal partial sequences from FPS1 and comprising aureobasidin resistance gene (TDH3p::AUR1-C) in the center), and then applied onto a 2 μg/ml aureobasidin-containing YPD (10 g/L yeast extract, 20 g/L polypeptone, 20 g/L glucose* (added after being sterilized by filtration*)) medium. Some of the grown colonies were subjected to PCR with primers FPS1 PF1 and AUR1R shown below to verify amplification of a 1631 bp fragment, thereby confirming that the FPS1 gene was disrupted. Further, the transformants were applied onto YPGly (10 g/L yeast extract, 20 g/L polypeptone, 20 g/L glycerol) medium to verify their growth, thereby confirming that they were not respiratory deficient strains. In the embodiments illustrated here, the aureobasidin resistance marker gene is used as a marker, although other markers may also be used depending on the genotype of host. When using a gene for complementation of the host's auxotrophy, e.g., URA3, selection can be conducted on a uracil-free agar medium. Alternatively, when using YAP1, a drug resistance gene against cycloheximide, selection can be conducted on a cycloheximide-containing YPD medium.

```
                                              (SEQ ID NO: 27)
    FPS1PF1:     5' ATAACGCCTATTGTCCCAATAAG 3'

(SEQ ID NO: 28)
    AUR1_R:      5' CATCTCGAAAAAGGGTTTGC 3'
```

Example 8

Figure 29:
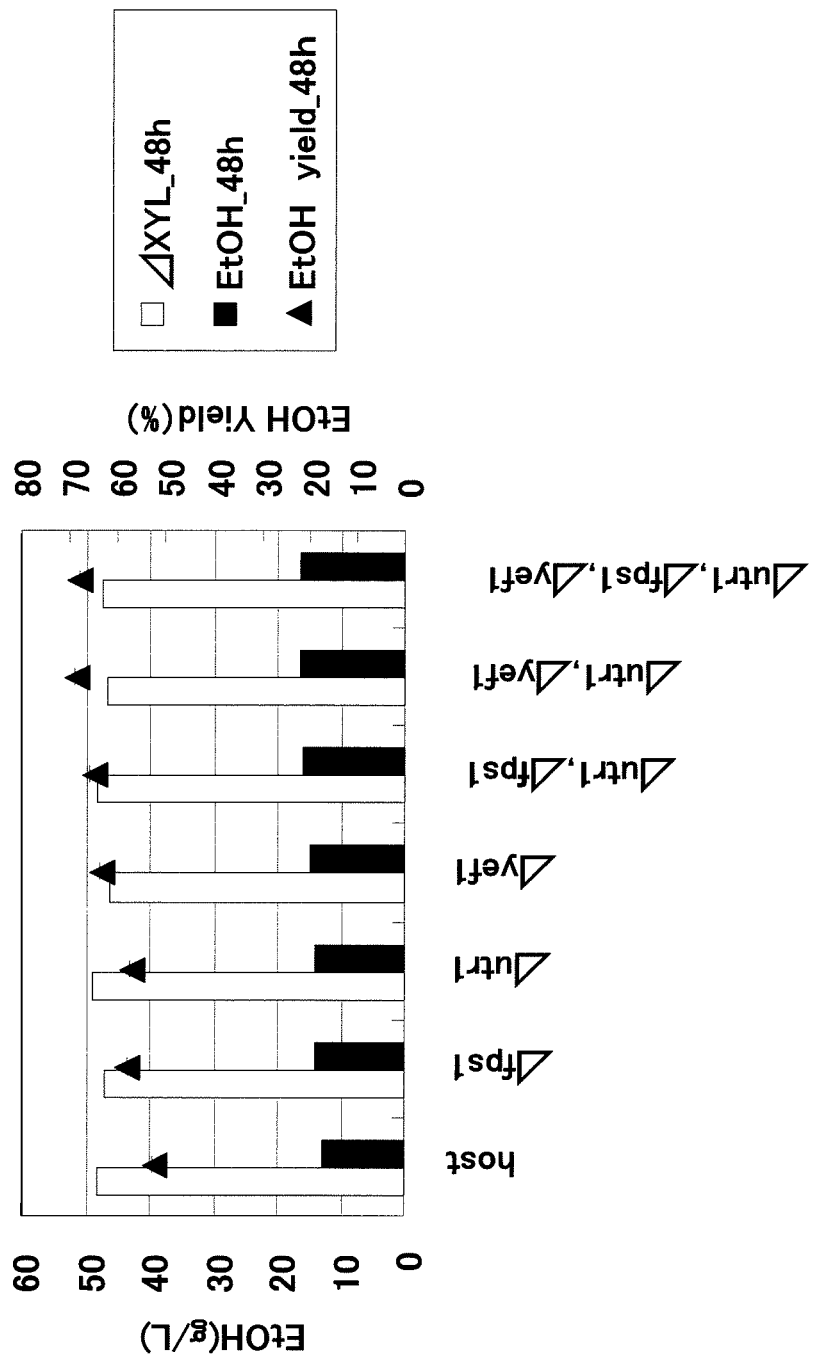
FIG. 29 shows the results of xylose fermentation test using the microorganism of the present invention (medium: YPX, host: HH472, measured after 48 hours). In the figure, "ΔXYL" denotes a decrement in xylose level, while "Δfps1," "Δutr1" and "Δyef1" denote "FPS1 gene disruption," "UTR1 gene disruption" and "YEF1 gene disruption," respectively.
Figure 30:
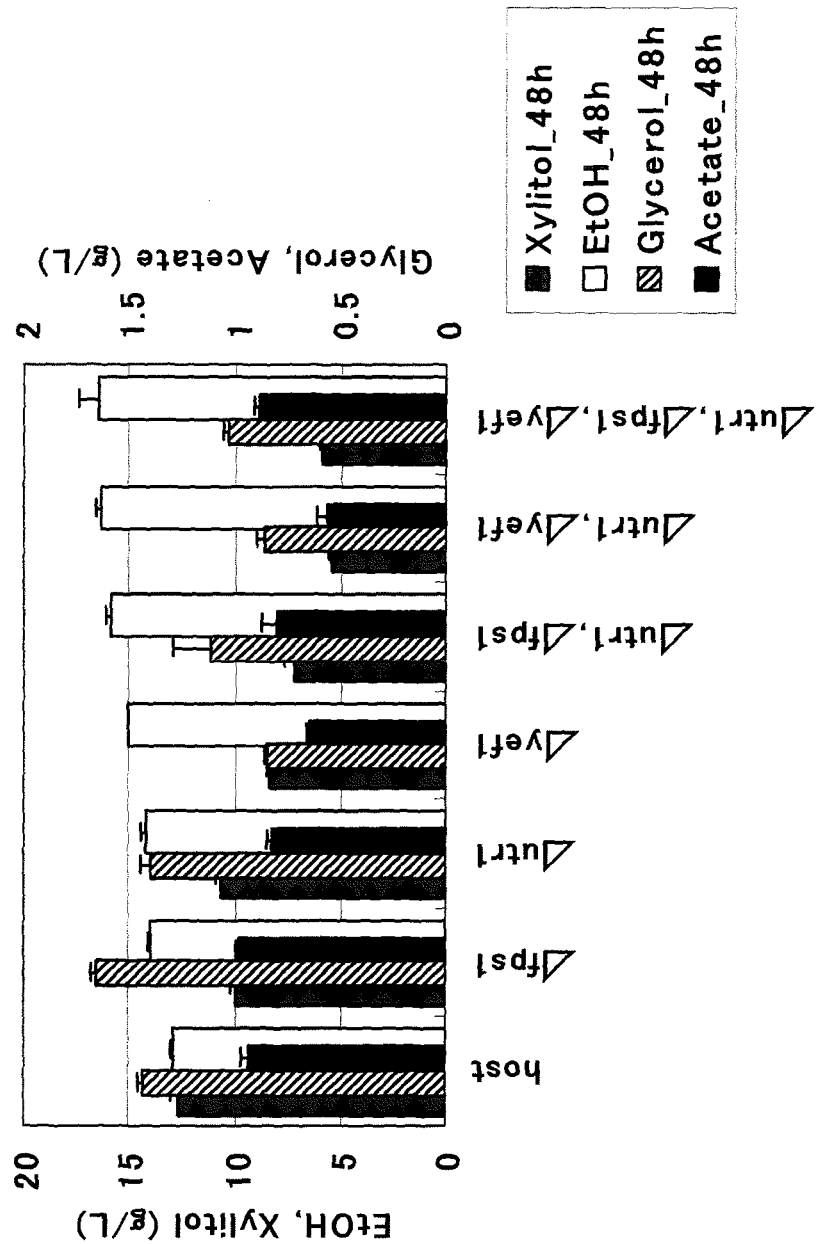
FIG. 30 shows the results of xylose fermentation test using the microorganism of the present invention (medium: YPX, host: HH472, measured after 48 hours). In the figure, "Δfps1," "Δutr1" and "Δyef1" denote "FPS1 gene disruption," "UTR1 gene disruption" and "YEF1 gene disruption," respectively.

Xylose Fermentation Test on UTR1, YEF1, FPS1, UTR1 YEF1, UTR1 FPS1 and UTR1 YEF1 FPS1 Disruptants in YPD and YPX Media Six disruptants UTR1, YEF1, FPS1, UTR1 YEF1, UTR1 FPS1 and UTR1YEF1 FPS1 constructed using HH472 as a host and their parent strain HH472 were each cultured in YPD as described in the test methods, and then inoculated into YPX medium or YPD medium (2 ml) at $OD_{600}$=25 and transferred to a microtube to conduct a fermentation test at 30° C. under static conditions (n=3 for each strain). After 24 or 48 hours, the yeast cells were separated by centrifugation (sampled only after 24 hours in the case of fermentation in YPD), followed by high performance liquid chromatography to quantify ethanol, xylose, xylitol, glycerol and acetic acid in the case of xylose fermentation and to quantify ethanol, glucose, glycerol and acetic acid in the case of glucose fermentation. The yield of ethanol from xylose was expressed as a percentage, assuming that ethanol production in an amount of xylose assimilation level×0.51 was set to 100% yield. The results obtained are shown in FIG. 29. As in the case of the UTR1 disruptant and the YEF1 disruptant, the FPS1 disruptant showed an increase in the yield of ethanol produced from xylose when compared to the parent strain (FIG. 29). The levels of by-products, i.e., xylitol, glycerol and acetic acid measured after 48 hours are shown along with ethanol (FIG. 30). The FPS1 disruptant showed a slight increase in glycerol and acetic acid levels when compared to the parent strain, whereas xylitol production level was lower than in the parent strain. The UTR1 YEF1 disruptant, the UTR1 FPS1 disruptant and the UTR1 YEF1 FPS1 disruptant all showed a decrease in by-product production levels when compared to the single disruptants of these genes, and hence showed an increase in the yield of ethanol from xylose, thus indicating that the yield of ethanol from xylose can be effectively increased when these three genes are disrupted in any combination.

Figure 31:
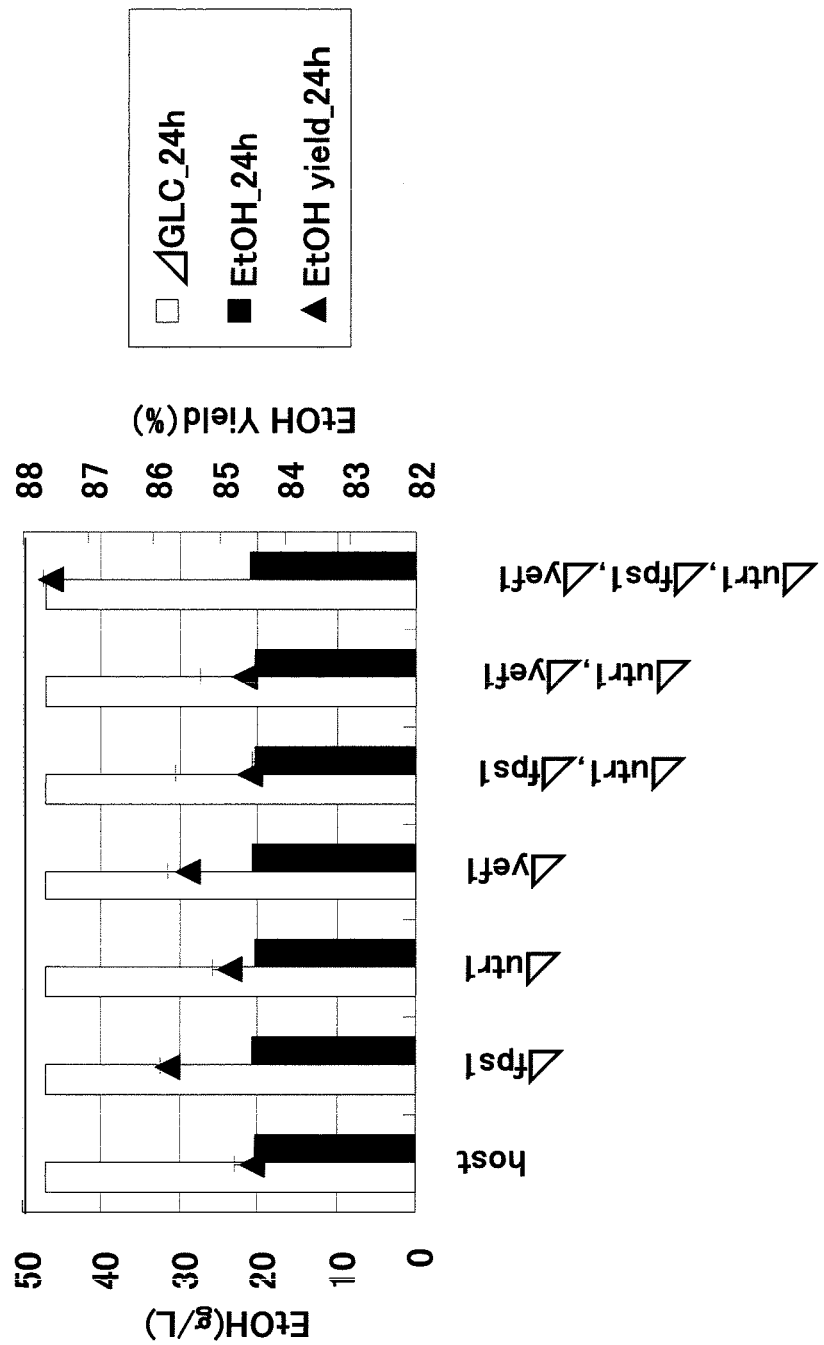
FIG. 31 shows the results of fermentation test using the microorganism of the present invention (medium: YPD, host: HH472, measured after 24 hours). In the figure, "ΔGLC" denotes a decrement in glucose level, while "Δfps1," "Δutr1" and "Δyef1" denote "FPS1 gene disruption," "UTR1 gene disruption" and "YEF1 gene disruption," respectively.
Figure 32:
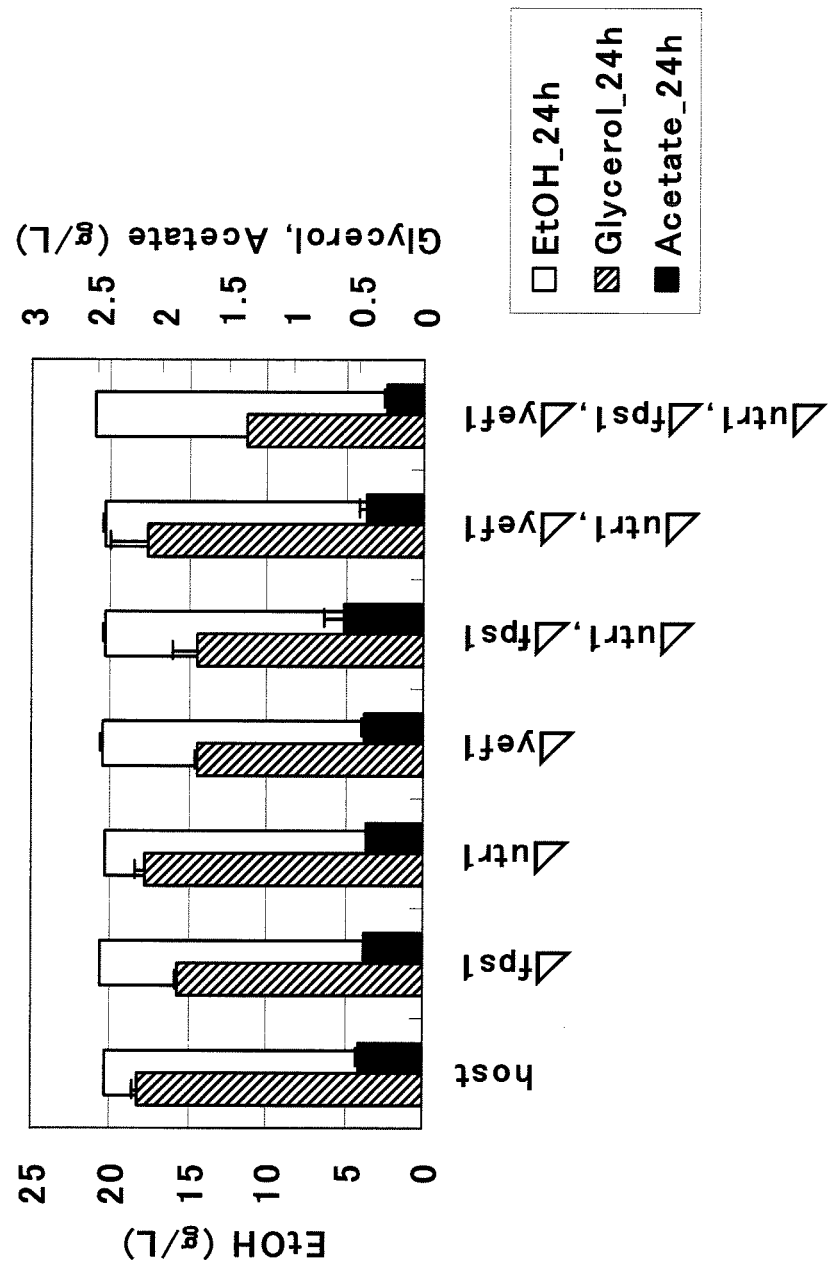
FIG. 32 shows the results of fermentation test using the microorganism of the present invention (medium: YPD, host: HH472, measured after 24 hours). In the figure, "Δfps1," "Δutr1" and "Δyef1" denote "FPS1 gene disruption," "UTR1 gene disruption" and "YEF1 gene disruption," respectively.
Figure 33:
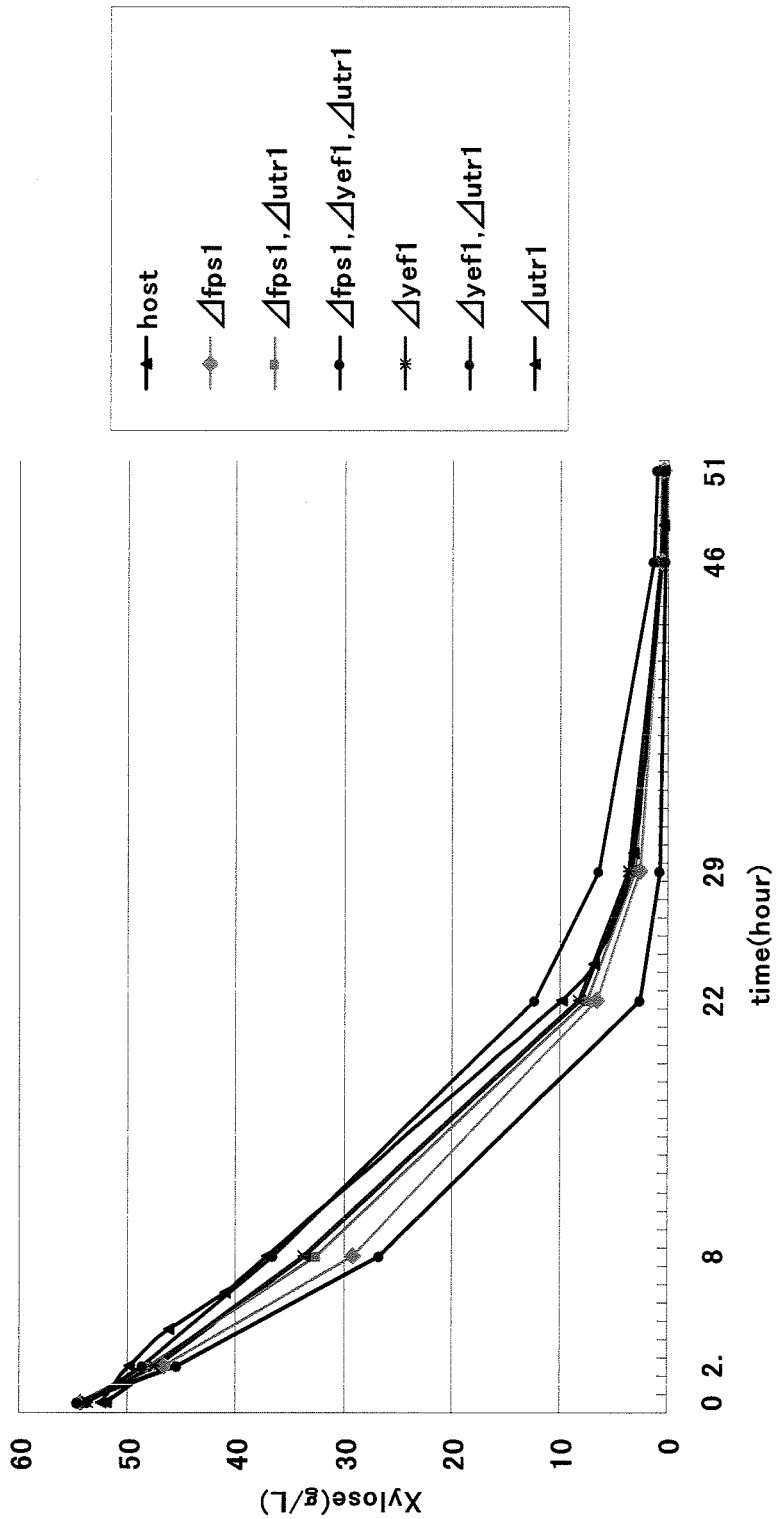
FIG. 33 shows the results of xylose fermentation test (50 ml scale) using the microorganism of the present invention (medium: YPX, host: HH472). In the figure, "Δfps1," "Δutr1" and "Δyef1" denote "FPS1 gene disruption," "UTR1 gene disruption" and "YEF1 gene disruption," respectively.
Figure 34:
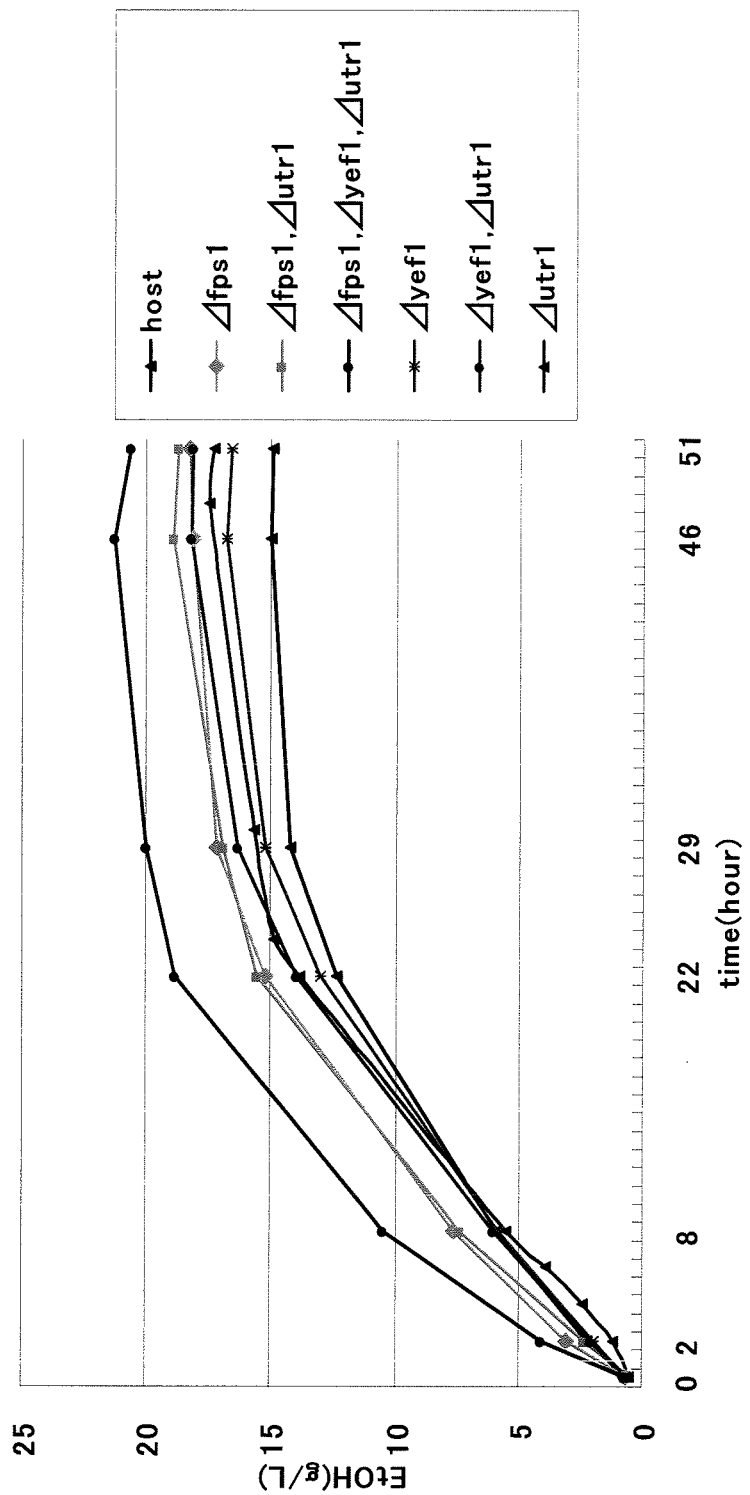
FIG. 34 shows the results of xylose fermentation test (50 ml scale) using the microorganism of the present invention (medium: YPX, host: HH472). In the figure, "Δfps1," "Δutr1" and "Δyef1" denote "FPS1 gene disruption," "UTR1 gene disruption" and "YEF1 gene disruption," respectively.
Figure 35:
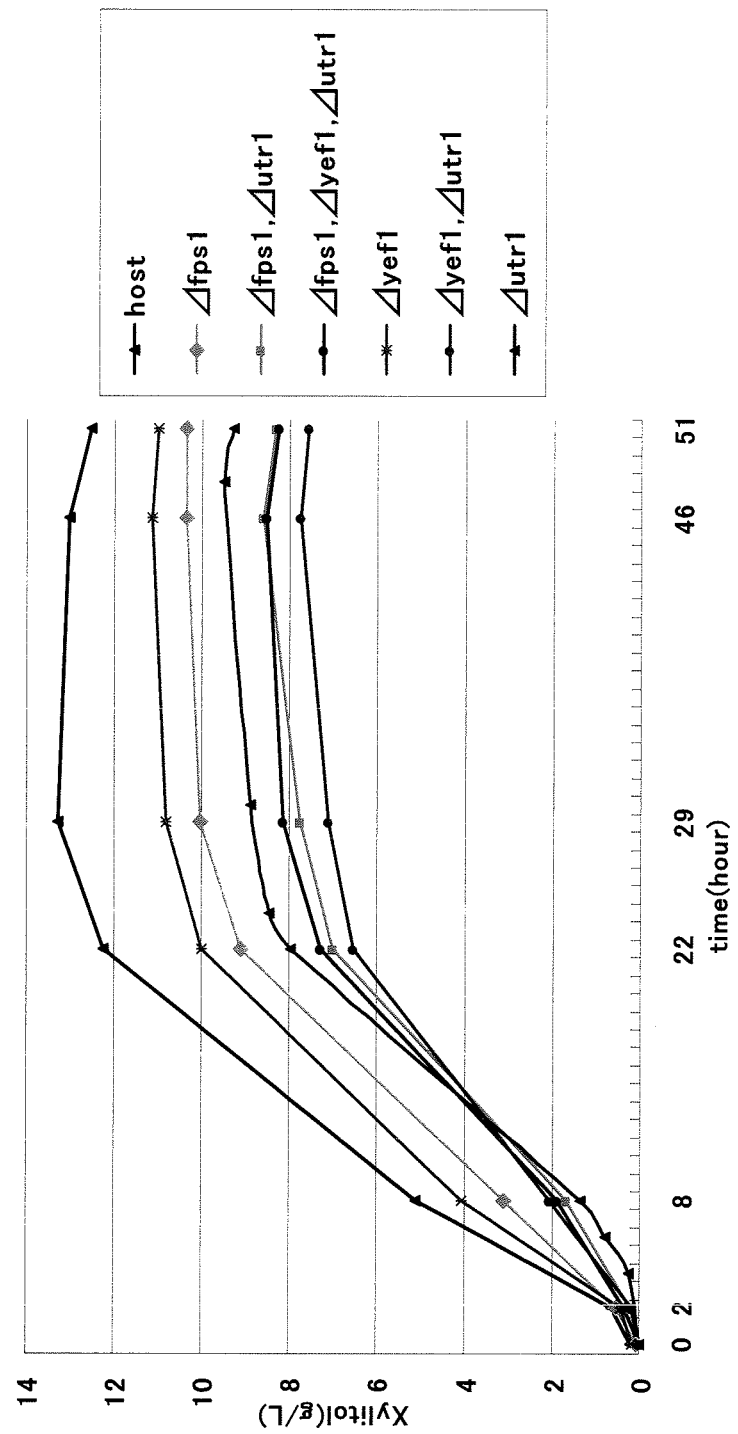
FIG. 35 shows the results of xylose fermentation test (50 ml scale) using the microorganism of the present invention (medium: YPX, host: HH472). In the figure, "Δfps1," "Δutr1" and "Δyef1" denote "FPS1 gene disruption," "UTR1 gene disruption" and "YEF1 gene disruption," respectively.
Figure 36:
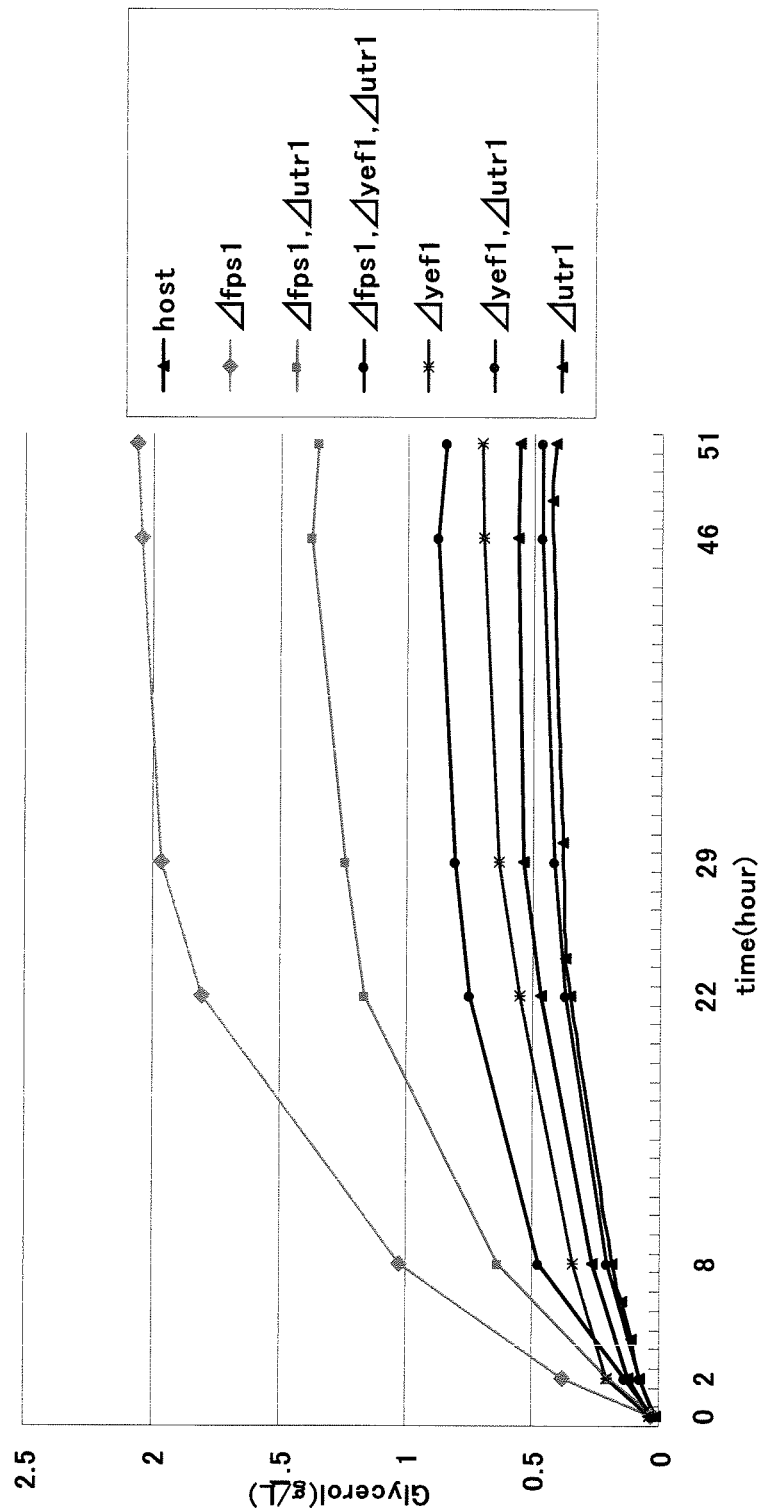
FIG. 36 shows the results of xylose fermentation test (50 ml scale) using the microorganism of the present invention (medium: YPX, host: HH472). In the figure, "Δfps1," "Δutr1" and "Δyef1" denote "FPS1 gene disruption," "UTR1 gene disruption" and "YEF1 gene disruption," respectively.
Figure 37:
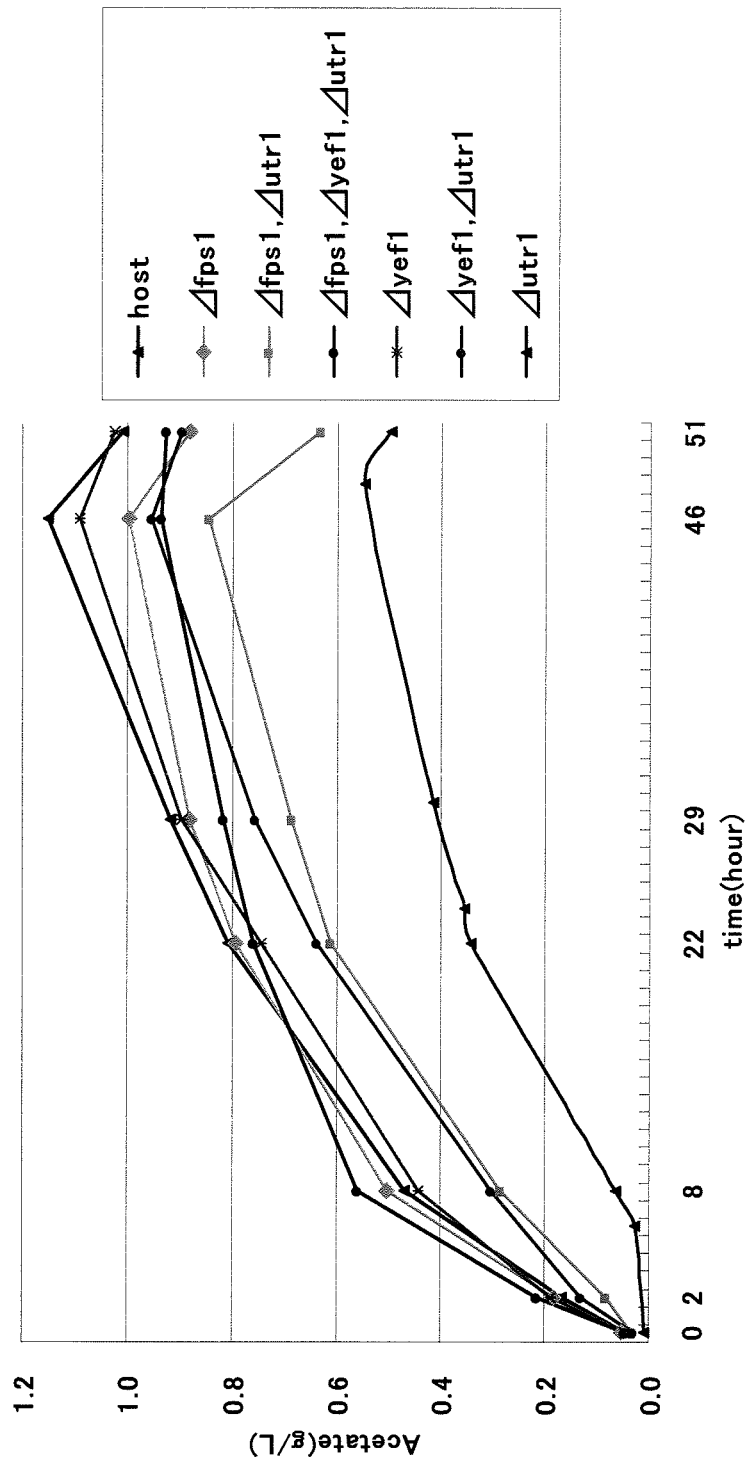
FIG. 37 shows the results of xylose fermentation test (50 ml scale) using the microorganism of the present invention (medium: YPX, host: HH472). In the figure, "Δfps1," "Δutr1" and "Δyef1" denote "FPS1 gene disruption," "UTR1 gene disruption" and "YEF1 gene disruption," respectively.

As in the case of xylose fermentation, the yield of ethanol from glucose was expressed as a percentage, assuming that ethanol production in an amount of glucose assimilation level×0.51 was set to 100% yield. The results obtained are shown in FIG. 31 and FIG. 32. All the disruptants showed almost the same or slightly increased yield of ethanol production during glucose fermentation, thus indicating that these disruptants are not inferior in the production level of ethanol to their parent strain even when the carbon source is glucose.

Example 9

Xylose Fermentation Test on UTR1, YEF1, FPS1, UTR1 YEF1, UTR1 FPS1 and UTR1 YEF1 FPS1 Disruptants in YPX Medium on a 50 ml Scale The disruptants bred from HH472 as a parent strain in Example 8 and the parent strain were each cultured in YPD as described in the test methods and then inoculated into YPX medium (50 ml) in a 100 ml medium bottle at 50 mg wet cell/ml. At 30° C., a fermentation test was conducted while stirring with a magnet stirrer (60 rpm). After 2, 8, 22, 29, 46 and 51 hours, aliquots were sampled, centrifuged to separate the yeast cells, and then quantified for xylose, ethanol, xylitol, glycerol and acetic acid by high performance liquid chromatography. The time courses of individual ingredients are shown in FIGS. 33 to 37. All the disruptants showed a reduction in the production levels of xylitol and acetic acid when compared to their parent strain. Glycerol production level was increased in the FPS1 disruptants, i.e., the FPS1 disruptant, the UTR1 FPS1 disruptant and the UTR1 YEF1 FPS1 disruptant, whereas ethanol production level was greater in all the disruptants than in their parent strain. Even in the case of fermentation under stirring conditions without aeration, the yield of ethanol from xylose can also be effectively increased when these three genes UTR1, YEF1 and FPS1 are disrupted either alone or in any combination.

INDUSTRIAL APPLICABILITY

During ethanol fermentation where pentoses originating from biomass are used as carbon sources, the yield of ethanol production can be increased. In particular, a higher effect can be expected in cases where biomass is rich in hemicelluloses. Moreover, this technique also achieves increased yields in cases where yeast is allowed to produce substances which require NAD for their production, i.e., ethanol production from arabinose, etc.

Sequence Listing Free Text
SEQ ID NO: 5: synthetic DNA
SEQ ID NO: 6: synthetic DNA
SEQ ID NO: 7: synthetic DNA
SEQ ID NO: 8: synthetic DNA
SEQ ID NO: 15: synthetic DNA
SEQ ID NO: 16: synthetic DNA
SEQ ID NO: 17: synthetic DNA
SEQ ID NO: 18: synthetic DNA
SEQ ID NO: 19: synthetic DNA
SEQ ID NO: 20: synthetic DNA
SEQ ID NO: 21: synthetic DNA
SEQ ID NO: 22: synthetic DNA
SEQ ID NO: 25: synthetic DNA
SEQ ID NO: 26: synthetic DNA
SEQ ID NO: 27: synthetic DNA
SEQ ID NO: 28: synthetic DNA

The invention claimed is:

1. A yeast deficient in the function of expressing an NAD kinase gene, which is transformed with at least one of a xylose reductase gene, a xylitol dehydrogenase gene, and a xylulose kinase gene.

2. The yeast according to claim 1, wherein the NAD kinase gene is at least one selected from a UTR1 gene and a YEF1 gene.

3. The yeast according to claim 1, which is further deficient in the function of expressing an FPS1 gene.

4. The yeast according to claim 1, which is *Saccharomyces cerevisiae*.

5. A method for preparing a yeast whose xylose fermentation ability is increased, which comprises causing a deficiency in the function of expressing an NAD kinase gene in the yeast, and transforming the yeast with at least one of a xylose reductase gene, a xylitol dehydrogenase gene, and a xylulose kinase gene which produces the yeast according to claim 1.

6. The method according to claim 5, wherein the NAD kinase gene is at least one selected from a UTR1 gene and a YEF1 gene.

7. The method according to claim 5, which further comprises causing a deficiency in the function of expressing an FPS1 gene.

8. The method according to claim 5, wherein the yeast is *Saccharomyces cerevisiae*.

9. A method for producing ethanol, which comprises contacting the yeast according to claim 1 with xylose-containing raw materials.

* * * * *

SEQUENCE LISTING

```
<160> NUMBER OF SEQ ID NOS: 28

<210> SEQ ID NO 1
<211> LENGTH: 1593
<212> TYPE: DNA
<213> ORGANISM: Saccharomyces cerevisiae
<220> FEATURE:
<221> NAME/KEY: CDS
<222> LOCATION: (1)..(1590)

<400> SEQUENCE: 1 atg aag gag aat gac atg aat aat ggc gta gat aaa tgg gta aat gag      48
Met Lys Glu Asn Asp Met Asn Asn Gly Val Asp Lys Trp Val Asn Glu
1               5                   10                  15 gaa gat ggt cga aat gat cat cat aac aac aat aat aac ttg atg aag      96
Glu Asp Gly Arg Asn Asp His His Asn Asn Asn Asn Asn Leu Met Lys
                20                  25                  30 aag gcc atg atg aac aat gag caa att gat aga act cag gat atc gac     144
Lys Ala Met Met Asn Asn Glu Gln Ile Asp Arg Thr Gln Asp Ile Asp
            35                  40                  45 aac gcc aaa gaa atg ttg agg aaa ata tca agt gaa agc agc tcg cgc     192
Asn Ala Lys Glu Met Leu Arg Lys Ile Ser Ser Glu Ser Ser Ser Arg
        50                  55                  60 aga agc tcc ctg ttg aat aaa gat tca tct ctc gtg aac ggc aat gca     240
Arg Ser Ser Leu Leu Asn Lys Asp Ser Ser Leu Val Asn Gly Asn Ala
65                  70                  75                  80 aac agt ggc ggt ggt acg agc att aac gga aca aga gga agt tct aag     288
Asn Ser Gly Gly Gly Thr Ser Ile Asn Gly Thr Arg Gly Ser Ser Lys
                85                  90                  95 agt agt aat aca cac ttt cag tat gcc tcc acg gcg tat ggt gta aga     336
Ser Ser Asn Thr His Phe Gln Tyr Ala Ser Thr Ala Tyr Gly Val Arg
            100                 105                 110 atg ttg agt aaa gat ata tct aat acc aaa gtg gaa ctg gat gtg gaa     384
Met Leu Ser Lys Asp Ile Ser Asn Thr Lys Val Glu Leu Asp Val Glu
        115                 120                 125 aat ttg atg att gtt acg aaa ctc aac gat gtc tca ctg tat ttc tta     432
Asn Leu Met Ile Val Thr Lys Leu Asn Asp Val Ser Leu Tyr Phe Leu
    130                 135                 140 aca aga gag ttg gta gaa tgg gtt ttg gta cat ttt cca cgt gtg act     480
Thr Arg Glu Leu Val Glu Trp Val Leu Val His Phe Pro Arg Val Thr
145                 150                 155                 160
```

-continued

```
gtt tat gtg gat tcc gaa ttg aaa aac agc aaa aaa ttt gcc gct ggc    528
Val Tyr Val Asp Ser Glu Leu Lys Asn Ser Lys Lys Phe Ala Ala Gly
            165                 170                 175 gag tta tgt gaa gat agt aaa tgt aga gaa tca agg atc aag tat tgg    576
Glu Leu Cys Glu Asp Ser Lys Cys Arg Glu Ser Arg Ile Lys Tyr Trp
            180                 185                 190 aca aag gat ttc atc agg gaa cat gat gtt ttc ttc gat ttg gta gtg    624
Thr Lys Asp Phe Ile Arg Glu His Asp Val Phe Phe Asp Leu Val Val
            195                 200                 205 act ttg ggt ggc gac ggt act gtt ctt ttt gta agt tcc att ttt cag    672
Thr Leu Gly Gly Asp Gly Thr Val Leu Phe Val Ser Ser Ile Phe Gln
            210                 215                 220 aga cat gta cca ccc gtt atg tcg ttt tca tta ggg tct cta gga ttt    720
Arg His Val Pro Pro Val Met Ser Phe Ser Leu Gly Ser Leu Gly Phe
225                 230                 235                 240 tta aca aat ttt aag ttt gaa cat ttc agg gag gat tta cct cgg att    768
Leu Thr Asn Phe Lys Phe Glu His Phe Arg Glu Asp Leu Pro Arg Ile
                245                 250                 255 atg aat cat aaa atc aag aca aat tta cgg ttg agg ttg gag tgc aca    816
Met Asn His Lys Ile Lys Thr Asn Leu Arg Leu Arg Leu Glu Cys Thr
            260                 265                 270 att tat cgt aga cac cgc cct gaa gta gac cca aac acg ggg aag aaa    864
Ile Tyr Arg Arg His Arg Pro Glu Val Asp Pro Asn Thr Gly Lys Lys
            275                 280                 285 ata tgt gtg gtg gaa aaa cta agc aca cac cac att ttg aac gaa gtg    912
Ile Cys Val Val Glu Lys Leu Ser Thr His His Ile Leu Asn Glu Val
            290                 295                 300 acc atc gat cgt ggt cca agt cct ttt cta tcc atg tta gaa ttg tat    960
Thr Ile Asp Arg Gly Pro Ser Pro Phe Leu Ser Met Leu Glu Leu Tyr
305                 310                 315                 320 ggt gac ggc tca tta atg acc gtt gcg cag gcg gac gga ctg att gct   1008
Gly Asp Gly Ser Leu Met Thr Val Ala Gln Ala Asp Gly Leu Ile Ala
                325                 330                 335 gct act ccg act ggg tcc acg gcc tat tct ttg agt gca ggt ggg tca   1056
Ala Thr Pro Thr Gly Ser Thr Ala Tyr Ser Leu Ser Ala Gly Gly Ser
            340                 345                 350 ttg gta tgc cca acc gtc aat gca atc gct tta aca ccc att tgt cca   1104
Leu Val Cys Pro Thr Val Asn Ala Ile Ala Leu Thr Pro Ile Cys Pro
            355                 360                 365 cat gca ttg agt ttc aga ccc atc atc tta cca gaa agt ata aat tta   1152
His Ala Leu Ser Phe Arg Pro Ile Ile Leu Pro Glu Ser Ile Asn Leu
            370                 375                 380 aaa gtg aaa gtc tcg atg aag tca agg gct cca gca tgg gcg gct ttt   1200
Lys Val Lys Val Ser Met Lys Ser Arg Ala Pro Ala Trp Ala Ala Phe
385                 390                 395                 400 gat ggg aaa gat aga att gaa ttg caa aaa ggt gat ttt ata acc ata   1248
Asp Gly Lys Asp Arg Ile Glu Leu Gln Lys Gly Asp Phe Ile Thr Ile
                405                 410                 415 tgc gcc agc cca tat gct ttt cca acc gtg gaa gcc tcg ccc gat gag   1296
Cys Ala Ser Pro Tyr Ala Phe Pro Thr Val Glu Ala Ser Pro Asp Glu
            420                 425                 430 ttt att aac agt atc agt cga caa cta aac tgg aat gtg agg gaa caa   1344
Phe Ile Asn Ser Ile Ser Arg Gln Leu Asn Trp Asn Val Arg Glu Gln
            435                 440                 445 caa aag tcc ttt acg cat att ttg tcc caa aag aac caa gaa aaa tat   1392
Gln Lys Ser Phe Thr His Ile Leu Ser Gln Lys Asn Gln Glu Lys Tyr
            450                 455                 460 gca cat gag gcg aac aaa gtc aga aat caa gca gaa cct tta gag gta   1440
Ala His Glu Ala Asn Lys Val Arg Asn Gln Ala Glu Pro Leu Glu Val
465                 470                 475                 480
```

```
ata aga gat aaa tac tct ctg gaa gca gac gct act aag gaa aac aac    1488
Ile Arg Asp Lys Tyr Ser Leu Glu Ala Asp Ala Thr Lys Glu Asn Asn
            485                 490                 495 aac gga agc gat gat gag agc gac gat gag agt gta aac tgc gaa gct    1536
Asn Gly Ser Asp Asp Glu Ser Asp Asp Glu Ser Val Asn Cys Glu Ala
        500                 505                 510 tgc aaa tta aag cct tcg agc gtc cca aaa cct tct caa gca agg ttt    1584
Cys Lys Leu Lys Pro Ser Ser Val Pro Lys Pro Ser Gln Ala Arg Phe
        515                 520                 525 tca gta taa                                                        1593
Ser Val
    530

<210> SEQ ID NO 2
<211> LENGTH: 530
<212> TYPE: PRT
<213> ORGANISM: Saccharomyces cerevisiae

<400> SEQUENCE: 2

Met Lys Glu Asn Asp Met Asn Asn Gly Val Asp Lys Trp Val Asn Glu
1               5                   10                  15

Glu Asp Gly Arg Asn Asp His His Asn Asn Asn Asn Leu Met Lys
            20                  25                  30

Lys Ala Met Met Asn Asn Glu Gln Ile Asp Arg Thr Gln Asp Ile Asp
        35                  40                  45

Asn Ala Lys Glu Met Leu Arg Lys Ile Ser Ser Glu Ser Ser Ser Arg
    50                  55                  60

Arg Ser Ser Leu Leu Asn Lys Asp Ser Ser Leu Val Asn Gly Asn Ala
65                  70                  75                  80

Asn Ser Gly Gly Gly Thr Ser Ile Asn Gly Thr Arg Gly Ser Ser Lys
                85                  90                  95

Ser Ser Asn Thr His Phe Gln Tyr Ala Ser Thr Ala Tyr Gly Val Arg
            100                 105                 110

Met Leu Ser Lys Asp Ile Ser Asn Thr Lys Val Glu Leu Asp Val Glu
        115                 120                 125

Asn Leu Met Ile Val Thr Lys Leu Asn Asp Val Ser Leu Tyr Phe Leu
    130                 135                 140

Thr Arg Glu Leu Val Glu Trp Val Leu Val His Phe Pro Arg Val Thr
145                 150                 155                 160

Val Tyr Val Asp Ser Glu Leu Lys Asn Ser Lys Phe Ala Ala Gly
                165                 170                 175

Glu Leu Cys Glu Asp Ser Lys Cys Arg Glu Ser Arg Ile Lys Tyr Trp
            180                 185                 190

Thr Lys Asp Phe Ile Arg Glu His Asp Val Phe Phe Asp Leu Val Val
        195                 200                 205

Thr Leu Gly Gly Asp Gly Thr Val Leu Phe Val Ser Ser Ile Phe Gln
    210                 215                 220

Arg His Val Pro Pro Val Met Ser Phe Ser Leu Gly Ser Leu Gly Phe
225                 230                 235                 240

Leu Thr Asn Phe Lys Phe Glu His Phe Arg Glu Asp Leu Pro Arg Ile
                245                 250                 255

Met Asn His Lys Ile Lys Thr Asn Leu Arg Leu Arg Leu Glu Cys Thr
            260                 265                 270

Ile Tyr Arg Arg His Arg Pro Glu Val Asp Pro Asn Thr Gly Lys Lys
        275                 280                 285
```

```
Ile Cys Val Val Glu Lys Leu Ser Thr His His Ile Leu Asn Glu Val
290                 295                 300

Thr Ile Asp Arg Gly Pro Ser Pro Phe Leu Ser Met Leu Glu Leu Tyr
305                 310                 315                 320

Gly Asp Gly Ser Leu Met Thr Val Ala Gln Ala Asp Gly Leu Ile Ala
                325                 330                 335

Ala Thr Pro Thr Gly Ser Thr Ala Tyr Ser Leu Ser Ala Gly Gly Ser
            340                 345                 350

Leu Val Cys Pro Thr Val Asn Ala Ile Ala Leu Thr Pro Ile Cys Pro
        355                 360                 365

His Ala Leu Ser Phe Arg Pro Ile Ile Leu Pro Glu Ser Ile Asn Leu
370                 375                 380

Lys Val Lys Val Ser Met Lys Ser Arg Ala Pro Ala Trp Ala Ala Phe
385                 390                 395                 400

Asp Gly Lys Asp Arg Ile Glu Leu Gln Lys Gly Asp Phe Ile Thr Ile
                405                 410                 415

Cys Ala Ser Pro Tyr Ala Phe Pro Thr Val Glu Ala Ser Pro Asp Glu
            420                 425                 430

Phe Ile Asn Ser Ile Ser Arg Gln Leu Asn Trp Asn Val Arg Glu Gln
        435                 440                 445

Gln Lys Ser Phe Thr His Ile Leu Ser Gln Lys Asn Gln Glu Lys Tyr
450                 455                 460

Ala His Glu Ala Asn Lys Val Arg Asn Gln Ala Glu Pro Leu Glu Val
465                 470                 475                 480

Ile Arg Asp Lys Tyr Ser Leu Glu Ala Asp Ala Thr Lys Glu Asn Asn
                485                 490                 495

Asn Gly Ser Asp Asp Glu Ser Asp Glu Ser Val Asn Cys Glu Ala
            500                 505                 510

Cys Lys Leu Lys Pro Ser Ser Val Pro Lys Pro Ser Gln Ala Arg Phe
        515                 520                 525

Ser Val
530
```

<210> SEQ ID NO 3
<211> LENGTH: 1488
<212> TYPE: DNA
<213> ORGANISM: Saccharomyces cerevisiae
<220> FEATURE:
<221> NAME/KEY: CDS
<222> LOCATION: (1)..(1485)

<400> SEQUENCE: 3

```
atg aaa act gat aga tta ctg att aac gct tcc ccg gag aca tgt acc    48
Met Lys Thr Asp Arg Leu Leu Ile Asn Ala Ser Pro Glu Thr Cys Thr
1               5                   10                  15 aag gga gat gct gag atg gat act atg gat act att gac aga atg aca    96
Lys Gly Asp Ala Glu Met Asp Thr Met Asp Thr Ile Asp Arg Met Thr
                20                  25                  30 tca gtt aaa gtt tta gcg gaa ggc aag gta tta agc aac ttc gaa gaa    144
Ser Val Lys Val Leu Ala Glu Gly Lys Val Leu Ser Asn Phe Glu Glu
            35                  40                  45 ccg ggc tta atg agg tgc ggt tat cat gat gca aaa aac tgg gtc aga    192
Pro Gly Leu Met Arg Cys Gly Tyr His Asp Ala Lys Asn Trp Val Arg
        50                  55                  60 aga tta tcg agc gaa aca att gtc ggt gag gac acg agt aat tta tac    240
Arg Leu Ser Ser Glu Thr Ile Val Gly Glu Asp Thr Ser Asn Leu Tyr
65                  70                  75                  80
```

-continued

| | | |
|---|---|---|
| cca ttt tat gtt gat act gca tac gat gta agg cgt ttg aga aag gat<br>Pro Phe Tyr Val Asp Thr Ala Tyr Asp Val Arg Arg Leu Arg Lys Asp<br>                   85                       90                     95 | 288 |
| ctt ata aat gct aag gtt gac ttg cag gtt gaa aac ctg ata ata atc<br>Leu Ile Asn Ala Lys Val Asp Leu Gln Val Glu Asn Leu Ile Ile Ile<br>                   100                     105                    110 | 336 |
| tgc aat att aat gat att tcc act gta ttt ctc atg aga gaa gtg gtg<br>Cys Asn Ile Asn Asp Ile Ser Thr Val Phe Leu Met Arg Glu Val Val<br>               115                     120                    125 | 384 |
| gaa tgg atc tta cgc aat ttc cat tca ata act gta tat gta caa gat<br>Glu Trp Ile Leu Arg Asn Phe His Ser Ile Thr Val Tyr Val Gln Asp<br>      130                     135                    140 | 432 |
| att ttt aaa aag tca act cag ttt gct gtt ggt gac ctc tgc aaa gac<br>Ile Phe Lys Lys Ser Thr Gln Phe Ala Val Gly Asp Leu Cys Lys Asp<br>145                   150                     155                    160 | 480 |
| agc aat tgc agt aaa aac aga gta aag tat tgg tca aaa gaa ttt gtt<br>Ser Asn Cys Ser Lys Asn Arg Val Lys Tyr Trp Ser Lys Glu Phe Val<br>                   165                     170                    175 | 528 |
| aaa aaa cac gat tca ttc ttt gac ttg atg att aca cta ggg ggt gat<br>Lys Lys His Asp Ser Phe Phe Asp Leu Met Ile Thr Leu Gly Gly Asp<br>            180                     185                    190 | 576 |
| gga act gtc ctt ttt gct tca tct ata ttc acg aaa gat gtt ccg ccg<br>Gly Thr Val Leu Phe Ala Ser Ser Ile Phe Thr Lys Asp Val Pro Pro<br>      195                     200                    205 | 624 |
| att gtt cca ttt gcc ctt gga tca tta gga ttt cta aca aat ttt gaa<br>Ile Val Pro Phe Ala Leu Gly Ser Leu Gly Phe Leu Thr Asn Phe Glu<br>      210                     215                    220 | 672 |
| ttt caa aat ttc aaa gaa acg ttg aaa cat atc tta aca gat gag gtt<br>Phe Gln Asn Phe Lys Glu Thr Leu Lys His Ile Leu Thr Asp Glu Val<br>225                   230                     235                    240 | 720 |
| cgt att aat tta cga atg agg ttg caa tgc aaa ctc tac cgt aga aat<br>Arg Ile Asn Leu Arg Met Arg Leu Gln Cys Lys Leu Tyr Arg Arg Asn<br>                   245                     250                    255 | 768 |
| aaa cca gaa att gat gcc gca act ggg aga aaa ata tgt tac atc gat<br>Lys Pro Glu Ile Asp Ala Ala Thr Gly Arg Lys Ile Cys Tyr Ile Asp<br>            260                     265                    270 | 816 |
| ttc atc tcc gaa cat cac gta ttg aac gaa gta acc ata gat aga ggt<br>Phe Ile Ser Glu His His Val Leu Asn Glu Val Thr Ile Asp Arg Gly<br>               275                     280                    285 | 864 |
| cca gct cct tgt tta tcc cta tta gaa ctc tat gga aac gac tca cta<br>Pro Ala Pro Cys Leu Ser Leu Leu Glu Leu Tyr Gly Asn Asp Ser Leu<br>      290                     295                    300 | 912 |
| atg act aag gtt cag gga gat gga ttg att gtt gcc acg cct acg gga<br>Met Thr Lys Val Gln Gly Asp Gly Leu Ile Val Ala Thr Pro Thr Gly<br>305                   310                     315                    320 | 960 |
| tcc acg gca tac tca ttg agt gca gga ggc tct tta ata tcg cca agc<br>Ser Thr Ala Tyr Ser Leu Ser Ala Gly Gly Ser Leu Ile Ser Pro Ser<br>                   325                     330                    335 | 1008 |
| gta aat gcc ata gcg gtg acg cct ata tgt cct cat act ttg agc ttt<br>Val Asn Ala Ile Ala Val Thr Pro Ile Cys Pro His Thr Leu Ser Phe<br>            340                     345                    350 | 1056 |
| agg cct ata att tta cca gat agc atg gaa tta aaa gtt aga gta gat<br>Arg Pro Ile Ile Leu Pro Asp Ser Met Glu Leu Lys Val Arg Val Asp<br>               355                     360                    365 | 1104 |
| atg aac tca aga ggg acg tcg tgg gtg aat ttt gac gga aaa gat aga<br>Met Asn Ser Arg Gly Thr Ser Trp Val Asn Phe Asp Gly Lys Asp Arg<br>      370                     375                     380 | 1152 |
| gtt gaa ttg aaa cag ggt gac tat gtt gtg ata act gca agc ccc tat<br>Val Glu Leu Lys Gln Gly Asp Tyr Val Val Ile Thr Ala Ser Pro Tyr<br>385                   390                     395                    400 | 1200 |

```
tcg gta ccg act atc gag tca tct gcc agt gaa ttt ttt gaa agt atc    1248
Ser Val Pro Thr Ile Glu Ser Ser Ala Ser Glu Phe Phe Glu Ser Ile
            405                 410                 415 agt aaa aat ctt aat tgg aat gac cgc gaa gag cag aag cca ttt gca    1296
Ser Lys Asn Leu Asn Trp Asn Asp Arg Glu Glu Gln Lys Pro Phe Ala
        420                 425                 430 cat att ctc tcg cca aaa aat caa gaa aaa tat aga tta gac tca tcg    1344
His Ile Leu Ser Pro Lys Asn Gln Glu Lys Tyr Arg Leu Asp Ser Ser
    435                 440                 445 aaa aat gga aac gac acc ata agt aat ccc ctc gag agt tca tgc ata    1392
Lys Asn Gly Asn Asp Thr Ile Ser Asn Pro Leu Glu Ser Ser Cys Ile
450                 455                 460 agc tca gat gca caa gat gag gag agg aaa tcc gta acg gaa aca gaa    1440
Ser Ser Asp Ala Gln Asp Glu Glu Arg Lys Ser Val Thr Glu Thr Glu
465                 470                 475                 480 aca gaa ata gtt gtt gaa cgg act cgt cag gct cat ttt gca atc taa    1488
Thr Glu Ile Val Val Glu Arg Thr Arg Gln Ala His Phe Ala Ile
                485                 490                 495

<210> SEQ ID NO 4
<211> LENGTH: 495
<212> TYPE: PRT
<213> ORGANISM: Saccharomyces cerevisiae

<400> SEQUENCE: 4

Met Lys Thr Asp Arg Leu Leu Ile Asn Ala Ser Pro Glu Thr Cys Thr
1               5                   10                  15

Lys Gly Asp Ala Glu Met Asp Thr Met Asp Thr Ile Asp Arg Met Thr
            20                  25                  30

Ser Val Lys Val Leu Ala Glu Gly Lys Val Leu Ser Asn Phe Glu Glu
        35                  40                  45

Pro Gly Leu Met Arg Cys Gly Tyr His Asp Ala Lys Asn Trp Val Arg
    50                  55                  60

Arg Leu Ser Ser Glu Thr Ile Val Gly Glu Asp Thr Ser Asn Leu Tyr
65                  70                  75                  80

Pro Phe Tyr Val Asp Thr Ala Tyr Asp Val Arg Arg Leu Arg Lys Asp
                85                  90                  95

Leu Ile Asn Ala Lys Val Asp Leu Gln Val Glu Asn Leu Ile Ile Ile
            100                 105                 110

Cys Asn Ile Asn Asp Ile Ser Thr Val Phe Leu Met Arg Glu Val Val
        115                 120                 125

Glu Trp Ile Leu Arg Asn Phe His Ser Ile Thr Val Tyr Val Gln Asp
    130                 135                 140

Ile Phe Lys Lys Ser Thr Gln Phe Ala Val Gly Asp Leu Cys Lys Asp
145                 150                 155                 160

Ser Asn Cys Ser Lys Asn Arg Val Lys Tyr Trp Ser Lys Glu Phe Val
                165                 170                 175

Lys Lys His Asp Ser Phe Phe Asp Leu Met Ile Thr Leu Gly Gly Asp
            180                 185                 190

Gly Thr Val Leu Phe Ala Ser Ser Ile Phe Thr Lys Asp Val Pro Pro
        195                 200                 205

Ile Val Pro Phe Ala Leu Gly Ser Leu Gly Phe Leu Thr Asn Phe Glu
    210                 215                 220

Phe Gln Asn Phe Lys Glu Thr Leu Lys His Ile Leu Thr Asp Glu Val
225                 230                 235                 240

Arg Ile Asn Leu Arg Met Arg Leu Gln Cys Lys Leu Tyr Arg Arg Asn
```

```
                     245                 250                 255
Lys Pro Glu Ile Asp Ala Ala Thr Gly Arg Lys Ile Cys Tyr Ile Asp
                 260                 265                 270

Phe Ile Ser Glu His His Val Leu Asn Glu Val Thr Ile Asp Arg Gly
             275                 280                 285

Pro Ala Pro Cys Leu Ser Leu Glu Leu Tyr Gly Asn Asp Ser Leu
         290                 295                 300

Met Thr Lys Val Gln Gly Asp Gly Leu Ile Val Ala Thr Pro Thr Gly
305                 310                 315                 320

Ser Thr Ala Tyr Ser Leu Ser Ala Gly Gly Ser Leu Ile Ser Pro Ser
                 325                 330                 335

Val Asn Ala Ile Ala Val Thr Pro Ile Cys Pro His Thr Leu Ser Phe
                 340                 345                 350

Arg Pro Ile Ile Leu Pro Asp Ser Met Glu Leu Lys Val Arg Val Asp
                 355                 360                 365

Met Asn Ser Arg Gly Thr Ser Trp Val Asn Phe Asp Gly Lys Asp Arg
370                 375                 380

Val Glu Leu Lys Gln Gly Asp Tyr Val Val Ile Thr Ala Ser Pro Tyr
385                 390                 395                 400

Ser Val Pro Thr Ile Glu Ser Ser Ala Ser Glu Phe Phe Glu Ser Ile
                 405                 410                 415

Ser Lys Asn Leu Asn Trp Asn Asp Arg Glu Glu Gln Lys Pro Phe Ala
                 420                 425                 430

His Ile Leu Ser Pro Lys Asn Gln Glu Lys Tyr Arg Leu Asp Ser Ser
                 435                 440                 445

Lys Asn Gly Asn Asp Thr Ile Ser Asn Pro Leu Glu Ser Ser Cys Ile
                 450                 455                 460

Ser Ser Asp Ala Gln Asp Glu Glu Arg Lys Ser Val Thr Glu Thr Glu
465                 470                 475                 480

Thr Glu Ile Val Val Glu Arg Thr Arg Gln Ala His Phe Ala Ile
                 485                 490                 495

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caccgtttaa actctagaat gaaggagaat gacatgaata at                         42

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtttaaacgg atccttatac tgaaaacctt gcttgaga                              38

<210> SEQ ID NO 7
<211> LENGTH: 43
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 7
caccgtttaa actctagaat gaaaactgat agattactga tta                           43

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtttaaacga gctcttagat tgcaaaatga gcctgac                                  37

<210> SEQ ID NO 9
<211> LENGTH: 2052
<212> TYPE: DNA
<213> ORGANISM: Pichia stipitis

<400> SEQUENCE: 9
gatccacaga cactaattgg ttctacatta ttcgtgttca gacacaaacc ccagcgttgg      60
cggtttctgt ctgcgttcct ccagcacctt cttgctcaac cccagaaggt gcacactgca     120
gacacacata catacgagaa cctggaacaa atatcggtgt cggtgaccga atgtgcaaa      180 cccagacacg actaataaac ctggcagctc caataccgcc gacaacaggt gaggtgaccg     240
atggggtgcc aattaatgtc tgaaaattgg ggtatataaa tatggcgatt ctccggagaa     300
tttttcagtt ttcttttcat ttctccagta ttcttttcta tacaactata ctacaatgcc     360
ttctattaag ttgaactctg gttacgacat gccagccgtc ggtttcggct gttggaaagt     420
cgacgtcgac acctgttctg aacagatcta ccgtgctatc aagaccggtt acagattgtt     480
cgacggtgcc gaagattacg ccaacgaaaa gttagttggt gccggtgtca agaaggccat     540
tgacgaaggt atcgtcaagc gtgaagactt gttccttacc tccaagttgt ggaacaacta     600
ccaccaccca gacaacgtcg aaaaggcctt gaacagaacc ctttctgact gcaagttga     660 ctacgttgac ttgttcttga tccacttccc agtcaccttc aagttcgttc cattagaaga     720
aaagtaccca ccaggattct actgtggtaa gggtgacaac ttcgactacg aagatgttcc     780
aattttagag acctggaagg ctcttgaaaa gttggtcaag gccggtaaga tcagatctat     840
cggtgtttct aacttcccag gtgctttgct cttggacttg ttgagaggtg ctaccatcaa     900
gccatctgtc ttgcaagttg aacaccaccc atacttgcaa caaccaagat tgatcgaatt     960
cgctcaatcc cgtggtattg ctgtcaccgc ttactcttcg ttcggtcctc aatctttcgt    1020
tgaattgaac caaggtagag ctttgaacac ttctccattg ttcgagaacg aaactatcaa    1080
ggctatcgct gctaagcacg gtaagtctcc agctcaagtc ttgttgagat ggtcttccca    1140
aagaggcatt gccatcattc caaagtccaa cactgtccca agattgttgg aaaacaagga    1200
cgtcaacagc ttcgacttgg acgaacaaga tttcgctgac attgccaagt ggacatcaa    1260 cttgagattc aacgacccat gggactggga caagattcct atcttcgtct aagaaggttg    1320
ctttatagag aggaaataaa acctaatata cattgattgt acatttaaaa ttgaatattg    1380
tagctagcag attcggaaat ttaaaatggg aaggtgattc tatccgtacg aatgatctct    1440
atgtacatac acgttgaaga tagcagtaca gtagacatca agtctacaga tcattaaaca    1500
tatcttaaat tgtagaaaac tataaacttt tcaattcaaa ccatgtctgc caaggaatca    1560

-continued

```
aatgagattt ttttcgcagc caaacttgaa tccaaaaata aaaacgtca ttgtctgaaa    1620 caactctatc ttatctttca cctcatcaat tcattgcata tcataaaagc ctccgatagc    1680
atacaaaact acttctgcat catatctaaa tcatagtgcc atattcagta acaataccgg    1740
taagaaactt ctattttttt agtctgcctt aacgagatgc agatcgatgc aacgtaagat    1800
caaacccctc cagttgtaca gtcagtcata tagtgaacac cgtacaatat ggtatctacg    1860
ttcaaataga ctccaataca gctggtctgc ccaagttgag caactttaat ttagagacaa    1920
agtcgtctct gttgatgtag gcaccacaca ttcttctctt gcccgtgaac tctgttctgg    1980
agtggaaaca tctccagttg tcaaatatca aacactgacc aggcttcaac tggtagaaga    2040
tttcgttttc gg                                                        2052
```

<210> SEQ ID NO 10
<211> LENGTH: 318
<212> TYPE: PRT
<213> ORGANISM: Pichia stipitis

<400> SEQUENCE: 10

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
```

```
            275                 280                 285
Asp Glu Gln Asp Phe Ala Asp Ile Ala Lys Leu Asp Ile Asn Leu Arg
            290                 295                 300

Phe Asn Asp Pro Trp Asp Trp Asp Lys Ile Pro Ile Phe Val
305                 310                 315

<210> SEQ ID NO 11
<211> LENGTH: 2170
<212> TYPE: DNA
<213> ORGANISM: Pichia stipitis

<400> SEQUENCE: 11
ctgcagccca gcttgatatc gaattggtgg acaagtgtgt gggtgaattt gtatatgcaa      60
aaggagctac acttctactt tttaaggctc aaacaacttg cggagctcgt ggtaactctg     120
ctcttgtaga gtttgatatc tctattttga tcttagtatt tgtattgtag ctgtcgtata     180
ttattcactt agtgtgagt ctcattatca agagaactcg agaatggtgg gctcatcttc      240 ggccttttt tgcaagtcaa caattctcac tcttccaata atacgaacac actatctaga     300
ccaccctaag tcgtccctat gtcgtatgtt tgcctctact acaaagttac tagcaaatat     360
ccgcagcaac aacagctgcc ctcttccagc ttcttagtgt gttggccgaa aaggcgcttt     420
cgggctccag cttctgtcct ctgcggctgc tgcacataac gcgggacaa tgacttctcc      480 agcttttatt ataaaaggag ccatctcctc caggtgaaaa attacgatca acttttactc     540
ttttccattg tctcttgtgt atcctcactt tagtttgttt caatcacccc taatactctt     600
cacacaatta aaatgactgc taacccttcc ttggtgttga acaagatcga cgacatttcg     660
ttcgaaactt acgatgcccc agaaatctct gaacctaccg atgtcctcgt ccaggtcaag     720
aaaaccggta tctgtggttc cgacatccac ttctacgccc atggtagaat cggtaacttc     780
gttttgacca agccaatggt cttgggtcac gaatccgccg tactgttgt ccaggttggt      840 aagggtgtca cctctcttaa ggttggtgac aacgtcgcta tcgaaccagg tattccatcc     900
agattctccg acgaatacaa gagcggtcac tacaacttgt gtcctcacat ggccttcgcc     960
gctactccta actccaagga aggcgaacca aacccaccag gtaccttatg taagtacttc    1020
aagtcgccag aagacttctt ggtcaagttg ccagaccacg tcagcttgga actcggtgct    1080
cttgttgagc cattgtctgt tggtgtccac gcctctaagt tgggttccgt tgctttcggc    1140
gactacgttg ccgtctttgg tgctggtcct gttggtcttt tggctgctgc tgtcgccaag    1200
accttcggtg ctaagggtgt catcgtcgtt gacattttcg acaacaagtt gaagatggcc    1260
aaggacattg gtgctgctac tcacaccttc aactccaaga ccggtggttc tgaagaattg    1320
atcaaggctt tcggtggtaa cgtgccaaac gtcgttttgg aatgtactgg tgctgaacct    1380
tgtatcaagt tgggtgttga cgccattgcc ccaggtggtc gtttcgttca agtcggtaac    1440
gctgctggtc cagtcagctt cccaatcacc gttttcgcca tgaaggaatt gacttttgttc   1500 ggttcttttca gatacggatt caacgactac aagactgctg ttggaatctt tgacactaac    1560
taccaaaacg gtagagaaaa tgctccaatt gactttgaac aattgatcac ccacagatac    1620
aagttcaagg acgctattga agcctacgac ttggtcagag ccggtaaggg tgctgtcaag    1680
tgtctcattg acggccctga gtaagtcaac cgcttggctg gcccaaagtg aaccagaaac    1740
gaaaatgatt atcaaatagc tttatagacc tttatccaaa tttatgtaaa ctaatagaaa    1800
agacagtgta gaagttatat ggttgcatca cgtgagtttt ttgaattctt gaaagtgaag    1860
tcttggtcgg aacaaacaaa caaaaaaata ttttcagcaa gagttgattt cttttctgga    1920
```

-continued

```
gattttggta attggcagag aacccctttc tgctattgcc atctaaacat ctttgaatag    1980
aactttactg gatggccgcc tagtgttgag tatatattat caaccaaaat cctgtatata    2040
gtctctgaaa aatttgacta tcctaactta acaaagagc accataatgc aagctcatag     2100
ttcttagaga caccaactat acttagccaa acaaatgtc cttggcctct aaagaagcat     2160
tcagcaagct                                                           2170

<210> SEQ ID NO 12
<211> LENGTH: 363
<212> TYPE: PRT
<213> ORGANISM: Pichia stipitis

<400> SEQUENCE: 12

Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Asp Ile
        195                 200                 205

Phe Asp Asn Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320
```

Arg Glu Asn Ala Pro Ile Asp Phe Glu Gln Leu Ile Thr His Arg Tyr
            325                 330                 335

Lys Phe Lys Asp Ala Ile Glu Ala Tyr Asp Leu Val Arg Ala Gly Lys
        340                 345                 350

Gly Ala Val Lys Cys Leu Ile Asp Gly Pro Glu
        355                 360

<210> SEQ ID NO 13
<211> LENGTH: 1803
<212> TYPE: DNA
<213> ORGANISM: Pichia stipitis

<400> SEQUENCE: 13

| | | |
|---|---|---|
| atgttgtgtt cagtaattca gagacagaca agagaggttt ccaacacaat gtctttagac | 60 |
| tcatactatc ttgggtttga tctttcgacc caacaactga aatgtctcgc cattaaccag | 120 |
| gacctaaaaa ttgtccattc agaaacagtg gaatttgaaa aggatcttcc gcattatcac | 180 |
| acaaagaagg gtgtctatat acacggcgac actatcgaat gtcccgtagc catgtggtta | 240 |
| gaggctctag atctggttct ctcgaaatat cgcgaggcta aatttccatt gaacaaagtt | 300 |
| atggccgtct cagggtcctg ccagcagcac gggtctgtct actggtcctc ccaagccgaa | 360 |
| tctctgttag agcaattgaa taagaaaccg gaaaagatt tattgcacta cgtgagctct | 420 |
| gtagcatttg caaggcaaac cgcccccaat tggcaagacc acagtactgc aaagcaatgt | 480 |
| caagagtttg aagagtgcat aggtgggcct gaaaaaatgg ctcaattaac agggtccaga | 540 |
| gcccatttta gatttactgg tcctcaaatt ctgaaaattg cacaattaga accagaagct | 600 |
| tacgaaaaaa caaagaccat ttctttagtg tctaattttt tgacttctat cttagtgggc | 660 |
| catcttgttg aattagagga ggcagatgcc tgtggtatga acctttatga tatacgtgaa | 720 |
| agaaaattca gtgatgagct actacatcta attgatagtt cttctaagga taaaactatc | 780 |
| agacaaaaat taatgagagc acccatgaaa aatttgatag cgggtaccat ctgtaaatat | 840 |
| tttattgaga gtacggtttt caatacaaac tgcaaggtct ctcccatgac tggggataat | 900 |
| ttagccacta tatgttcttt accctgcgg aagaatgacg ttctcgtttc cctaggaaca | 960 |
| agtactacag ttcttctggt caccgataag tatcacccct ctccgaacta tcatcttttc | 1020 |
| attcatccaa ctctgccaaa ccattatatg ggtatgattt gttattgtaa tggttctttg | 1080 |
| gcaagggaga ggataagaga cgagttaaac aaagaacggg aaaataatta tgagaagact | 1140 |
| aacgattgga ctcttttaa tcaagctgtg ctagatgact cagaaagtag tgaaaatgaa | 1200 |
| ttaggtgtat atttcctct gggggagatc gttcctagcg taaaagccat aaacaaaagg | 1260 |
| gttatcttca atccaaaaac gggtatgatt gaaagagagg tggccaagtt caaagacaag | 1320 |
| aggcacgatg ccaaaaatat tgtagaatca caggctttaa gttgcagggt aagaatatct | 1380 |
| cccctgcttt cggattcaaa cgcaagctca caacagagac tgaacgaaga tacaatcgtg | 1440 |
| aagtttgatt acgatgaatc tccgctgcgg gactacctaa ataaaaggcc agaaaggact | 1500 |
| tttttttgtag gtggggcttc taaaaacgat gctattgtga agaagtttgc tcaagtcatt | 1560 |
| ggtgctacaa agggtaattt taggctagaa acaccaaact catgtgccct tggtggttgt | 1620 |
| tataaggcca tgtggtcatt gttatatgac tctaataaaa ttgcagttcc ttttgataaa | 1680 |
| tttctgaatg acaatttcc atggcatgta atggaaagca tatccgatgt ggataatgaa | 1740 |
| aattgggatc gctataattc caagattgtc cccttaagcg aactggaaaa gactctcatc | 1800 |
| taa | 1803 |

<210> SEQ ID NO 14
<211> LENGTH: 600
<212> TYPE: PRT
<213> ORGANISM: Pichia stipitis

<400> SEQUENCE: 14

```
Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205

Leu Val Ser Asn Phe Leu Thr Ser Ile Leu Val Gly His Leu Val Glu
    210                 215                 220

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
                245                 250                 255

Asp Lys Thr Ile Arg Gln Lys Leu Met Arg Ala Pro Met Lys Asn Leu
            260                 265                 270

Ile Ala Gly Thr Ile Cys Lys Tyr Phe Ile Glu Lys Tyr Gly Phe Asn
        275                 280                 285

Thr Asn Cys Lys Val Ser Pro Met Thr Gly Asp Asn Leu Ala Thr Ile
    290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
                325                 330                 335

Tyr His Leu Phe Ile His Pro Thr Leu Pro Asn His Tyr Met Gly Met
            340                 345                 350

Ile Cys Tyr Cys Asn Gly Ser Leu Ala Arg Glu Arg Ile Arg Asp Glu
        355                 360                 365

Leu Asn Lys Glu Arg Glu Asn Asn Tyr Glu Lys Thr Asn Asp Trp Thr
    370                 375                 380
```

```
Leu Phe Asn Gln Ala Val Leu Asp Asp Ser Glu Ser Glu Asn Glu
385                 390                 395                 400

Leu Gly Val Tyr Phe Pro Leu Gly Glu Ile Val Pro Ser Val Lys Ala
            405                 410                 415

Ile Asn Lys Arg Val Ile Phe Asn Pro Lys Thr Gly Met Ile Glu Arg
        420                 425                 430

Glu Val Ala Lys Phe Lys Asp Lys Arg His Asp Ala Lys Asn Ile Val
    435                 440                 445

Glu Ser Gln Ala Leu Ser Cys Arg Val Arg Ile Ser Pro Leu Leu Ser
450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
                485                 490                 495

Pro Glu Arg Thr Phe Phe Val Gly Gly Ala Ser Lys Asn Asp Ala Ile
            500                 505                 510

Val Lys Lys Phe Ala Gln Val Ile Gly Ala Thr Lys Gly Asn Phe Arg
        515                 520                 525

Leu Glu Thr Pro Asn Ser Cys Ala Leu Gly Gly Cys Tyr Lys Ala Met
    530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
                565                 570                 575

Val Asp Asn Glu Asn Trp Asp Arg Tyr Asn Ser Lys Ile Val Pro Leu
            580                 585                 590

Ser Glu Leu Glu Lys Thr Leu Ile
        595                 600

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctacgcaaag agaacggag                                                19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcaatcaata ggaagacagg                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
```

```
atgtcacgct tacattcacg                                           20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tggttgtaac actggcagag                                           20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agcgttgtga aagggaaatg                                           20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgtcgtcaa gagtggtacc                                           20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcttcgacac tgcaaacgac                                           20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tctacatgag catgccctgc                                           20

<210> SEQ ID NO 23
<211> LENGTH: 2010
<212> TYPE: DNA
<213> ORGANISM: Saccharomyces cerevisiae
<220> FEATURE:
<221> NAME/KEY: CDS
<222> LOCATION: (1)..(2007)

<400> SEQUENCE: 23
```

```
atg agt aat cct caa aaa gct cta aac gac ttt ctg tcc agt gaa tct         48
Met Ser Asn Pro Gln Lys Ala Leu Asn Asp Phe Leu Ser Ser Glu Ser
1               5                   10                  15 gtt cat aca cat gat agt tct agg aaa caa tct aat aag cag tca tcc         96
Val His Thr His Asp Ser Ser Arg Lys Gln Ser Asn Lys Gln Ser Ser
            20                  25                  30 gac gaa gga cgc tct tca tca caa cct tca cat cat cac tct ggt ggt       144
Asp Glu Gly Arg Ser Ser Ser Gln Pro Ser His His His Ser Gly Gly
        35                  40                  45 act aac aac aat aat aac aat aat aat aat aat aac agt aac aac           192
Thr Asn Asn Asn Asn Asn Asn Asn Asn Asn Asn Asn Ser Asn Asn
    50                  55                  60 aac aac aac ggc aac gat ggg gga aat gat gac gac tat gat tat gaa       240
Asn Asn Asn Gly Asn Asp Gly Gly Asn Asp Asp Asp Tyr Asp Tyr Glu
65              70                  75                  80 atg caa gat tat aga cct tct ccg caa agt gcg cgg cct act ccc acg       288
Met Gln Asp Tyr Arg Pro Ser Pro Gln Ser Ala Arg Pro Thr Pro Thr
                85                  90                  95 tat gtt cca caa tat tct gta gaa agt ggg act gct ttc ccg att caa       336
Tyr Val Pro Gln Tyr Ser Val Glu Ser Gly Thr Ala Phe Pro Ile Gln
                100                 105                 110 gag gtt att cct agc gca tac att aac aca caa gat ata aac cat aaa       384
Glu Val Ile Pro Ser Ala Tyr Ile Asn Thr Gln Asp Ile Asn His Lys
            115                 120                 125 gat aac ggt ccg ccg agt gca agc agt aat aga gca ttc agg cct aga       432
Asp Asn Gly Pro Pro Ser Ala Ser Ser Asn Arg Ala Phe Arg Pro Arg
        130                 135                 140 ggg cag acc aca gtg tcg gcc aac gtg ctt aac att gaa gat ttt tac       480
Gly Gln Thr Thr Val Ser Ala Asn Val Leu Asn Ile Glu Asp Phe Tyr
145                 150                 155                 160 aaa aat gca gac gat gcg cat acc atc ccg gag tca cat tta tcg aga       528
Lys Asn Ala Asp Asp Ala His Thr Ile Pro Glu Ser His Leu Ser Arg
                165                 170                 175 agg aga agt agg tcg agg gct acg agt aat gct ggg cac agt gcc aat       576
Arg Arg Ser Arg Ser Arg Ala Thr Ser Asn Ala Gly His Ser Ala Asn
                180                 185                 190 aca ggc gcc acg aat ggc agg act act ggt gcc caa act aat atg gaa       624
Thr Gly Ala Thr Asn Gly Arg Thr Thr Gly Ala Gln Thr Asn Met Glu
            195                 200                 205 agc aat gaa tca cca cgt aac gtc ccc att atg gtg aag cca aag aca       672
Ser Asn Glu Ser Pro Arg Asn Val Pro Ile Met Val Lys Pro Lys Thr
        210                 215                 220 tta tac cag aac cct caa aca cct aca gtc ttg ccc tcc aca tac cat       720
Leu Tyr Gln Asn Pro Gln Thr Pro Thr Val Leu Pro Ser Thr Tyr His
225                 230                 235                 240 cca att aat aaa tgg tct tcc gtc aaa aac act tat ttg aag gaa ttt       768
Pro Ile Asn Lys Trp Ser Ser Val Lys Asn Thr Tyr Leu Lys Glu Phe
                245                 250                 255 tta gcc gag ttt atg gga aca atg gtt atg att att ttc ggt agt gct       816
Leu Ala Glu Phe Met Gly Thr Met Val Met Ile Ile Phe Gly Ser Ala
                260                 265                 270 gtt gtt tgt cag gtc aat gtt gct ggg aaa ata cag cag gac aat ttc       864
Val Val Cys Gln Val Asn Val Ala Gly Lys Ile Gln Gln Asp Asn Phe
            275                 280                 285 aac gtg gct ttg gat aac ctt aac gtt acc ggg tct tct gca gaa acg       912
Asn Val Ala Leu Asp Asn Leu Asn Val Thr Gly Ser Ser Ala Glu Thr
        290                 295                 300 ata gac gct atg aag agt tta aca tcc ttg gtt tca tcc gtt gcg ggc       960
Ile Asp Ala Met Lys Ser Leu Thr Ser Leu Val Ser Ser Val Ala Gly
305                 310                 315                 320
```

```
ggt acc ttt gat gat gtg gca ttg ggc tgg gct gct gcc gtg gtg atg      1008
Gly Thr Phe Asp Asp Val Ala Leu Gly Trp Ala Ala Ala Val Val Met
            325                 330                 335 ggc tat ttc tgc gct ggt ggt agt gcc atc tca ggt gct cat ttg aat      1056
Gly Tyr Phe Cys Ala Gly Gly Ser Ala Ile Ser Gly Ala His Leu Asn
        340                 345                 350 ccg tct att aca tta gcc aat ttg gtg tat aga ggt ttt ccc ctg aag      1104
Pro Ser Ile Thr Leu Ala Asn Leu Val Tyr Arg Gly Phe Pro Leu Lys
    355                 360                 365 aaa gtt cct tat tac ttt gct gga caa ttg atc ggt gcc ttc aca ggc      1152
Lys Val Pro Tyr Tyr Phe Ala Gly Gln Leu Ile Gly Ala Phe Thr Gly
370                 375                 380 gct ttg atc ttg ttt att tgg tac aaa agg gtg tta caa gag gca tat      1200
Ala Leu Ile Leu Phe Ile Trp Tyr Lys Arg Val Leu Gln Glu Ala Tyr
385                 390                 395                 400 agc gat tgg tgg atg aat gaa agt gtt gcg gga atg ttt tgc gtt ttt      1248
Ser Asp Trp Trp Met Asn Glu Ser Val Ala Gly Met Phe Cys Val Phe
                405                 410                 415 cca aag cct tat cta agt tca gga cgg caa ttt ttt tcc gaa ttt tta      1296
Pro Lys Pro Tyr Leu Ser Ser Gly Arg Gln Phe Phe Ser Glu Phe Leu
            420                 425                 430 tgt gga gct atg tta caa gca gga aca ttt gcg ctg acc gat cct tat      1344
Cys Gly Ala Met Leu Gln Ala Gly Thr Phe Ala Leu Thr Asp Pro Tyr
        435                 440                 445 acg tgt ttg tcc tct gat gtt ttc cca ttg atg atg ttt att ttg att      1392
Thr Cys Leu Ser Ser Asp Val Phe Pro Leu Met Met Phe Ile Leu Ile
    450                 455                 460 ttc att atc aat gct tcc atg gct tat cag aca ggt aca gca atg aat      1440
Phe Ile Ile Asn Ala Ser Met Ala Tyr Gln Thr Gly Thr Ala Met Asn
465                 470                 475                 480 ttg gct cgt gat ctg ggc cca cgt ctt gca cta tat gca gtt gga ttt      1488
Leu Ala Arg Asp Leu Gly Pro Arg Leu Ala Leu Tyr Ala Val Gly Phe
                485                 490                 495 gat cat aaa atg ctt tgg gtg cat cat cat cat ttc ttt tgg gtt ccc      1536
Asp His Lys Met Leu Trp Val His His His His Phe Phe Trp Val Pro
            500                 505                 510 atg gta ggc cca ttt att ggt gcg tta atg ggg ggt ttg gtt tac gat      1584
Met Val Gly Pro Phe Ile Gly Ala Leu Met Gly Gly Leu Val Tyr Asp
        515                 520                 525 gtc tgt att tat cag ggt cat gaa tct cca gtc aac tgg tct tta cca      1632
Val Cys Ile Tyr Gln Gly His Glu Ser Pro Val Asn Trp Ser Leu Pro
    530                 535                 540 gtt tat aag gaa atg att atg aga gcc tgg ttt aga agg cct ggt tgg      1680
Val Tyr Lys Glu Met Ile Met Arg Ala Trp Phe Arg Arg Pro Gly Trp
545                 550                 555                 560 aag aag aga aat aga gca aga aga aca tcg gac ctg agt gac ttc tca      1728
Lys Lys Arg Asn Arg Ala Arg Arg Thr Ser Asp Leu Ser Asp Phe Ser
                565                 570                 575 tac aat aac gat gat gat gag gaa ttt gga gaa aga atg gct ctt caa      1776
Tyr Asn Asn Asp Asp Asp Glu Glu Phe Gly Glu Arg Met Ala Leu Gln
            580                 585                 590 aag aca aag acc aag tca tct att tca gac aac gaa aat gaa gca gga      1824
Lys Thr Lys Thr Lys Ser Ser Ile Ser Asp Asn Glu Asn Glu Ala Gly
        595                 600                 605 gaa aag aaa gtg caa ttt aaa tct gtt cag cgc ggc aaa aga acg ttt      1872
Glu Lys Lys Val Gln Phe Lys Ser Val Gln Arg Gly Lys Arg Thr Phe
    610                 615                 620 ggt ggt ata cca aca att ctt gaa gaa gaa gat tcc att gaa act gct      1920
Gly Gly Ile Pro Thr Ile Leu Glu Glu Glu Asp Ser Ile Glu Thr Ala
```

```
                   625                 630                 635                 640
tcg cta ggt gcg acg acg act gat tct att ggg tta tcc gac aca tca      1968
Ser Leu Gly Ala Thr Thr Thr Asp Ser Ile Gly Leu Ser Asp Thr Ser
                   645                 650                 655 tca gaa gat tcg cat tat ggt aat gct aag aag gta aca tga              2010
Ser Glu Asp Ser His Tyr Gly Asn Ala Lys Lys Val Thr
                   660                 665
```

<210> SEQ ID NO 24
<211> LENGTH: 669
<212> TYPE: PRT
<213> ORGANISM: Saccharomyces cerevisiae

<400> SEQUENCE: 24

```
Met Ser Asn Pro Gln Lys Ala Leu Asn Asp Phe Leu Ser Ser Glu Ser
1               5                   10                  15

Val His Thr His Asp Ser Ser Arg Lys Gln Ser Asn Lys Gln Ser Ser
            20                  25                  30

Asp Glu Gly Arg Ser Ser Ser Gln Pro Ser His His Ser Gly Gly
        35                  40                  45

Thr Asn Asn Asn Asn Asn Asn Asn Asn Asn Asn Asn Ser Asn Asn
50                  55                  60

Asn Asn Asn Gly Asn Asp Gly Gly Asn Asp Asp Tyr Asp Tyr Glu
65                  70                  75                  80

Met Gln Asp Tyr Arg Pro Ser Pro Gln Ser Ala Arg Pro Thr Pro Thr
                85                  90                  95

Tyr Val Pro Gln Tyr Ser Val Glu Ser Gly Thr Ala Phe Pro Ile Gln
            100                 105                 110

Glu Val Ile Pro Ser Ala Tyr Ile Asn Thr Gln Asp Ile Asn His Lys
        115                 120                 125

Asp Asn Gly Pro Pro Ser Ala Ser Ser Asn Arg Ala Phe Arg Pro Arg
130                 135                 140

Gly Gln Thr Thr Val Ser Ala Asn Val Leu Asn Ile Glu Asp Phe Tyr
145                 150                 155                 160

Lys Asn Ala Asp Asp Ala His Thr Ile Pro Glu Ser His Leu Ser Arg
                165                 170                 175

Arg Arg Ser Arg Ser Arg Ala Thr Ser Asn Ala Gly His Ser Ala Asn
            180                 185                 190

Thr Gly Ala Thr Asn Gly Arg Thr Gly Ala Gln Thr Asn Met Glu
        195                 200                 205

Ser Asn Glu Ser Pro Arg Asn Val Pro Ile Met Val Lys Pro Lys Thr
210                 215                 220

Leu Tyr Gln Asn Pro Gln Thr Pro Thr Val Leu Pro Ser Thr Tyr His
225                 230                 235                 240

Pro Ile Asn Lys Trp Ser Ser Val Lys Asn Thr Tyr Leu Lys Glu Phe
                245                 250                 255

Leu Ala Glu Phe Met Gly Thr Met Val Met Ile Ile Phe Gly Ser Ala
            260                 265                 270

Val Val Cys Gln Val Asn Val Ala Gly Lys Ile Gln Gln Asp Asn Phe
        275                 280                 285

Asn Val Ala Leu Asp Asn Leu Asn Val Thr Gly Ser Ser Ala Glu Thr
290                 295                 300

Ile Asp Ala Met Lys Ser Leu Thr Ser Leu Val Ser Ser Val Ala Gly
305                 310                 315                 320

Gly Thr Phe Asp Asp Val Ala Leu Gly Trp Ala Ala Ala Val Val Met
```

```
                        325                 330                 335
Gly Tyr Phe Cys Ala Gly Gly Ser Ala Ile Ser Gly Ala His Leu Asn
                340                 345                 350
Pro Ser Ile Thr Leu Ala Asn Leu Val Tyr Arg Gly Phe Pro Leu Lys
            355                 360                 365
Lys Val Pro Tyr Tyr Phe Ala Gly Gln Leu Ile Gly Ala Phe Thr Gly
        370                 375                 380
Ala Leu Ile Leu Phe Ile Trp Tyr Lys Arg Val Leu Gln Glu Ala Tyr
385                 390                 395                 400
Ser Asp Trp Trp Met Asn Glu Ser Val Ala Gly Met Phe Cys Val Phe
                405                 410                 415
Pro Lys Pro Tyr Leu Ser Ser Gly Arg Gln Phe Ser Glu Phe Leu
                420                 425                 430
Cys Gly Ala Met Leu Gln Ala Gly Thr Phe Ala Leu Thr Asp Pro Tyr
                435                 440                 445
Thr Cys Leu Ser Ser Asp Val Phe Pro Leu Met Met Phe Ile Leu Ile
            450                 455                 460
Phe Ile Ile Asn Ala Ser Met Ala Tyr Gln Thr Gly Thr Ala Met Asn
465                 470                 475                 480
Leu Ala Arg Asp Leu Gly Pro Arg Leu Ala Leu Tyr Ala Val Gly Phe
                485                 490                 495
Asp His Lys Met Leu Trp Val His His His Phe Phe Trp Val Pro
                500                 505                 510
Met Val Gly Pro Phe Ile Gly Ala Leu Met Gly Gly Leu Val Tyr Asp
                515                 520                 525
Val Cys Ile Tyr Gln Gly His Glu Ser Pro Val Asn Trp Ser Leu Pro
            530                 535                 540
Val Tyr Lys Glu Met Ile Met Arg Ala Trp Phe Arg Arg Pro Gly Trp
545                 550                 555                 560
Lys Lys Arg Asn Arg Ala Arg Arg Thr Ser Asp Leu Ser Asp Phe Ser
                565                 570                 575
Tyr Asn Asn Asp Asp Asp Glu Glu Phe Gly Glu Arg Met Ala Leu Gln
                580                 585                 590
Lys Thr Lys Thr Lys Ser Ser Ile Ser Asp Asn Glu Asn Glu Ala Gly
            595                 600                 605
Glu Lys Lys Val Gln Phe Lys Ser Val Gln Arg Gly Lys Arg Thr Phe
        610                 615                 620
Gly Gly Ile Pro Thr Ile Leu Glu Glu Glu Asp Ser Ile Glu Thr Ala
625                 630                 635                 640
Ser Leu Gly Ala Thr Thr Thr Asp Ser Ile Gly Leu Ser Asp Thr Ser
                645                 650                 655
Ser Glu Asp Ser His Tyr Gly Asn Ala Lys Lys Val Thr
                660                 665
```

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gagctctaga atgagtaatc ctcaaaaagc tc                                    32

```
<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggatcctcat gttaccttct tagcattac                                        29

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ataacgccta ttgtcccaat aag                                              23

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
catctcgaaa aagggtttgc                                                  20
```